US011710546B2

(12) United States Patent
Newman

(10) Patent No.: US 11,710,546 B2
(45) Date of Patent: Jul. 25, 2023

(54) EVALUATION OF PRESCRIBED DEVICES OR SERVICES

(71) Applicant: MENICON SINGAPORE PTE LTD., Singapore (SG)

(72) Inventor: Stephen D. Newman, Singapore (SG)

(73) Assignee: Menicon Singapore Pte Ltd., Singapore (SG)

( * ) Notice: Subject to any disclaimer, the term of this patent is extended or adjusted under 35 U.S.C. 154(b) by 0 days.

(21) Appl. No.: 16/666,113

(22) Filed: Oct. 28, 2019

(65) Prior Publication Data

US 2020/0066385 A1 Feb. 27, 2020

Related U.S. Application Data

(63) Continuation-in-part of application No. PCT/SG2018/050211, filed on Apr. 30, 2018.

(30) Foreign Application Priority Data

Apr. 28, 2017 (SG) .......................... 10201703534X

(51) Int. Cl.
*G16H 20/00* (2018.01)
*G16H 10/60* (2018.01)
*G06Q 30/0601* (2023.01)

(52) U.S. Cl.
CPC .............. *G16H 20/00* (2018.01); *G16H 10/60* (2018.01); *G06Q 30/0641* (2013.01)

(58) Field of Classification Search
CPC ........ G16H 20/00; G16H 10/60; G16H 40/67; G16H 20/40; G16H 20/70; G16H 40/63;

(Continued)

(56) References Cited

U.S. PATENT DOCUMENTS 9,798,385 B1 * 10/2017 Das ..................... A61B 5/4824
2002/0103673 A1 8/2002 Atwood
(Continued)

FOREIGN PATENT DOCUMENTS

JP 2002258222 A 9/2002
JP 2014170426 A 9/2014
(Continued)

OTHER PUBLICATIONS

Fan, Xin; Silica-Based Composite Nanoparticles as Ph-Responsive Drug Carriers and their Application in Contact Lens Drug Delivery; Auburn University, ProQuest Dissertations Publishing, 2017. 30264212. (Year: 2017).*

(Continued)

*Primary Examiner* — Hiep V Nguyen
(74) *Attorney, Agent, or Firm* — Dorsey & Whitney LLP

(57) ABSTRACT

Disclosed herein are systems and techniques for evaluating prescribed optical devices during use. A method can include matching a user profile with a prescribed optical device, matching the prescribed optical device with a plurality of members of a distribution system of the prescribed optical device, requesting information about the prescribed optical device through a user interface, receiving information in response to requesting the information, and sending feedback based on the received information to one of the members of the distribution system. One or more network devices can generate a user interface including information associated with the prescribed optical device and the user profile. The user interface can be adapted based on a primary or secondary user of the network device. The user interface can also be adapted as the user progresses in age, treatment schedule, and/or other factors that support evaluation of the prescribed optical device.

26 Claims, 43 Drawing Sheets

(58) Field of Classification Search
CPC ...... G16H 15/00; G16H 20/10; G02C 13/005; G02C 7/02
USPC .......................................................... 705/3
See application file for complete search history.

(56) References Cited

U.S. PATENT DOCUMENTS

| | | | |
|---|---|---|---|
| 2003/0007123 A1* | 1/2003 | Broderick | G06Q 30/0601 351/159.74 |
| 2003/0130973 A1* | 7/2003 | Sumner, II | G16H 50/50 706/45 |
| 2004/0105073 A1* | 6/2004 | Maddalena | A61B 3/032 351/205 |
| 2004/0174499 A1 | 9/2004 | Toshima et al. | |
| 2005/0160009 A1* | 7/2005 | Tanaka | G02C 13/003 705/304 |
| 2008/0094571 A1 | 4/2008 | Tarrant | |
| 2011/0125521 A1 | 5/2011 | Dhoble | |
| 2013/0339043 A1* | 12/2013 | Bakar | G16H 20/10 705/2 |
| 2014/0129259 A1 | 5/2014 | Seriani | |
| 2015/0100342 A1 | 4/2015 | Schulte | |
| 2015/0127359 A1 | 5/2015 | Iravani | |
| 2015/0142548 A1 | 5/2015 | Cable et al. | |

FOREIGN PATENT DOCUMENTS

| | | | |
|---|---|---|---|
| KR | 20140013991 A | 2/2014 | |
| WO | WO-2010117386 A1 * | 10/2010 | ............. A61B 3/032 |
| WO | 2011041281 A1 | 4/2011 | |
| WO | WO-2017134275 A1 * | 8/2017 | ........ G01M 11/0257 |

OTHER PUBLICATIONS

International Search Report and Written Opinion of PCT/SG2018/050211, dated Aug. 7, 2018.
Search Report and Written Opinion for Singapore Application No. 11201910067S, dated Feb. 12, 2021.

* cited by examiner

EVALUATION OF PRESCRIBED DEVICES OR SERVICES

CROSS-REFERENCE TO RELATED APPLICATIONS

This application is a continuation-in-part of International Application No. PCT/SG2018/050211, filed Apr. 30, 2018, which claims the benefit of Singapore Application No. 10201703534X, filed Apr. 28, 2017, the disclosures of which are incorporated by reference herein in their entireties.

FIELD

The described embodiments relate generally to prescribed optical devices, and more particularly to systems and techniques for evaluating prescribed optical devices during use.

BACKGROUND

Often, those who wear spectacles or contact lens visit a doctor to measure their eyesight so they can receive a prescription for a pair of spectacles or contact lenses. The prescription is given to the patient, who orders the spectacles or contact lenses through a supplier. In many cases, the doctor and the supplier are different entities that do not have a formal relationship. The supplier can be an online retailer or a business operating out of rented space in a supermarket, mall, business office, or another location. When the supplier receives the prescription, the supplier can provide appropriate spectacles or contact lenses the meet the prescription with either spectacles or contact lenses that are already in their inventory or the supplier can order the spectacles or contact lenses from a manufacturer. Often, communications between the doctor and the supplier and/or the manufacturer is limited, but the user is more likely to communicate with the doctor than with the supplier and the manufacturer.

Further, patients can visit a doctor for many other reasons outside of eye care. For example, a patient can seek treatment from a doctor for physical as well as mental ailments. Often, a doctor can devise or prescribe a specific treatment plan for a patient to follow, or seek to monitor a patient's physical or mental wellbeing based on their reported symptoms. However, a patient can go an extended period of time between doctor visits. As a result, important information such as how the treatment plan is working for the patient, side effects of the treatment plan, whether the patient is following the treatment plan, and whether any adjustments should be made to the treatment plan is only received intermittently by the doctor. In some cases where a patient can regularly report information to a doctor outside of an in-person visit, the patient can still not receive timely updates or other information from their doctor base on the reported information.

One type of system for interacting with a doctor is disclosed in U.S. Patent Publication No. 2015/0127359 issued to Nikki Iravani. In this reference, a system to host an interaction platform for users comprises a network and a host computer. The host computer is connected to the network, and the host computer provides a healthcare management platform for one or more users to interact for the purpose of the users interfacing management. The users are comprised of at least one healthcare provider user, at least one patient user, a mobile application interface module for the patient user to access the healthcare management platform, a dashboard interface module for the healthcare provider user to access the healthcare management platform, and an appointment module allowing the patient user to request an appointment with the healthcare provider user via the mobile application interface module. The appointment module further allows the healthcare provider to respond to the appointment request via the dashboard interface module. In one embodiment, the healthcare management platform is further comprised of a messaging module wherein the messaging module allows the patient user to communicate to the healthcare provider user and allows for the healthcare provider user to communicate to the patient user. This publication is herein incorporated by reference for all that it discloses.

SUMMARY

Embodiments of the present invention are directed to the evaluation of prescribed optical devices.

In an embodiment, a method for evaluating a prescribed optical device is disclosed. The method includes matching a user profile with a prescribed optical device. The method further includes associating a network device with a primary user or a secondary user. The user profile corresponds to the secondary user. The method further includes presenting information about the prescribed optical device of the primary user through a user interface of the network device based on the association of the network device with the primary or the secondary users. The method further includes generating feedback associated with use of the prescribed optical device through the user interface that is adapted to one of the primary or secondary users.

In another embodiment, the primary user can be a parent and the secondary user can be a child.

In another embodiment, in a first mode, the network device can be associated with the primary user. The operation of presenting information can further include generating a first user interface having a first quantity of attributes associated with use the prescribed optical device. In a second mode, the network device can be associated with the secondary user. The operation of presenting information can further include generating a second user interface having a second quantity of attributes associated with use the prescribed optical device. The second quantity of attributes can be a condensed version of the first quantity of attributes.

In another embodiment, in a first mode, the network device can be associated with the primary user. The operation of presenting information can further include generating a first user interface having a textual depiction of attributes associated with the prescribed optical device. In a second mode, the network device can be associated with the secondary user. The operation of presenting information can further include generating a second user interface having a graphical depiction of attributes associated with the prescribed optical device. The graphical depiction can be visually representative of textual depiction.

In another embodiment, in a first mode, the network device can be associated with the primary user. The operation of presenting information can further include generating a first user interface depicting a representation of a history of interactions of the secondary user with the prescribed optical device. In a second mode, the network device can be associated with the primary user. The operation of presenting information can further include generating a second user interface depicting a representation of rewards based on the history of interaction of the secondary user with the prescribed optical device.

In another embodiment, the operation of associating can include receiving an input at the network device. The operation of associating can further include determining the input corresponds to one of the primary user or the secondary user. The network device can be associated with the secondary user. In this regard, the operation of presenting information can further include providing a prompt for transitioning the network device to the primary user via the input. In some cases, the operation of receiving can include capturing one or more images of the primary user or the secondary user for one or both of a facial recognition process or a retina scan process, using one or more sensors of the network device.

In another embodiment, the method can further include requesting information about the prescribed optical device through the user interface of the network device. In some cases, the method can further include receiving information in response to requesting the information, and attributing the received information to one of the primary or secondary users.

In another embodiment, the operation of generating feedback can further include updating the user interface based on the received information and the attribution of the received information to one of the primary or secondary users. In some cases, the method can further include matching the prescribed optical device with a plurality of members of a distribution system. In this regard, the method can further include sending feedback based on the received information to one of the members of the distribution system. The members of the distribution system can include one or more of a prescriber of the prescribed optical device, a supplier of the prescribed optical device, or a manufacture of prescribed optical device.

In another embodiment, the prescribed optical device can be a contact lens.

In another embodiment, a method for evaluating a prescribed optical device. The method includes matching a user profile with a prescribed optical device. The method further includes generating a first user interface at a network device that includes information associated with the prescribed optical device. The method further includes computing a progression characteristic of the user profile. The method further includes, in response to the progression characteristic satisfying a boundary condition, generating a second user interface at the network device that includes modified information associated with the prescribed optical device.

In another embodiment, the user profile can include information corresponding to one or more of an age of a user of the prescribed optical device, a compliance history of the user for the prescribed optical device, a treatment progress history of the user for the prescribed optical device, or a medical history of the user of the prescribed optical device. In this regard, the operation of computing can further include computing the progression characteristic using one or more of the age of the user, the compliance history of the user, the treatment progress history of the user, or the medical history of the user.

In another embodiment, the boundary condition can be associated with a milestone for a combination of one or more of the age of the user, the compliance history of the user, the treatment progress of the user, or the medical history of the user. The milestone can be indicative of a progression-based appropriateness of the modified information for the user. In some cases, one or more of the age of the user, the compliance history of the user, the treatment progress history of the user, or the medical history of the user is determined, at least in part, using sensors of the network device that are configured to capture one or more images for one or both of a facial recognition process or a retina scan process.

In another embodiment, the boundary condition can be a first boundary condition. In this regard, in response to the progression characteristic satisfying another boundary condition, the method can further include generating a third user interface including further modified information associated with the prescribed optical device.

In another embodiment, the method can further include requesting information about the prescribed optical device through the first user interface or the second user interface of the network device.

In another embodiment, the method can further include receiving information in response to requesting the information, and attributing the received information to one of the first user interface or the second user interface.

In another embodiment, the method can further include generating feedback associated with use of the prescribed optical device through the network device that is adapted to one of the first user interface of the second user interface.

In another embodiment, the first user interface can include a depiction of a first quantity of attributes associated with use the prescribed optical device. Further, the second user interface can includes a depiction of a second quantity of attributes associated with use of the prescribed optical device. The second quantity of attributes can be a condensed version of the first quantity of attributes.

In another embodiment, a system for evaluating a prescribed optical device is disclosed. The system includes a processor. The system further includes a display of a network device. The display is configured to define a user interface. The system further includes a memory coupled to the processor. The memory is for storing instructions which, when executed by the processor, causes the processor to match a user profile with a prescribed optical device. The instructions which, when executed by the processor, further causes the processor to generate a first user interface at the display including information associated with the prescribed optical device. The instructions which, when executed by the processor, further causes the processor to receive one or more inputs associated with a user of the network device. The instructions which, when executed by the processor, further causes the processor to using the received feedback, generate a second user interface including modified information associated with the prescribed optical device.

In another embodiment, the memory stores further instruction which, when executed by the processor, causes the processor to associate the network device with a primary user or a secondary user, the user profile corresponding to the secondary user. The instructions which, when executed by the processor, can further cause the processor to generate the first user interface at the display based on the association of the network device with the primary user or the secondary user.

In another embodiment, in a first mode, the network device can be associated with the primary user. The first graphical interface can include a first quantity of attributes associated with use the prescribed optical device. In a second mode, the network device can be associated with the secondary user. The first graphical interface can include a second quantity of attributes associated with use of the prescribed optical device. The second quantity of attributes can be a condensed version of the first quantity of attributes. The first quantity of attributes can be visually represented via the first user interface with text, and the second quantity of attributes can be visually represented via the second user interface with icons.

In another embodiment, the operation of associating can include using the one or more received inputs to transition the network device between a child mode associated with the secondary user and a parent mode associated with the primary user.

In another embodiment, the memory stores further instructions which, when executed by the processor, causes the processor to compute a progression characteristic of the user profile. The instructions which, when executed by the processor, can further cause the processor to, in response to the progression characteristic satisfying a boundary condition, generate the second user interface including the modified information. In some cases, the user profile can include information corresponding to one or more of an age of a user of the prescribed optical device, a compliance history of the user for the prescribed optical device, a treatment progress history of the user for the prescribed optical device, or a medical history of the user of the prescribed optical device. In this regard, the operation of computing can further include computing the progression characteristic using one or more of the age of the user, the compliance history of the user, the treatment progress history of the user, or the medical history of the user.

In another embodiment, the memory can store further instructions which, when executed by the processor, causes the processor to match the prescribed optical device with a plurality of members of a distribution system of the prescribed optical device. The instructions which, when executed by the processor, can further cause the processor to request information about the prescribed optical device through a user interface. The instructions which, when executed by the processor, can further cause the processor to receive information in response to requesting the information. The instructions which, when executed by the processor, can further cause the processor to send feedback based on the received information to one of the members of the distribution system.

In another embodiment, the memory can store further instructions which, when executed by the processor, cause the processor to receive a signal from one of the members of the distribution system, based on the sent feedback. The instructions which, when executed by the processor, can further cause the processor to update one or both of the first or second interfaces based on the received signal.

In another embodiment, the members of the distribution can include one or more of a prescriber of the prescribed optical device, a supplier of the prescribed optical device, or a manufacture of prescribed optical device.

In another embodiment, a method can include matching a user profile with a prescribed optical device, matching the prescribed optical device with a plurality of members of a distribution system of the prescribed optical device, requesting information about the prescribed optical device through a user interface, receiving information in response to requesting the information, and sending feedback based on the received information to one of the members of the distribution system.

In another embodiment, an apparatus can include means for matching a user profile with a prescribed optical device, means for matching the prescribed optical device with a plurality of members of a distribution system of the prescribed optical device, means for requesting information about the prescribed optical device through a user interface, means for receiving information in response to requesting the information, and means for sending feedback based on the received information to one of the members of the distribution system.

In another embodiment, an apparatus can include a processor, memory in electronic communication with the processor, and instructions stored in the memory. The instructions can be operable to cause the processor to match a user profile with a prescribed optical device, match the prescribed optical device with a plurality of members of a distribution system of the prescribed optical device, request information about the prescribed optical device through a user interface, receive information in response to requesting the information, and send feedback based on the received information to one of the members of the distribution system.

In another embodiment, a non-transitory computer-readable medium can include instructions operable to cause a processor to match a user profile with a prescribed optical device, match the prescribed optical device with a plurality of members of a distribution system of the prescribed optical device, request information about the prescribed optical device through a user interface, receive information in response to requesting the information, and send feedback based on the received information to one of the members of the distribution system.

In some examples of the method, apparatus, and non-transitory computer-readable medium described above, at least one of the members of the distribution system can be a prescriber of the prescribed optical device.

In some examples of the method, apparatus, and non-transitory computer-readable medium described above, at least one of the members of the distribution system can be a supplier of the prescribed optical device.

In some examples of the method, apparatus, and non-transitory computer-readable medium described above, at least one of the members of the distribution system can be a manufacturer of the prescribed optical device.

In some examples of the method, apparatus, and non-transitory computer-readable medium described above, the prescribed optical device can be a contact lens.

In some examples of the method, apparatus, and non-transitory computer-readable medium described above, the prescribed optical device can be spectacles.

In some examples of the method, apparatus, and non-transitory computer-readable medium described above, the information includes an eye comfort level.

In some examples of the method, apparatus, and non-transitory computer-readable medium described above, the information includes an eye dryness level.

In some examples of the method, apparatus, and non-transitory computer-readable medium described above, the information includes an aspect about inserting the prescribed optical device to a user's eye.

Some examples of the method, apparatus, and non-transitory computer-readable medium described above can further include processes, features, means, or instructions for awarding a benefit to the user in response to sending the requested information.

In some examples of the method, apparatus, and non-transitory computer-readable medium described above, the benefit includes a discount on future purchases of prescribed optical devices.

Some examples of the method, apparatus, and non-transitory computer-readable medium described above can further include processes, features, means, or instructions for linking a user responding to the requested information to a member of the distribution system in response to receiving an unsatisfactory threshold rating in the requested information.

Some examples of the method, apparatus, and non-transitory computer-readable medium described above can further include processes, features, means, or instructions for linking the user to the member in real time.

Some examples of the method, apparatus, and non-transitory computer-readable medium described above can further include processes, features, means, or instructions where linking includes opening a text communication channel with the member of the distribution system.

In some examples of the method, apparatus, and non-transitory computer-readable medium described above, the feedback includes processed information based on the received information.

In some examples of the method, apparatus, and non-transitory computer-readable medium described above, the processed information includes a frequency of unsatisfactory ratings.

In some examples of the method, apparatus, and non-transitory computer-readable medium described above, the processed information includes associating the received information with a material of the prescribed optical device.

In some examples of the method, apparatus, and non-transitory computer-readable medium described above, the processed information includes associating the received information with a manufacturing date of the prescribed optical device.

In some examples of the method, apparatus, and non-transitory computer-readable medium described above, the processed information includes associating the received information with a location of the user using the prescribed optical device.

In some examples of the method, apparatus, and non-transitory computer-readable medium described above, the processed information includes associating the received information with at least one aspect of the weather in the area of the user using the prescribed optical device.

In some examples of the method, apparatus, and non-transitory computer-readable medium described above, the processed information includes associating the received information with a batch group identifier of the prescribed optical device.

In some examples of the method, apparatus, and non-transitory computer-readable medium described above, the processed information includes associating the received information with at least one aspect of the manufacturing of the prescribed optical device.

In some examples of the method, apparatus, and non-transitory computer-readable medium described above, the processed information includes associating the received information with the prescriber of the prescribed optical device.

Some examples of the method, apparatus, and non-transitory computer-readable medium described above can further include processes, features, means, or instructions for linking includes presenting an option to schedule an appointment with a member of the distribution system.

In some examples of the method, apparatus, and non-transitory computer-readable medium described above, the feedback includes the received information in an unprocessed format.

Some examples of the method, apparatus, and non-transitory computer-readable medium described above can further include processes, features, means, or instructions for sending the received information to a server. Some examples of the method, apparatus, and non-transitory computer-readable medium described above can further include processes, features, means, or instructions for generating the feedback at the server.

Some examples of the method, apparatus, and non-transitory computer-readable medium described above can further include processes, features, means, or instructions for requesting information includes requesting information daily.

Some examples of the method, apparatus, and non-transitory computer-readable medium described above can further include processes, features, means, or instructions for aggregating the received data.

Some examples of the method, apparatus, and non-transitory computer-readable medium described above can further include processes, features, means, or instructions for providing instructions on a use of the prescribed optical device.

In some examples of the method, apparatus, and non-transitory computer-readable medium described above, the prescribed optical device can be a contact lens.

In another embodiment, a method can include matching a user profile with a prescribed optical device, matching the prescribed optical device with a plurality of members of a distribution system of the prescribed optical device, requesting comfort information about the prescribed optical device, receiving the comfort information in response to requesting the comfort information, sending the received comfort information to a server, processing the received comfort information at the server, sending feedback based on the received comfort information to one of the members of the distribution system, and linking a user responding to the requested comfort information to a member of the distribution system in response to receiving an unsatisfactory threshold rating in the requested information.

In another embodiment, an apparatus can include means for matching a user profile with a prescribed optical device, means for matching the prescribed optical device with a plurality of members of a distribution system of the prescribed optical device, means for requesting comfort information about the prescribed optical device, means for receiving the comfort information in response to requesting the comfort information, means for sending the received comfort information to a server, means for processing the received comfort information at the server, means for sending feedback based on the received comfort information to one of the members of the distribution system, and means for linking a user responding to the requested comfort information to a member of the distribution system in response to receiving an unsatisfactory threshold rating in the requested information.

In another embodiment, an apparatus can include a processor, memory in electronic communication with the processor, and instructions stored in the memory. The instructions can be operable to cause the processor to match a user profile with a prescribed optical device, match the prescribed optical device with a plurality of members of a distribution system of the prescribed optical device, request comfort information about the prescribed optical device, receive the comfort information in response to requesting the comfort information, send the received comfort information to a server, process the received comfort information at the server, send feedback based on the received comfort information to one of the members of the distribution system, and link a user responding to the requested comfort information to a member of the distribution system in response to receiving an unsatisfactory threshold rating in the requested information.

In another embodiment, a non-transitory computer-readable medium can include instructions operable to cause a processor to match a user profile with a prescribed optical device, match the prescribed optical device with a plurality of members of a distribution system of the prescribed optical device, request comfort information about the prescribed optical device, receive the comfort information in response to requesting the comfort information, send the received comfort information to a server, process the received comfort information at the server, send feedback based on the received comfort information to one of the members of the distribution system, and link a user responding to the requested comfort information to a member of the distribution system in response to receiving an unsatisfactory threshold rating in the requested information.

In another embodiment, a method can include receiving real time comfort information about prescribed optical devices matched to a manufacturer, analyzing the comfort information by aggregating a total number of unsatisfactory ratings contained in the comfort information, categorizing types of the unsatisfactory ratings, and recommending a change to a manufacturing process in response to reaching a predetermined threshold of the unsatisfactory ratings.

In another embodiment, an apparatus can include a processor, memory in electronic communication with the processor, and instructions stored in the memory. The instructions can be operable to cause the processor to receive real time comfort information about prescribed optical devices matched to a manufacturer, analyze the comfort information by aggregating a total number of unsatisfactory ratings contained in the comfort information, categorize types of the unsatisfactory ratings, and recommend a change to a manufacturing process in response to reaching a predetermined threshold of the unsatisfactory ratings.

In another embodiment, a system for tracking the comfort level of a contact lens can include a first mobile device in communication with a remote location associated with a first user, a second mobile device in communication with the remote location associated with a second user, a feedback manager that categories responses from the first user and the second user into separate categories, at least one of the categories being a negative category, an aggregator that identifies common characteristics among the responses categorized within the negative category when a percentage of responses are categorized into the negative category, and an recommender that recommends an action based on the common characteristics within the negative category.

Some examples of the method and apparatus described above can further include processes, features, means, or instructions for recommending the change includes temporarily stopping a portion of the manufacturing process.

Some examples of the method and apparatus described above can further include processes, features, means, or instructions for recommending the change includes a material change to a material included in a batch of the prescribed optical devices.

Some examples of the method and apparatus described above can further include processes, features, means, or instructions for recommending the change includes a geometry change to a geometry included in a batch of the prescribed optical devices.

Some examples of the method and apparatus described above can further include processes, features, means, or instructions for recommending the change includes a shelf life change to a shelf life included in a batch of the prescribed optical devices.

In another embodiment, method and apparatus for evaluating a prescribed product or service includes matching a user profile with a prescribed product or service, receiving information from the user and generating an automated feedback response based on the received information.

Some examples of the method and apparatus described above can further include providing the received information and the automated feedback response to a doctor or other medical professional, and sending feedback based at least in part on a response from the doctor or other medical professional through the user interface.

Some examples of the method and apparatus described above can further include analyzing biomarker information.

Some examples of the method and apparatus described above can further include requesting information from a user through a user interface.

Some examples of the method and apparatus described above can further include displaying an avatar of the doctor via the user interface.

Some examples of the method and apparatus described above can further include the avatar delivering the feedback to the user.

Some examples of the method and apparatus described above can further include generating an automated feedback response includes inputting facts into an artificial intelligence system.

In addition to the exemplary aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
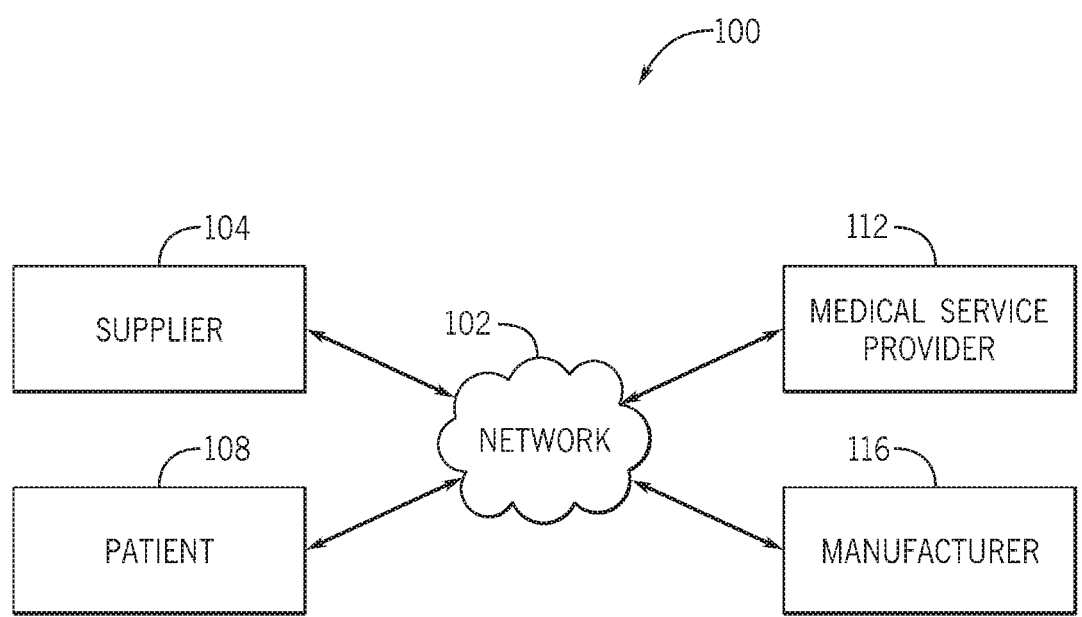
FIG. 1 depicts an example distributed computing system.

The description that follows includes sample systems, methods, and apparatuses that embody various elements of the present disclosure. However, it should be understood that the described disclosure can be practiced in a variety of forms in addition to those described herein.

The principles described in the present disclosure include systems, methods, and devices for improving communication between a patient and a treating doctor. Additionally, the present exemplary systems and methods improve communication between the patient using prescribed medications, optical devices, such as contact lenses or spectacles, or other devices, and members of a distribution system for distributing the prescribed devices. The members of the distribution system can include a prescriber, such as an ophthalmologist, an optometrist, an optician, a medical doctor, a therapist, another type of licensed medical professional, or combinations thereof. Also, the suppliers and the manufacturers can be members of the prescribed devices' distribution system.

The principles disclosed herein also include systems, methods, and devices for improving communication between the patient receiving treatment or monitoring for one or more mental or physical conditions, such as Alzheimer's disease, depression, and anxiety, and one or more members of a medical team for treating the mental or physical condition. The members of the medical team can include a prescriber, such as a doctor, therapist, a nurse, a medical assistant, another type of medical professional, or combinations thereof. The medical team can also include members of a distribution system for distributing medications, devices, or combinations thereof. The members of the distributions system can include suppliers, manufacturers, or distributors, of medication or devices, or combinations thereof.

The principles disclosed herein can include ways to gain feedback from the users of the prescribed products or services, such as optical devices, medications, other devices, services, and treatment plans, open real-time communication links between the member of the distribution system, medical team, and the user, set up appointments between the distribution system members, medical team members, and the user, and result in improvement between the prescriptions or treatment plans to the user and/or improvements to the prescribed medications, optical devices, or other devices. For example, the feedback facilitated through the principles described in the present disclosure can include the analysis of data that was unknown to the medical team, manufacturer, or suppliers in the past. This information can be used to make recommendations for changes in the materials, geometries, shelf life, aqueous solutions, packaging, instructions, dosages, configurations, and other aspects of the spectacles, contact lenses, medications, other devices, and treatment plans.

The principles disclosed herein can also include devices and methods for enhancing engagement, data collection, and communication between a user and the user's doctor or medical professional. For example, the devices described herein can lead to increased user engagement with a prescribed product or service, which can in turn result in enhanced user compliance with a doctor's instructions. In turn, the ability of the devices and methods described herein to facilitate communication between a doctor and user even outside of in-person visits or phone call, thus resulting in increased user satisfaction and an increased ability for the doctor to monitor the health and compliance of the user. The principles disclosed herein also allow a doctor to interact with more users than they might otherwise be able to if restricted only to in-person visits from patients, thereby allowing a doctor to expand their practice.

In one aspect of the principles described in the present disclosure, mobile devices are used in an unconventional manner to provide inputs that drive improvements to medications, devices, services, treatment plans, or optical devices such as contact lenses. In some embodiments, this information can be supplemented by automatically collected data, for example via one or more sensors. In one particular example, a mobile device obtains comfort level information from multiple users, aggregates that data when certain predetermined thresholds of negative responses are obtained, and provides an input used in improving the contact lens. In some cases, a certain percentage of negative responses out of a pre-identified population trigger a grouping/matching process that identifies issues for a contact lens manufacturer to solve.

In another example, a mobile device obtains information from a patient, such as a happiness level, a pain level, a level of cognition, physiological information, and combinations thereof. The obtained information can be provided to a medical team or other party who can use the information to monitor the efficacy or adjust the details of a particular medication, device, service, or treatment plan which can be subscribed to the patient. In some cases, information from multiple users can be aggregated and can be used in improving a particular medication, device, service, or treatment plan used by multiple users.

In some embodiments, a mobile device can be used to provide information to a patient relating to their mental or physical health, personal history, medication, device, service, treatment plan, or combinations thereof. In some cases, the information provided to a patient can be monitored, determined, or otherwise controlled by a member of a medical team, such as a doctor. For instance, the mobile device can provide a patient having Alzheimer's disease with information related to their location, health status, instructions for a treatment plan, the date, or any other relevant information as determined by a member of the medical team.

In some embodiments, one or more sensors can be used to automatically collect information from a user relating to their mental or physical health, personal history, medication, device, service, treatment plan, or combinations thereof. For example, in some cases a contact lens including one or more sensors can collect biological information from a user's tear fluid. In some cases, the collected information can be provided to a doctor for analysis and monitoring. Any feedback or responses from the doctor can then be provided to the user by a device as described herein.

Reference will now be made to the accompanying drawings, which assist in illustrating various features of the present disclosure. The following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

FIG. 1 depicts an example distributed computing system 100. The distributed computing system 100 can include a supplier 104, a patient 108, a medical service provider 112, and a manufacturer 116. The supplier 104, the patient 108, the medical service provider 112, and the manufacturer 116 can be communicatively connected to one another via a network 102. The network 102 can facilitate communication among the supplier 104, the patient 108, the medical service provider 112, and the manufacturer 116 via a remote or distributed communication network, such as the Internet.

The systems and techniques of the present disclosure can facilitate evaluation of prescribed optical devices. For example, the patient 108 can have a prescribed optical device, such as contact lenses, and the systems and techniques herein can be used to gather substantially real-time information corresponding to the use of the prescribed optical device, and generate feedback based on this gathered information. More specifically, the patient 108 can use a network device to provide information pertaining to use of the prescribed optical device. This can include a comfort level of the lens, daily habits associated with use (e.g., compliance with a treatment plan), performance or efficacy of the prescribed optical device, and so on.

The system 100 can facilitate the foregoing evaluation of prescribed optical devices by communicatively associating the patient 108 with parties of a distribution system associated with the prescribed optical device. In the example of FIG. 1, the distribution system can include the supplier 104, the medical service provider (or prescriber) 112, and the manufacturer 116. The medical service provider 112 can be associated with a medical doctor, or other party or office that prescribes an optical device. The manufacture 116 can be associated with one or more aspects of a supply chain that produces the prescribed optical device. The supplier can be associated with one or more aspects of a supply chain that supplies the prescribed optical device, which in some cases can include a retail store or other point-of-sale of the prescribed optical device to the patient 108 or end user.

According to the systems and techniques herein, the patient 108 can use a network device to provide substantially real-time information to members of the distribution system, via the network 102. The members of the distribution system can receive this information, and execute various functions. For example and as described in greater detail below, the members of the distribution system can receive information pertaining to the comfort of the prescribed optical device, and make changes to the prescribed optical device accordingly. As an illustration, the medical service provider 112 can receive information associated with a comfort level of the prescribed optical device and make adjustments to a prescription, such as changing a lens size. The manufacturer 116 can receive information associated with a comfort level of the prescribed optical device, and aggregate this information across a set of users to analyze manufacturing techniques and procedures. The supplier 104 can receive information associated with a comfort level of the prescribed optical device, and consider recommending different optical device options for the patient 108 that could achieve the same vision correction, for example, but with a potentially higher comfort level. It will be appreciated that the foregoing is described for purposes of illustration, other characteristics of the prescribed optical device can be evaluated additionally or in the alternative to the comfort level. Also, other members of the distribution system can receive the information and respond in other appropriate fashions.

The systems and techniques herein can also be used to provide substantially real-time or other feedback to the patient 108. This feedback can be based, in part, on the information provided by the patient 108 for the evaluation of the prescribed optical device by the members of the distribution system. Continuing the foregoing example for comfort level, the patient 108 can receive, via a network device, information from one or more members of the distribution system for improving the comfort level, as appropriate. As one example, an informational message can be provided to the user regarding proper techniques for wearing the prescribed optical device. The evaluation of the prescribed optical can also be iterative in this regard. For example, if the patient 108 continues to report low levels of comfort after receiving the information messages, subsequent messages can be provided to the patient 108, including messages prompting the patient 108 to schedule a visit to the medical service provider 112.

Figure 2:
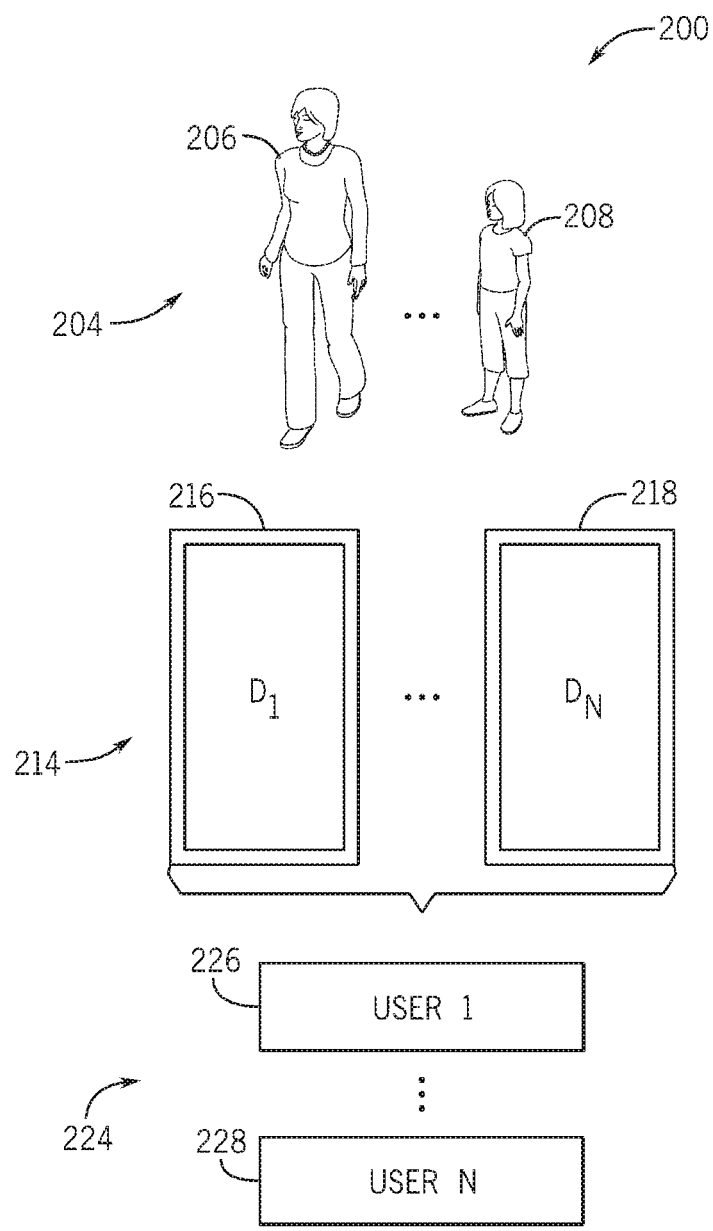
FIG. 2 depicts a diagram illustrating an example system with multiple users and device in accordance with the present disclosure.

FIG. 2 depicts an example system 200 with multiple users, devices, and user profiles, in accordance with the present disclosure. The systems and techniques of the present disclosure can be used to evaluate prescribed optical devices in multiple different contexts. In some cases, the patient or user of the prescribed optical device is different from the user of the network device. Accordingly, described herein are adaptive processes through which different information can be obtained and delivered associated with the prescribed optical device, based on a variety of factors, including which user and/or which device is accessing the system.

To illustrate this relationship, the system 200 is shown as including users 204, devices 214, and user profiles 224. The users 204 can a include primary user 206 and a secondary user 208, and/or other users. The primary user 206 can be a parent and the secondary user 208 can be a child. One or both of the primary user 206 or the secondary user 208 can be a user or patient associated with the prescribed optical device. The systems and techniques herein can evaluate the prescribed optical device in a manner that is tailored or adapted for the primary or secondary users 206, 208, or both. As described in greater detail below, this can involve presenting information at a network device that is tailored or adapted to the primary or secondary user 206, 208 associated with the network device. Where the secondary user 208 is a child and the secondary user 208 is associated with the network device, this can allow the system 200 to present targeted or age-appropriate information at the network device. Correspondingly, where the primary user 206 is a parent and the primary user 206 is associated with the network device, this can allow the system 200 to present a fuller suite of options and information at the network device.

The system 200 is also shown with the devices 214, including a first device 216 and a second device 218, and/or other devices. In some cases, the first device 216 can be associated with the primary user 206 and the second device 218 can be associated with the secondary user; however, this is not required. For example, in other cases, the primary and secondary users 206, 208 may share or temporarily swap devices, such as where the primary user 206 is a parent and the secondary user 208 is a child. In this regard, the systems and techniques described herein operate to associate the primary or secondary user 206, 208 with a given one of devices 214, and then present information accordingly.

The system 200 is also shown with the user profiles 224, including a first user profile 226 and a second user profile 228, and/or other users profiles. Generally, the first user profile 226 can correspond to the primary user 206 and the second user profile 228 can correspond to the secondary user 228. The user profiles 224 can include information related to an optical device for the respective one of the users 204. The user profiles 224 can also include information related to the evaluation of the optical device, including a history of substantially real-time feedback from the respective user, and updates and the like from one or more members of the distribution system.

The systems and techniques herein can adapt the devices 214 based on an association of the device with a given user, and the accessing of a particular one of the user profiles 224. The system 200 can thus facilitate interactions in which one of the users 204 accesses a user profile that does not correspond to a prescribed optical device for that user. Considering the parent-child interaction, a parent or the primary user 206 can be associated with a network device, and the network device can be used to access a user profile of the child or user profile 228 of the secondary user 208. This can be desirable so that the parent can access a fuller suite of options, data summaries, programs, and the like in relation to the prescribed optical for the child. The same network device can be subsequently associated with the child, and enter a "child mode". In this sense, the network device can be used to provide a condensed or age-appropriate version of the information provided to the parent. The condensed or age-appropriate version can also be modified too, based on a progression characteristic of the child. As described herein, the progression characteristic can include metrics such as an age of a user of the prescribed optical device, a compliance history of the user for the prescribed optical device, a treatment progress history of the user for the prescribed optical device, or a medical history of the user of the prescribed optical device. In light of these and other characteristics, the information presented at the network device can be modified accordingly.

As described herein, the network device can be associated with the primary user 206 and/or the secondary user 208 in a variety of manners. In some cases, a password field, prompt, or other button (e.g., a virtual button) can be generated using a user interface on the device. The device can receive input at the respective user interface, such as receiving a password within a password field. The password can signify that the network device is being used by a user associated with the password, and thus the user interface can be updated accordingly (e.g., transition between a "parent" mode and a "child" mode).

Sensors of the network device can also be used to associate the device with the primary user 206 and/or the secondary user 208. For example, one or more sensors of the network device can be configured to capture one or more images of a user, such as images that can be used with one or both of a facial recognition process or a retina scan process. The sensors can be used to allow the device to confirm the identity of the user, and then use the identity of the user to associate the network device with a corresponding profile. This can be beneficial, for example, where there is only a single phone, and multiple people are accessing the system through the single phone. Sensors of the network device can also be used to adapt the user interface for the user, as described herein, including changing aspects of the user interface based on one or more of an age of the user, a medical of the user, a compliance history of the user, or a treatment progress of the user, all of which can be detected, at least in part using sensors that capture images used in a facial recognition process and/or a retina scan process.

Figure 3:
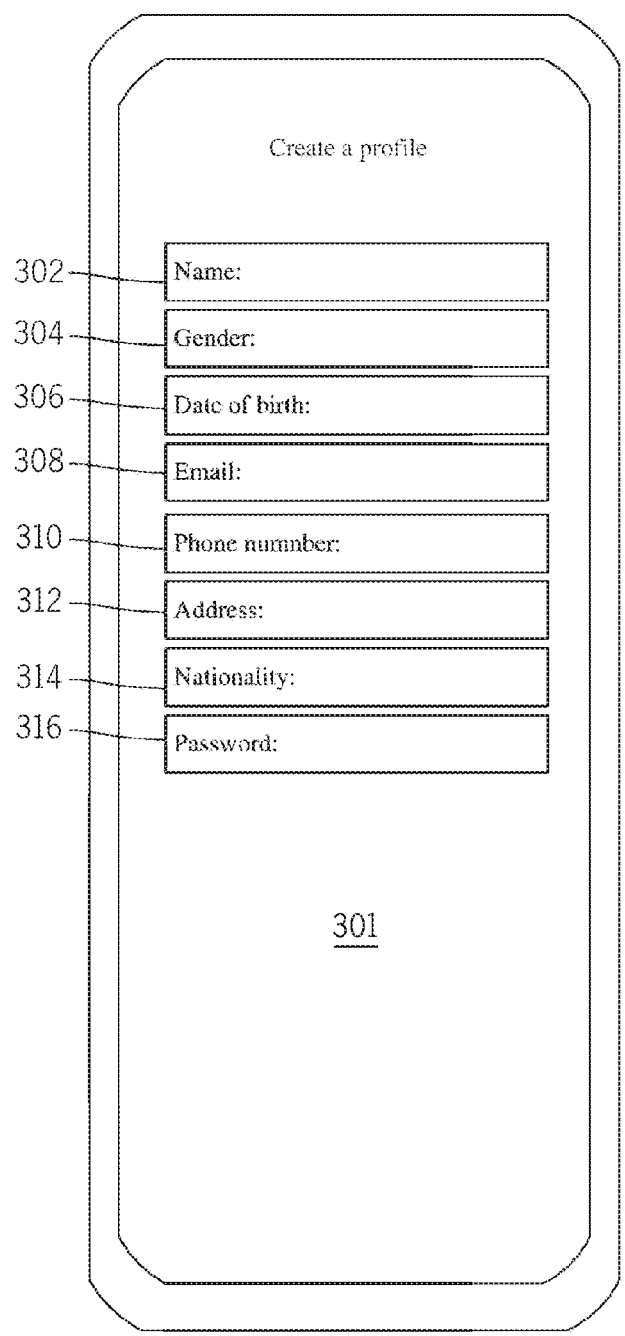
FIG. 3 depicts an example of a device for evaluating a prescribed device or service in accordance with aspects of the present disclosure.

FIG. 3 depicts an example of a device 300 that includes a user interface 301. The device 300 can be any appropriate type of device, such as a mobile device, a computing device, a smart phone, an electronic tablet, a laptop, a desktop, a digital device, networked device, another type of device, or combinations there. The user interface 301 can be any appropriate type of user interface. In some examples, the user interface is a touch screen. In other examples, the user interface includes buttons, knobs, dials, levers, switches, scroll bars, scroll balls, mouse pads, gesture recognition cameras, microphones, other types of user interface mechanisms, or combinations thereof.

In this example, the user interface 301 presents multiple fields to the user for creating a user profile. In this case, the user profile can be created by entering in at least one of the different types of information into the different fields presented. In this example, the fields include a name field 302, a gender field 304, a date of birth field 306, an email field 308, a phone number field 310, an address field 312, a nationality field 314, and a password field 316. While this example has been presented with specific types of fields, other examples can include more or fewer fields than those presented in the example of FIG. 3. Further, in some embodiments, one or more information fields can be automatically filled in, for example using patient information already on file with a medical provider, such as a doctor.

In some embodiments, the user interface 301 can present the pre-formed user profile to the user for confirmation of the information provided therein. The different fields of the user profile can assist the manufacturers, suppliers, and doctors by providing more patient feedback than would otherwise be available, especially in cases where information that the doctor has, such as nationality, age, sensitive medical information, and gender may not be known to the manufacturer, or can be protected personal health information. Often issues affecting a person's experience with contact lenses, spectacles, medications, devices, services, or treatment plans are more common in certain nationalities, certain age groups, certain areas of residence, other types of user characteristics, or combinations thereof.

The user profile can be matched to the user's doctor and the prescribed products or services used by the user. This can be done by inputting information regarding the user's doctor into the profile. In some cases, the user is also matched to his or her supplier. The information can also be collected through inputting the information into the phone. Over time, the user can switch providers and/or doctors. In those circumstances, the user can update the information in the profile. In other examples, this information can be updated through another appropriate way. For example, when a user purchases a set of contact lens, the supplier can cause the information to be pushed to the user's profile. In some embodiments, when a user switches doctors, or begins seeing a doctor for the first time, the doctor or another member of the medical team can update the user's profile or cause information to be pushed to the user's profile. Thus, the supplier can have a copy of the prescription, the doctor who issued the prescription, the time that the order was made, and so forth. This can be performed when the user is at one of the supplier's locations of business. In other examples, the purchase of the spectacles, contact lenses, medications, services, or other devices can occur through the user's profile.

In some cases, the supplier and/or the manufacturer can identify each of the prescribed products that are sent to the user. For example, each contact lens package, medication package, or other device package can be identified with an identification number or another type of identifier that can be recorded to the user's profile.

Figure 4:
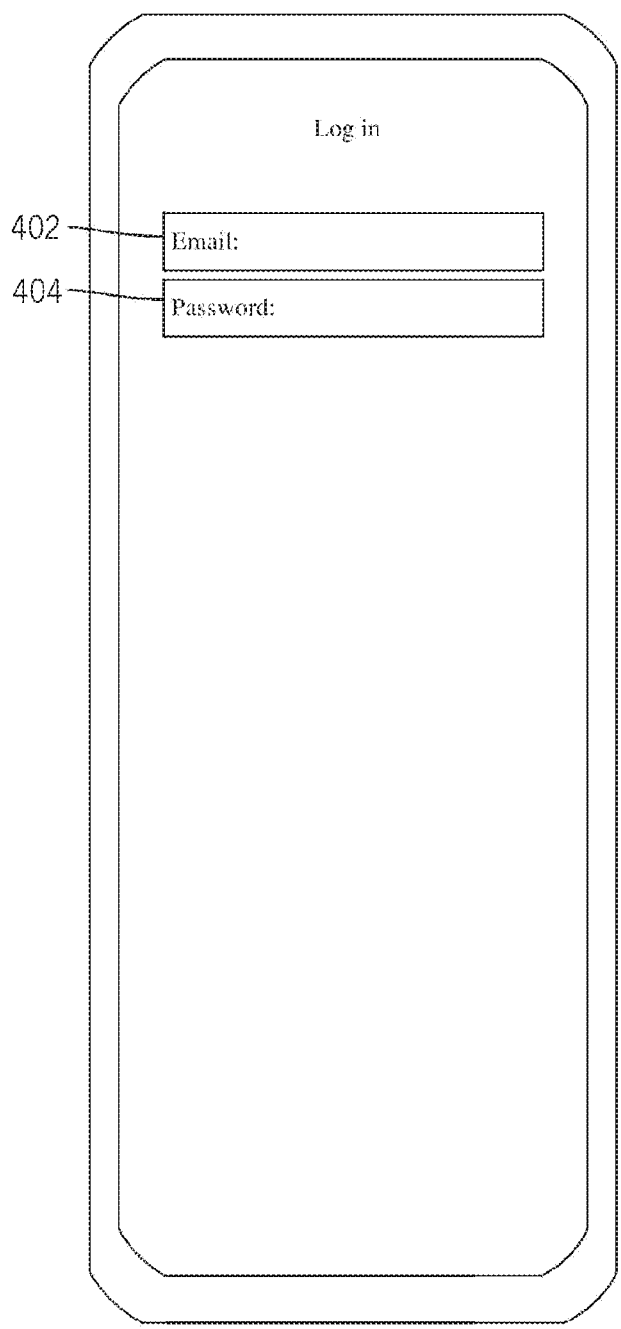
FIG. 4 depicts an example of a device for evaluating a prescribed device or service in accordance with aspects of the present disclosure.

FIG. 4 depicts an example of the user interface of the device 400 presenting fields for authentication before permitting a user from accessing the user profile. In this example, the device presents an email field 402 and a password field 404. While this example has been depicted with specific credentials to authenticate the user before granting access, any appropriate type of credentials can be used in other examples.

Figure 5:
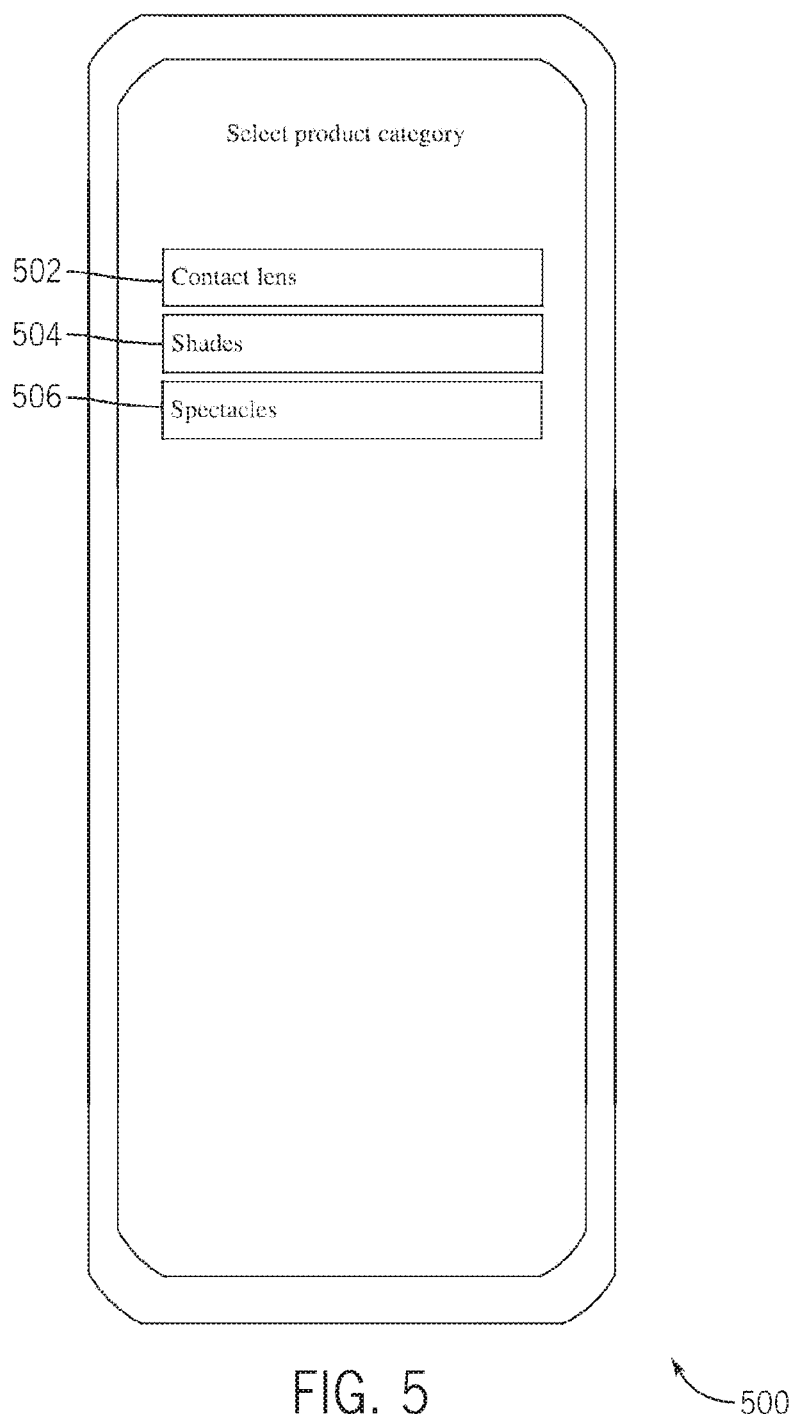
FIG. 5 depicts an example of a device for evaluating a prescribed device or service in accordance with aspects of the present disclosure.

FIG. 5 depicts an example of a device 500 presenting product or service category fields. In this example, the product or service category fields can include a contact lens field 502, a shades field 504, and a spectacles field 506. In some embodiments, a device 500 can present product or service category fields including on or more classes or types of medication, or one or more classes or types of devices, such as mobility devices, medical devices, other types of devices, or one or more types of services or treatment plans or combinations thereof. The user can select the appropriate field to narrow down his or her search for a prescribed product or service to be ordered by the user. In some cases, the user can have a single product or service associated with his or her profile. In other examples, the user can have multiple products or services associated with the user profile. While this example has been depicted with specific product or service categories, any appropriate type of product or service categories can be used in other examples.

Figure 6:
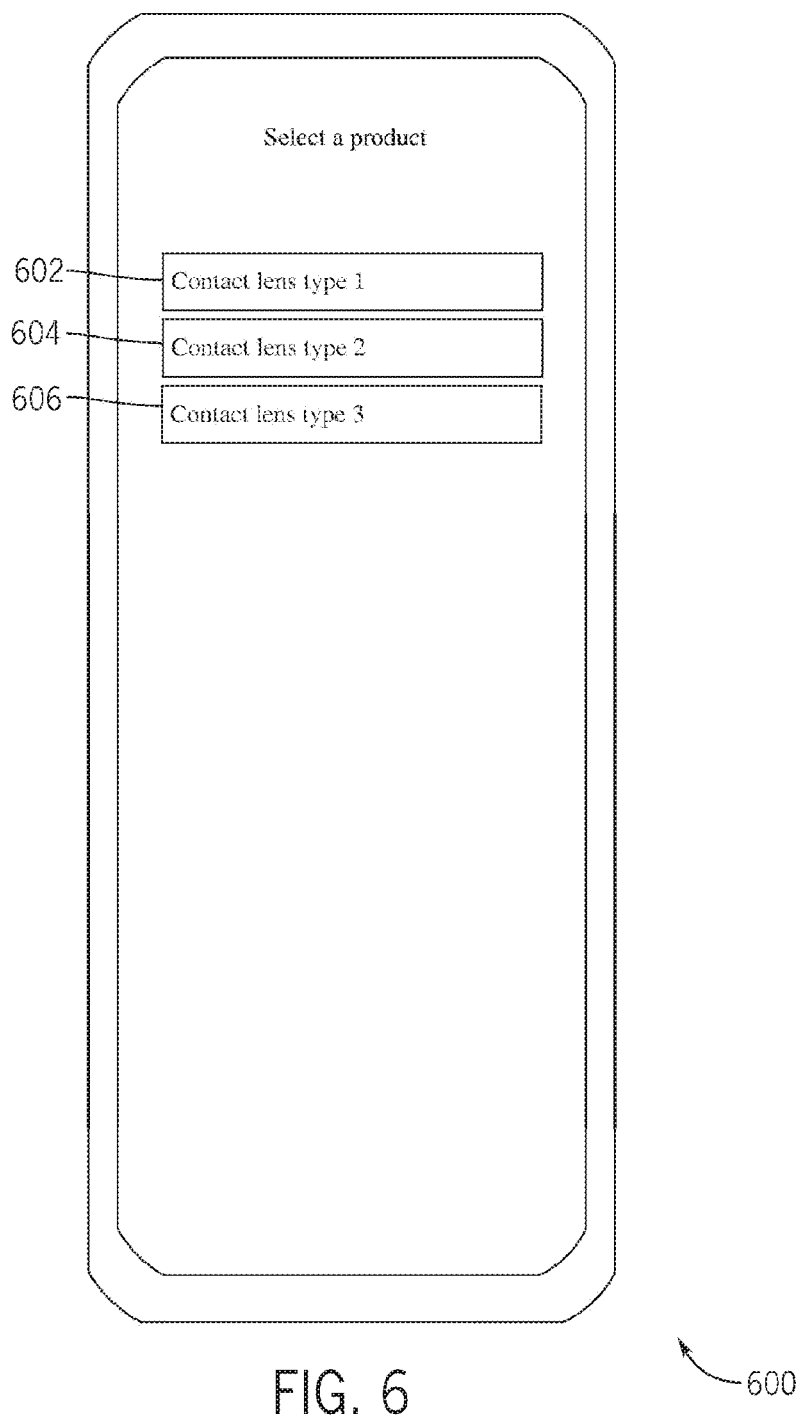
FIG. 6 depicts an example of a device for evaluating a prescribed device or service in accordance with aspects of the present disclosure.

FIG. 6 depicts an example of a device 600 presenting product or service type fields. In this example, the product or service type fields can include a contact lens type 1 field 602, a contact lens type 2 field 604, and a contact lens type 3 field 606. In some other embodiments, the product or service type fields can include multiple medication type fields, multiple device fields, or multiple service or treatment plan fields. The user can select the appropriate field to narrow down his or her search for a specific product or service purchased by the user or a specific plan to be followed by the user. In some cases, the product or service type fields represent only those products or services that have been purchased by the user. In other examples, the product or service type fields include more product or service types than those purchased by the user. In those situations where the product or service type fields correspond to those products or services that have not been purchased by the user, the user can gain access to general information about those product or service types. In those cases where the product or service type category corresponds to the products or services actually purchased by the user, the user can gain access to information like purchase dates, shipping dates, expiration dates, or other information that is specific to the types of the products or services actually purchased by the user. While this example has been depicted with specific product or service types, any appropriate type of product or service can be presented in other examples.

Figure 7:
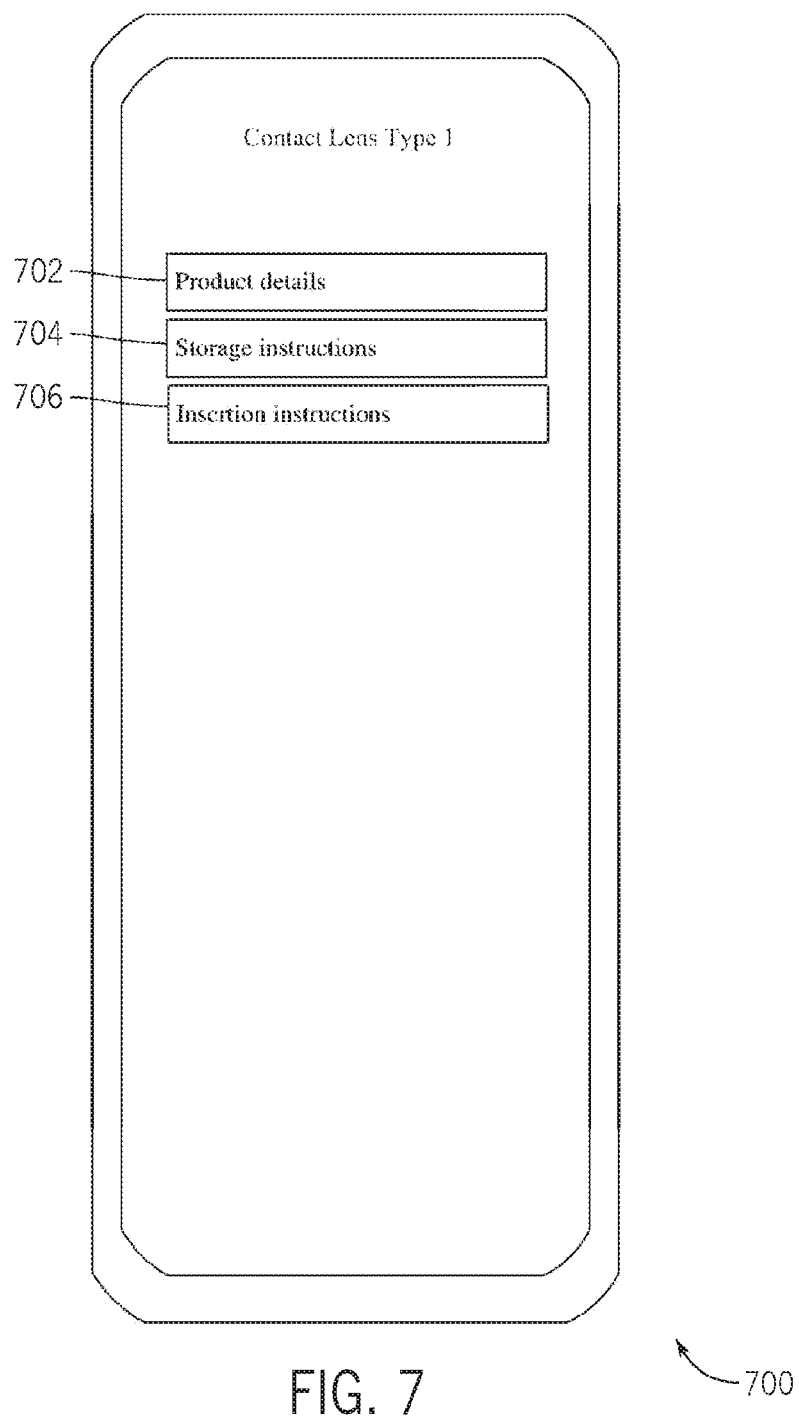
FIG. 7 depicts an example of a device for evaluating a prescribed device or service in accordance with aspects of the present disclosure.

FIG. 7 depicts an example of a device 700 that presents information accessible through the user profile about the type of product or service purchased, subscribed to or followed by the user or the types of products or services that have not necessarily been purchased by the user. In this case, the device 700 is presenting a product or service details field 702, a storage instructions field 704, and an insertion instructions field 706. The user can access these fields to read brochures, read user manuals, read user instructions, watch informational videos, or have access to other types of information about the presented products or services. In some embodiments, the device 700 can display additional information related to a product, medication, or plan that has been or can be purchased or followed by the user.

Figure 8:
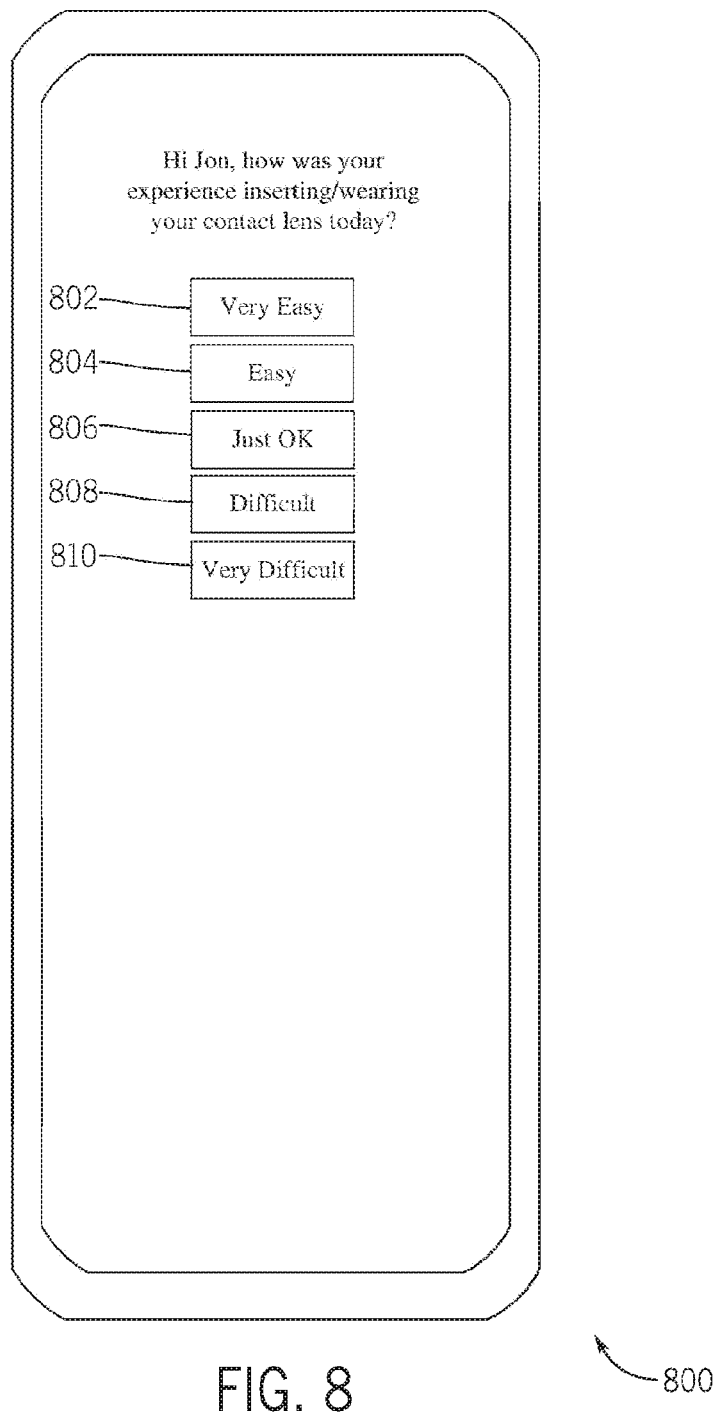
FIG. 8 depicts an example of a device for evaluating a prescribed device or service in accordance with aspects of the present disclosure.

FIG. 8 depicts an example of requesting information about the purchased products, services, or plans through device 800. In some examples, these questions can be accessed when the user accesses his user profile. In other examples, these questions can be presented to the user automatically based on the time of day or other types of triggers. For example, a request for how the contact lenses feel can be asked at predetermined times throughout the day. In other examples, questions about the user's experience with a certain product, service, or plan can be presented, for example, questions about the user's experience inserting the contact lens can be asked at a time shortly after the user is expected to insert his or her contact lenses. In some cases, requests for information can be received in the evenings where information about the user's experience throughout the day can be requested at a single time of the day. In some cases, the user can have the option to select when some or all of the information is requested. In some cases, the questions presented to the user can be written by, selected by, or otherwise determined by the user's prescribing physician or another such medical professional. In this way, the user's doctor can be able to solicit specific information from the user about their experience in order to more fully inform any evaluation or modifications to a product, service, or plan used by the user.

The request can be presented with multiple options for responding. In this case, the user can press a touch screen button that most appropriately reflects the user's experience. In this example, the user is presented a "very easy" button 802, an "easy" button 804, a "just OK' button 806, a "difficult" button 808, and a "very difficult" button 810. In other examples, more or fewer buttons can be presented to the user. In some cases, different type of moods, experiences, emotions, or other feelings can be described on the response buttons. In one example, the buttons can be depicted with an image of faces that reflect different types of user experiences. In other examples, word and images are presented together on the button. Further, the response mechanism can include another type of mechanism to communicate the user's answers. For example, the device can present the user with an open text field to describe his or her experience. In another example, the user can have an option to audibly speak his or her responses, or record a video message. In yet another embodiment, the user can be asked to rate his or her experience with a numeral value. In short, the examples described herein may not be limited to any particular type of presentation and/or responding mechanism. In some cases, a doctor, licensed medical professional a member of the medical team, or combinations thereof can determine the particular type of presentation and/or responding mechanism.

Figure 9:
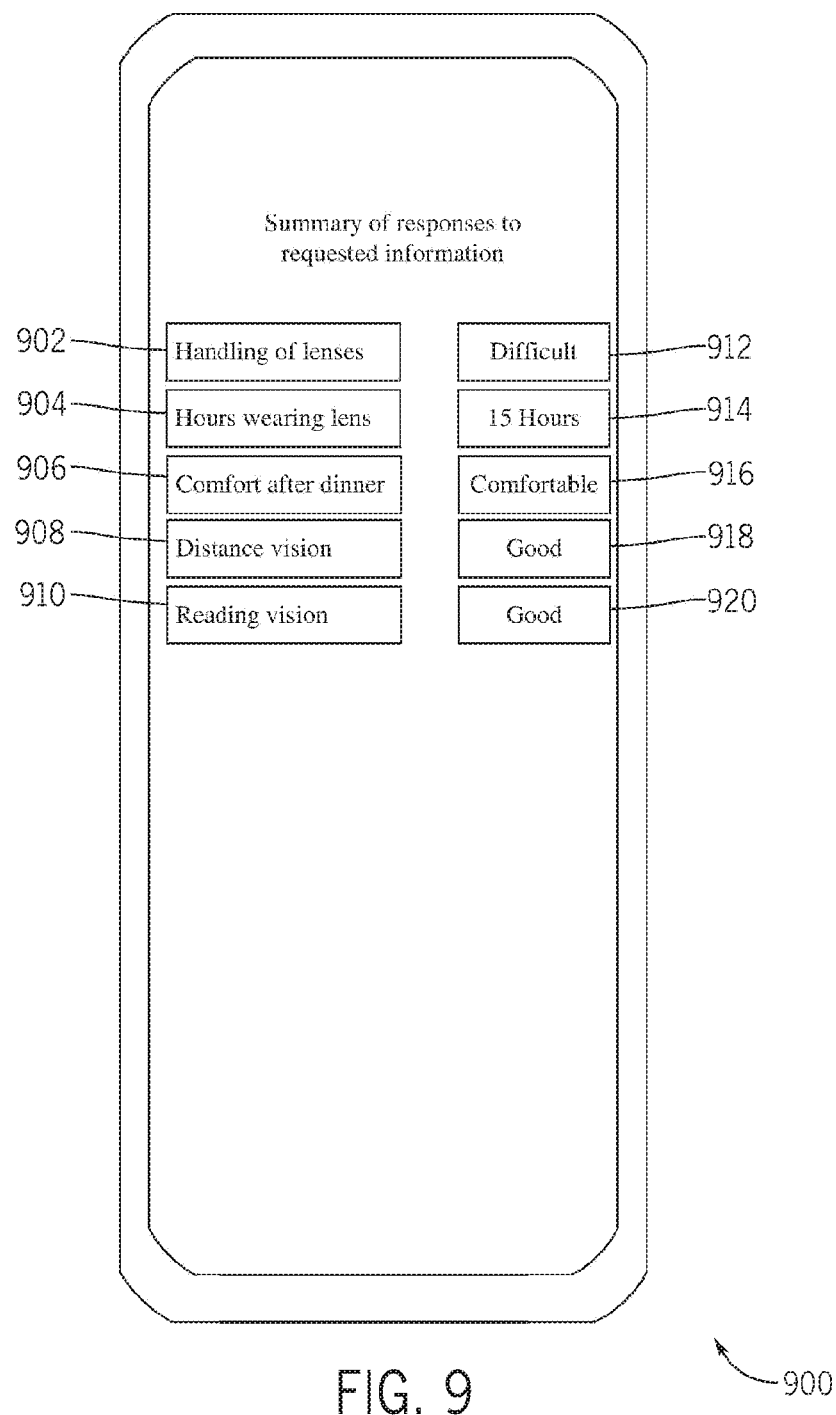
FIG. 9 depicts an example of a device for evaluating a prescribed device or service in accordance with aspects of the present disclosure.

FIG. 9 depicts an example of a device 900 presenting an example of a summary of different types of questions requested from the user. In this example, the types of information requested can include a handling of the lenses field 902, an hours wearing the lenses field 904, a comfort level after dinner field 906, a distance vision field 908, a reading vision field 910, another type of field, or combinations thereof.

In some cases, the device 900 requests information from the user on a daily basis. In some examples, the same type of information is requested every day. In some examples, the same type of information can be requested one or more times per day. In other examples, different types of questions are presented on different days or at different times on the same day. Asking different questions over a spread of time, such as days, hours, or weeks can allow a doctor, licensed medical professional, member of the medical team, or combinations thereof to get more information requested without overburdening the user with information requests each day and still allowing the device to gather information at a useful sampling rate. Additionally, consistent contact with the user by the system establishes a sense of relationship between the user and the doctor, licensed medical professional, member of the medical team, or combinations thereof.

Additionally, the device 900 can present the responses received from the user. In this example, the response field 912 indicates that the user had a difficult time handling the contact lenses, response field 914 indicates that the user wore the contact lenses for 15 hours on a given day, response field 916 indicates that the user's wearing experience was comfortable after dinner, response field 918 indicates that the user's distance vision was good, and response field 920 indicates that the user's reading vision was good. In some examples, the summary represents the responses that the user provided on a particular day. In some cases, the particular day is the same day that the responses were received. In some embodiments, the user can have an option of selecting a previous day to review the responses. The summary can represent an average or an aggregated amount of responses.

In some embodiments, a summary can be automatically generated from data collected from the user and can be presented to the user for review, confirmation, or other purposes. In some cases the device 900 can be connected to one or more sensors that automatically collected data from the user and relay the data to the device 900. For example, in some cases a user's contact lens can include one or more sensors to collect user data, such as physiological data, a duration for which the contact lens is worn, other data, or combinations thereof. The data collected by the one or more sensors can be transmitted or otherwise provided to the device 900, for example via a wireless network. Data collected by the one or more sensors can be automatically provided to the device 900, for example after a predetermined duration or after a predetermined condition is met. In some examples, a sensor, either in the contact lens or in a contact lens case, can detect a change in a biomarkers of a user which can trigger communication between the device 900 and a doctor or other medical professional. In some cases, when a predetermined condition is met, the user can be prompted with one or more questions related to their physical or mental health, as described herein. For example, in some cases a sensor can detect a change in a biomarker, which when compared to biomarker databases, can be associated with inflammation in the eye. The device 900 can then be triggered to prompt the user with questions relating to possible causes of the inflammation which can then be provided to a doctor along with the biomarker data.

In some embodiments, the user can be presented with a summary of the collected data on device 900 before, during, or after the data can be provided to the user's doctor, licensed medical professional a member of the medical team, or combinations thereof. In some cases, however, the data can be provided to the user's doctor, licensed medical professional, member of the medical team, or combinations thereof without being presented to the user.

Figure 10:
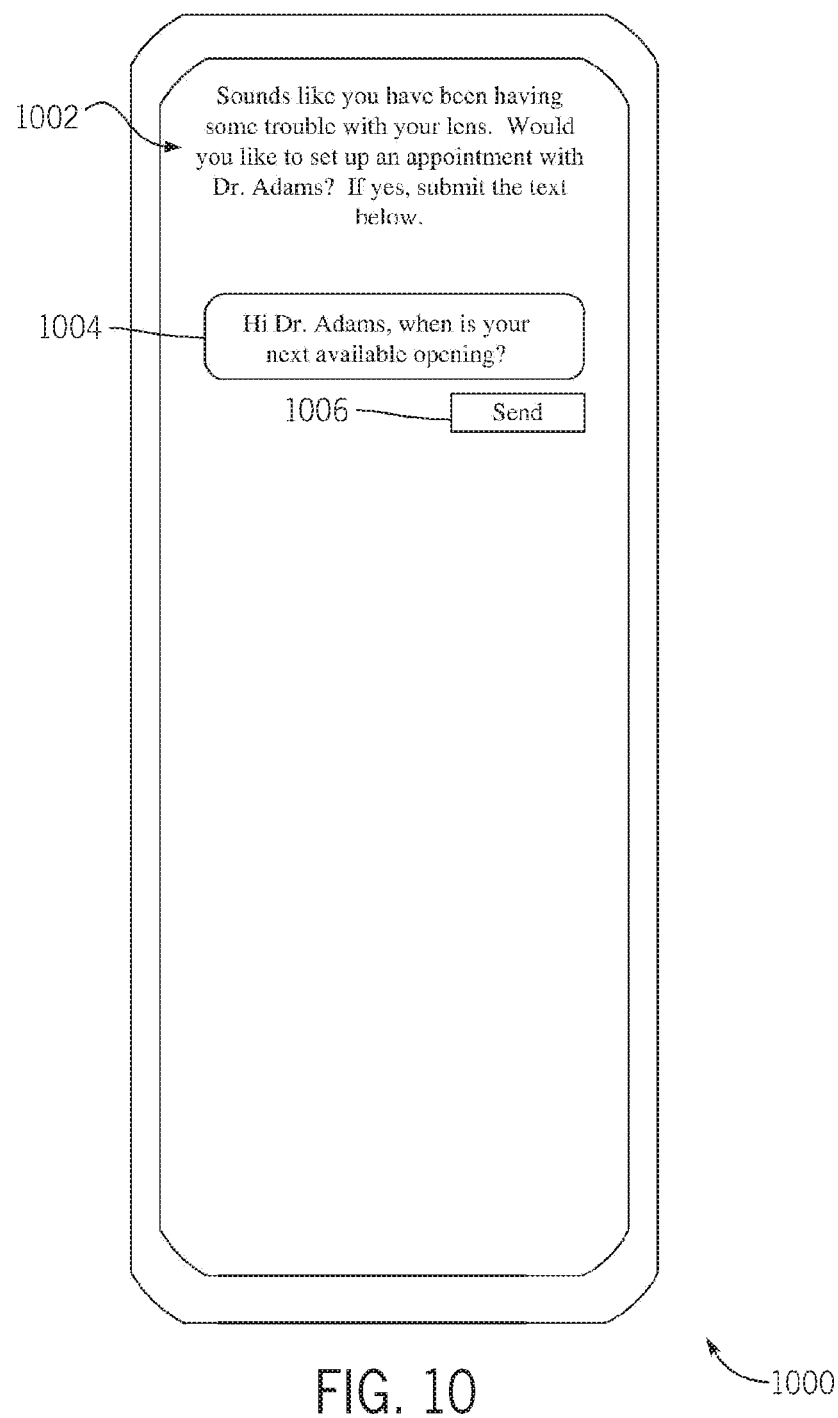
FIG. 10 depicts an example of a device for evaluating a prescribed device or service in accordance with aspects of the present disclosure.

FIG. 10 depicts an example of a device 1000 presenting a message to the user when the device determines that the user has included at least one unfavorable or undesirable rating in the provided information. The unfavorable ratings can include a level of discomfort, a level of pain, a level of a negative feeling, emotion, or sensation, physiological information such as dry eyes, difficulty using or following a product or service, such as difficulty inserting contact lenses, other unsatisfactory issues, or combinations thereof. In some cases, the threshold responding to an unfavorable rating is the inclusion of a single unsatisfactory rating. In other cases, additional unsatisfactory ratings are included before reaching that threshold. The user can be given an option to set the threshold level before the user's profile is causes the device 1000 to respond to the unsatisfactory user responses. In some cases, a user's doctor, licensed medical professional, member of the medical team, or combinations thereof can determine the threshold level.

In this case, a message 1002 is generated in response to reaching the threshold. The message 1002 asks the user if the user would like to set up an appointment with his or her doctor to discuss the issue. Below the message 1002, a text box is opened in which a message is automatically provided for the user. In some cases, the automatically generated message can be a starting point for the user. In this case, the text box's automate message requests an appointment with the doctor. If the user decides that the user wants to send the automated message 1004, the user can press the send button 1006. In other cases, if the user does not want to send what was automatically generated to the doctor, the user can type a new message or modify the generated message.

In other cases, the device 1000 can respond by generating a different type of message to be sent to another member of the distribution system. Examples of other possible automatically generated text messages can include, but are not limited to, sending messages to the manufacturer indicating a flaw in a particular batch of contact lenses, sending a message to the supplier indicating that a group of contact lenses went bad before the expiration date, a message indicating that the user would like to try a new type of contact lens, another type of message, or combinations thereof.

In some embodiments, the device 1000 can respond with a message generated by the user's doctor, licensed medical professional, member of the medical team, or combinations thereof instead of or in addition to an automatically generated message. For example, in some cases a doctor, licensed medical professional, member of the medical team, or combinations thereof can review user information, such as automatically collected data, or responses from the user, and provide a message to the user in response. In some cases, the message or information from the user's doctor, licensed medical professional, member of the medical team, or combinations thereof can be selected from one or more predetermined responses, or can be custom generated by the doctor, licensed medical professional, member of the medical team, or combinations thereof. In this way the user can receive personalized feedback from their doctor, licensed medical professional, member of the medical team, or combinations thereof, for example with adjustments to the user's treatment plan or revised instructions regarding a device or service. Thus, the device 1000 can facilitate engagement between the user and the medical team outside of scheduled visits, and can even reduce the need for in-person visits between the user and the medical team.

Figure 11A:
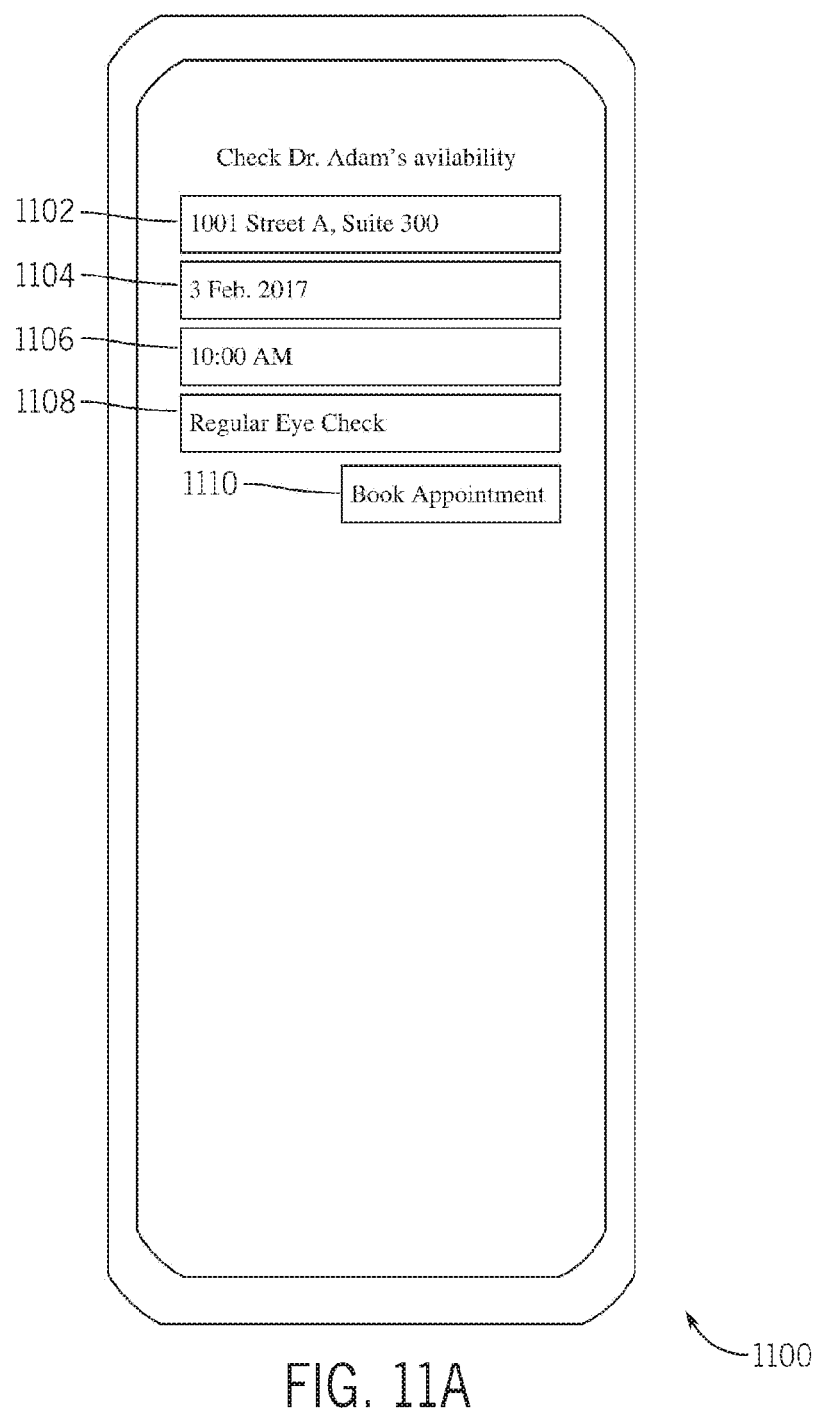
FIG. 11A depicts an example of a device for evaluating a prescribed device or service in accordance with aspects of the present disclosure.

FIG. 11A depicts an example of a device 1100 that checks the availability of the user's doctor. The user can use his user profile to check when his doctor is available for another visit. The user can request a visit, and the device 1100 can provide options for when the doctor is available. If one of the proposed appointments is suitable to the user, the user can select to book the appointment.

In the example of FIG. 11A, the device populates the number of fields based on the doctors availability. In this example, the device 1100 presents an address field 1102, a date field 1104, a time field 1106, and a reason field 1108. Additionally, the device can present a book button 1110 for the user to select if the appointment is suitable. In some cases, the user can input into at least one of the fields information about when the user is available and select the send button. In response, the device can be caused to search the doctor's calendar and retrieve at least one opening that fits the user's preferred availability, if any. If no times are available with the limitations imposed by the user's preferences, the device can indicate that the user should provide different options. Alternatively or additionally, the device 1100 can indicate the preferred times were unavailable, but offer some times that are available. While the examples above have depicted specific communications between a user and another party, any appropriate type of communication can be exchanged, for example the device 1100 can be used to schedule telephone calls, video conferences, and the like between the user and the doctor.

In one example, the user can have the option of communicating directly with his or her doctor through the device. In some examples, the user can select a button, icon, or another type of input device to enter into a program to interact with the doctor and/or a representative of the doctor. In some cases, the user can be interacting directly with an individual. In other examples, the user is interacting with a program that presents itself as a doctor. In some cases, the presented doctor can include a photo of a doctor, such as the user's doctor or another individual, or an avatar representing the doctor or another individual. In some cases, the avatar can be an animated avatar and can move in response to or accordance with a message provided by the doctor or other individual. For example, in some cases the avatar can appear as an animated drawing or digital depiction of a doctor and the avatar can include a mouth which moves in accordance with the message provided by the doctor. In those situations where the device presents itself as a doctor, the device can receive input from a remote source about which questions to ask the user. The questions and the user's responses can be sent to the user's doctors or to another appropriate party.

Figure 11B:
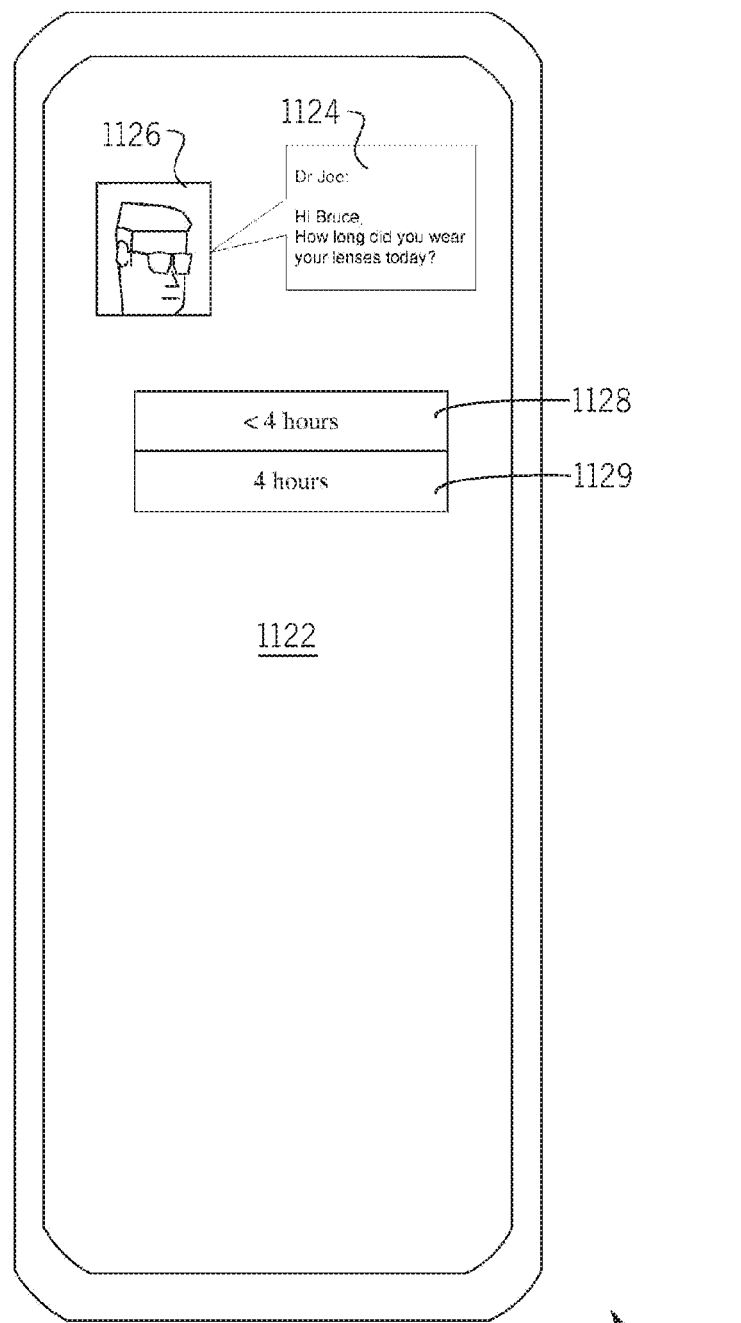
FIG. 11B depicts an example of a device for evaluating a prescribed device or service in accordance with aspects of the present disclosure.

FIG. 11B depicts an example of a device 1120 presenting a question through the device's display 1122. The device 1120 can present at least one question to the user to encourage the user to be in compliance with how to use his or her products, services, or plans. For example, the device

1120 can present one or more questions to the user to encourage the user to be in compliance with a preferred method of using his or her contact lenses or other types of products. For example, a daily disposable contact lens can be constructed to be worn by a user for a period less than 24 hours, but a user can try to wear the contact lens longer. With the questions presented to the user through the device, the user can be encouraged to wear the contact lens for just the appropriate time period. For example, the device can ask the user how long he or she wore the contact lens during the day. In some cases, the device can present the questions to the user through the device in a text message. In some examples, the message is presented to the user through a speech bubble 1124 that appears to be generated by the photo 1126 of the user's doctor or other individual. In yet other examples, the questions can be presented to the user through speakers in the device through an audible message.

In some cases, the device can also present pre-generated options 1128, 1129 for the user to select, such as a "less than four hours" option, a "four hours" option, a "more than four hours" option, an option with another time period, a "did not wear the contact lens" option, another type of option, or combinations thereof. In other examples, the user can type in the amount of time that the contact lens was worn. In other examples, the device can have a microphone into which the user can answer the question through a spoken sound.

In response to the user's selected option or other type of response, the device can give the user feedback. The feedback can include a confirmation that the user used the device, medication, or service in an appropriate manner, for an appropriate duration, or otherwise in accordance with the desired manner of use. For example, the feedback can include confirmation that the user wore the contact lens for the appropriate amount of time. The feedback can encourage the user to continue with the same course of action or to perform a different action in the future. For example, to wear the contact lens for a different time period in the future. In yet another example, the feedback can merely thank the user for providing a response.

In response to answering the question, the user can send a command through the device's interface to move on to another question or task. In other examples, the device can automatically present the user with another question or move on to another task.

Figure 11C:
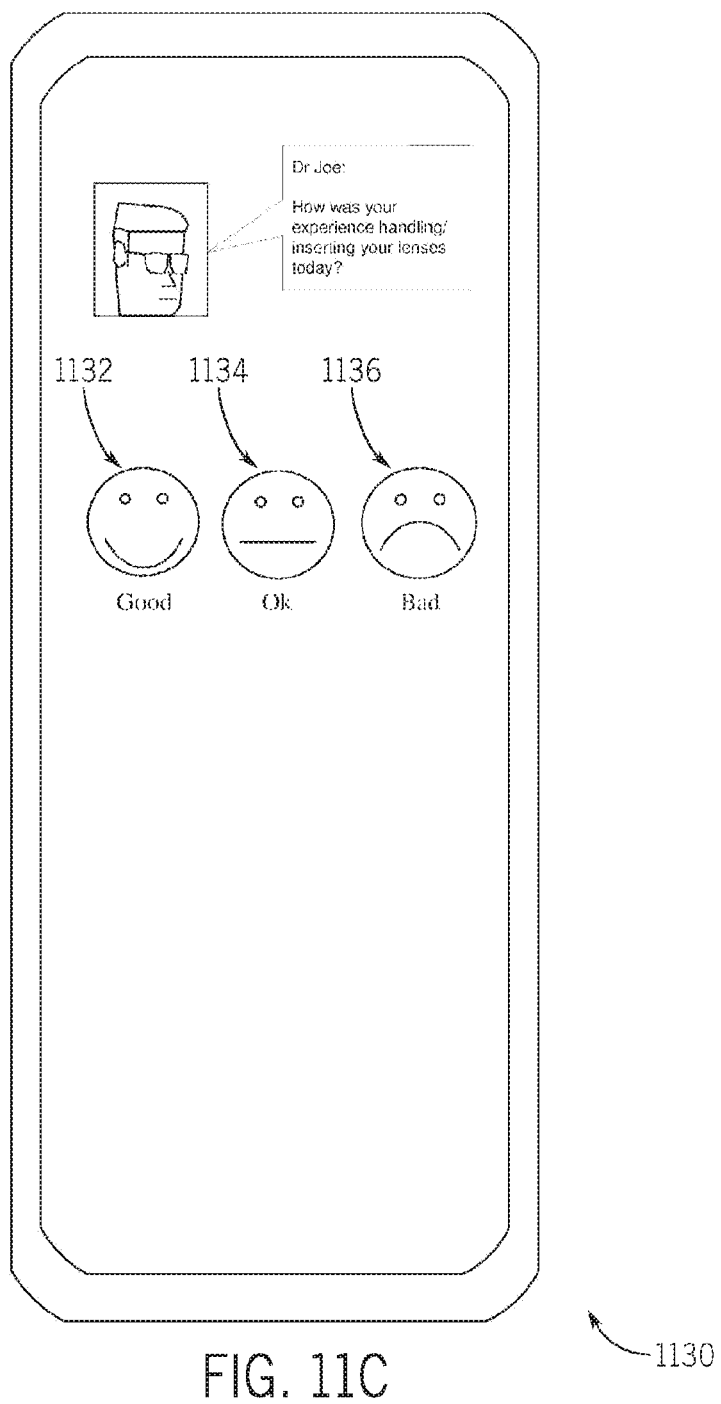
FIG. 11C depicts an example of a device for evaluating a prescribed device or service in accordance with aspects of the present disclosure.

FIG. 11C depicts an example of a device 1130 presenting a question to the user about how his or her experience was that day using a product or service or following a plan. For example, the question can related to how the user's experience was that day in wearing the contact lens, handling the contact lens, and/or inserting the contact lens. In some cases, the device 1130 can present icons 1132, 1134, 1136 that represent a good experience, an okay experience, a bad experience, another type of experience, or combinations thereof. The user can select the icon that he or she feels best describes his or her experience. In other examples, the user can be provided with a free text field that he or she can describe the experience, or the user can speak the experience into a microphone of the device, or record a video message related to their experience.

In those examples with an icon, the device can present an appropriate response. In those cases, where the user selects an icon 1132 representing a good experience, the device 1130 can congratulate the user or provide another type of positive feedback. In those cases where the user indicates that the experience was bad or just okay, the device can ask additional questions to determine what caused the experience to be less than optimal. In some cases, the device can provide suggestions for improving the user's experience. In some cases, the provided suggestions can be automatically generated or can be selected or otherwise provide by a doctor or other person.

The device can also present questions that relate to specific times during the day. For example, the device can present a question about the user's experience after breakfast, during the morning, after lunch, during the afternoon, after dinner, just before going to bed, during another time during the day, or combinations thereof. In some cases where the user is required to take a medication or perform and action at a specific time during the day the device can present questions at or after that specific time. In this example, the user can respond by selecting an appropriate icon, selecting a button, speaking a verbal command, interacting with another input mechanism, or combinations thereof.

In addition to asking general questions about the user's experience, the device can also or alternatively ask specific questions related to the user's experience or compliance. For example, in addition to asking about the user's comfort level with contact lenses, the device can also ask about how the user's vision was that day. In some embodiments, for example where a user is directed to take a medication, the device can ask about specific side effects or other physiological data, such as whether the user experienced a specific symptom or side effect and the extent to which they experienced the symptom or side effect. When asking about the user's experience, the device can ask about just a single aspect or multiple aspects of the user's experience. For example, when asking about the user's vision, the device can ask about the user's clarity, distance vision, near vision, light sensitivity, acuity, peripheral vision, central vision, right eye, left eye, depth perception, eye dryness, contrast sensitivity, night vision, field of view, distance accommodation, color acuity, tearing, eye pain, glare, double vision, reading vision, driving vision, other visual aspects, or combinations thereof.

Figure 11D:
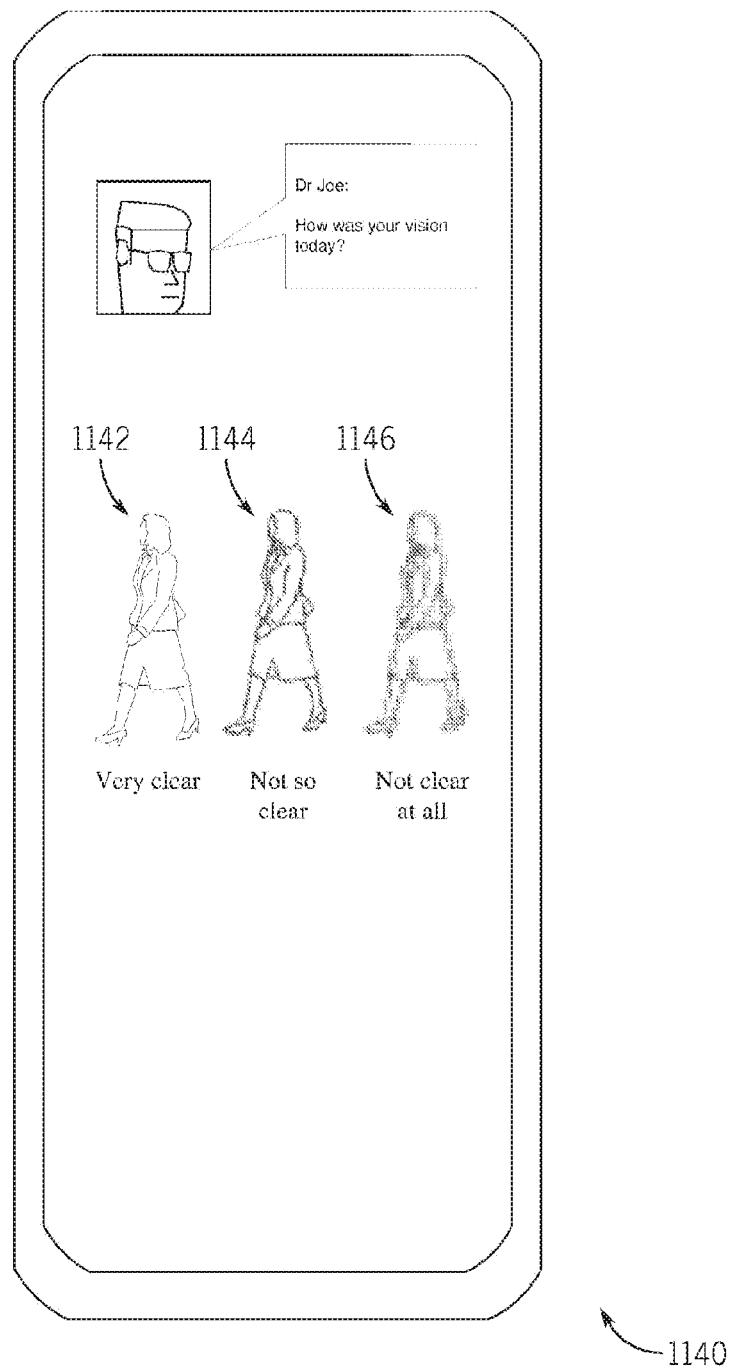
FIG. 11D depicts an example of a device for evaluating a prescribed device or service in accordance with aspects of the present disclosure.

FIG. 11D depicts an example of a device 1140 presenting a question about the user's experience, such as the user's visual experience. In the illustrated example, the device 1140 displays images of what the user can likely to have seen. In this example, the display presents multiple images 1142, 1144, 1146 that range from a clear image with crisp lines to an image with very blurry lines. The user can select the image that best fits his experience for that day. In other examples, the images can present the way the user saw that day based on other visual aspects.

The questions presented to the user through the device can be part of periodic tests. In some cases, a doctor can instruct the user to take the test on a periodic basis, such as a daily basis, a multi-day basis, a weekly basis, a monthly basis, a multi-hour basis, another basis based on another time period, or when a certain condition occurs, or combinations thereof. The responses to the test can be sent to the doctor or other medical professional. In some cases, the results of the test can be sent to another party, such as the manufacturer or a distributer. While the results of the test can be intended for the doctor to help the user's experience or condition in real time, a manufacturer or distributor can also have access to the user's responses. Aggregating the responses from multiple users can help the manufacturer or distributors make changes to a contact lens or other type of product or service. For example, the manufacturer can recognize that a significant portion of its clients experience a particular type of issue during a particular time of day. The changes can be made based on these observations. The distributor can recognize that certain product brands provide users with a better experience. As a result, the distributor can provide reviews about the brands that it offers. In some cases, the distributor can drop brands that perform poorly.

Figure 11E:
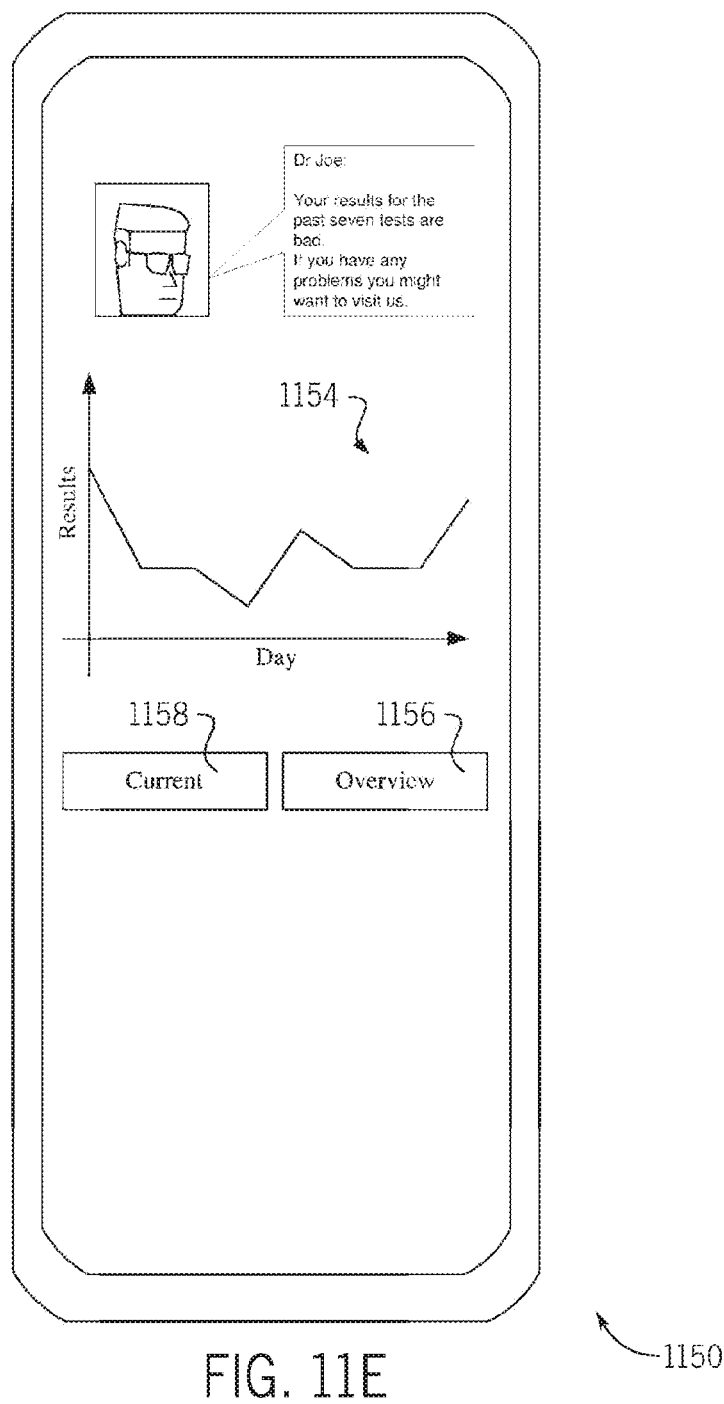
FIG. 11E depicts an example of a device for evaluating a prescribed device or service in accordance with aspects of the present disclosure.

FIG. 11E depicts an example of a device 1150 presenting in the display a summary 1152 of the answers to the user's questions. In some embodiments, the summary 1152 can be a summary of data automatically collected from the user, for example by one or more sensors. In some situations, the user can be given an option to change his or her answers or to correct any automatically collected data. In some examples, the device can offer instructional videos, literature, links to websites, or offer other forms of information based on the user's feedback.

The summary 1152 can include a line graph 1154, a pie chart, a bar graph, another type of graph, another type of chart, another type of visual summary, or combinations thereof. The summary can include such charts or graphs for each question asked, each type of data collected, or group multiple types of responses or data together. In some cases, the user can see the summary as desired by selecting an "overview" button 1156 or another type of icon. To return to the current set of questions, the user can select a "current" button 1158 or another type of icon.

Figure 12:
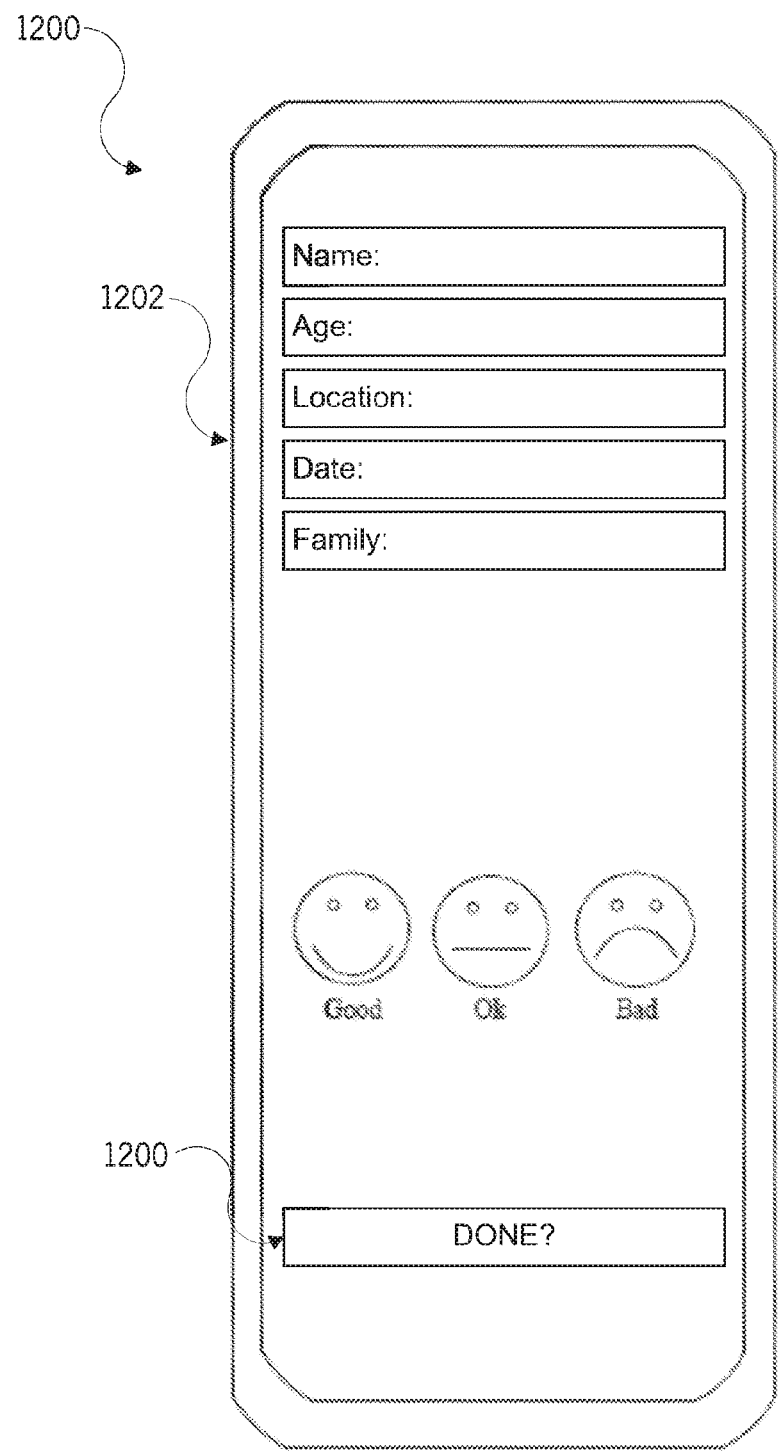
FIG. 12 depicts an example of a device for providing information and evaluating a prescribed device or service in accordance with aspects of the present disclosure.

FIG. 12 depicts an example of a device 1200 presenting in the display a summary 1202 of information to be provided to a user to update the user on their mental health, physical health, or other relevant information. In some embodiments, the summary 1202 can provide information to the user related to the upcoming use of a product, service, or plan during the future. For example, the summary 1202 can inform the user that they must perform a certain action, such as taking a medication, at specific times during the day.

In some other embodiments, the summary 1202 can remind or refresh the user about information that can have previously been provided or known to the user. For example, in some cases a user can have Alzheimer's disease which can cause the user to forget a wide range on information, including the user's location, name, age, family members, etc. Thus, in some embodiments the summary 1202 can remind the user of basic important information, such as their name, location, age, familial relationships, schedule for the day, other information, or combinations thereof.

The summary 1202 can be provided to the user at a specified time of day, for example at a specified time each morning. In some cases, the summary 1202 can be provided to the user at multiple times during the day as determined, for example, by a doctor. In some cases, the summary 1202 can be provided to the user when a specified condition is satisfied, such as when a user first turns on the device, when the user performs a desired action, some other condition, or combinations thereof.

The device 1200 can also provide the user with a prompt 1204 to allow the user to indicate when the user is done with the summary 1202. In some cases, the prompt 1204 can be a simple input, such as requiring the user to select that they are done. However, in some other cases the prompt 1204 can include one or more questions for the user, for example based on the information provided in the summary 1202. In some cases, the prompt 1204 can require the user to correctly answer one or more questions relating to the summary 1202. For example, where a user can have Alzheimer's disease, the prompt 1204 can ask the user to repeat some or all of the information provided in the summary 1202 to confirm retention of the information. In some cases, the user's responses to the prompt 1204 can be provided to the doctor, for example to compare with previous responses and to monitor a user's level of retention or cognition.

In some embodiments, the device 1200 can monitor the user's behavior and/or location, for example via location tracking technology such as global positioning system (GPS) technology or the like. In some cases, the device 1200 can transmit or otherwise provide the user's location to a third party such as a doctor, medical professional, or other person, such as a family member. In some cases the user's location can be continuously provided to a third party, but in some other cases the user's location can only be provided to a third party when the user's leaves a designated area. For example, the device 1200 can only provide the user's location to a third party when the user is more than a specified distance from the user's residence. In cases where the user has Alzheimer's disease, dementia, or another similar condition, the ability to monitor the user's location can allow third parties to monitor the location of the user for the user's safety and intervene if the user moves to an unsafe or undesirable location.

Figure 13:
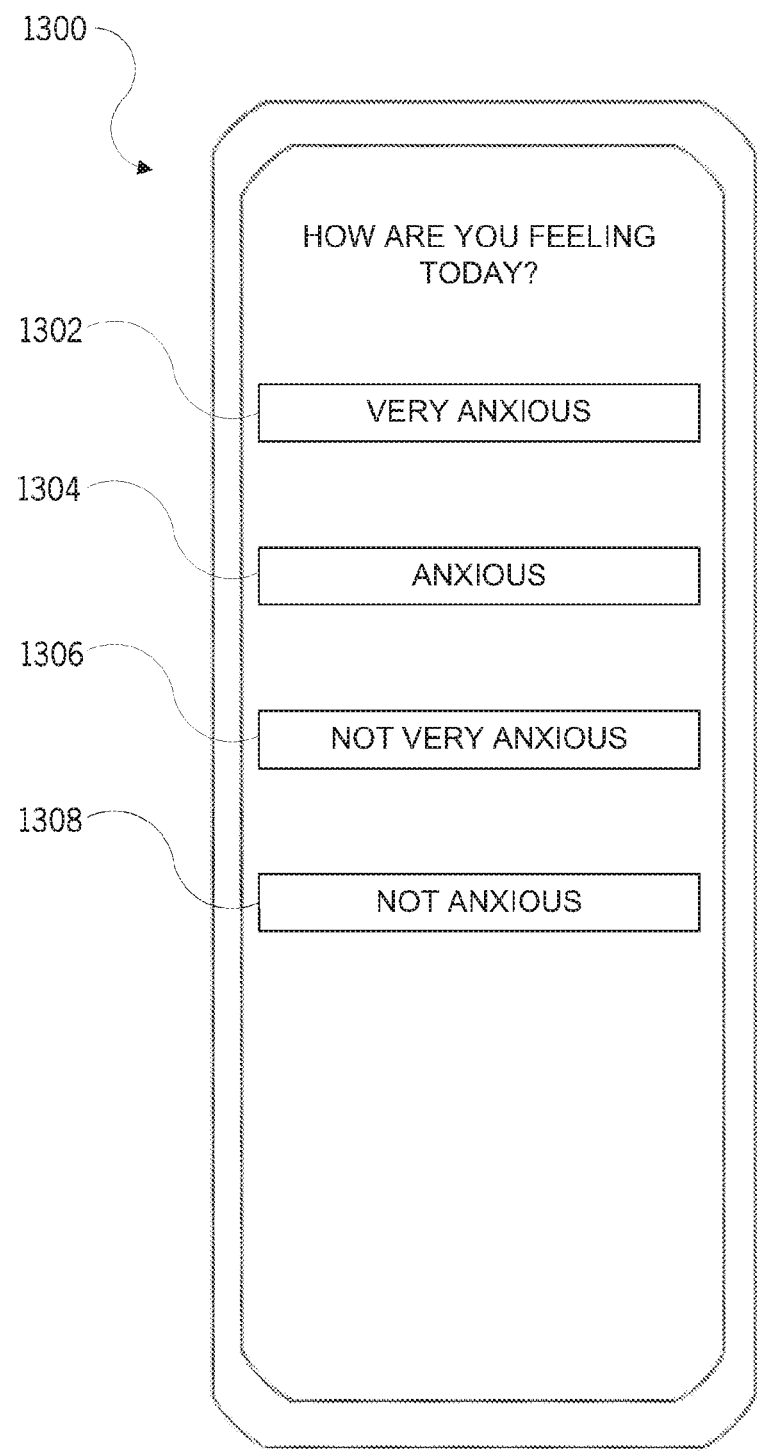
FIG. 13 depicts an example of a device for providing information and evaluating a prescribed device or service in accordance with aspects of the present disclosure.

FIG. 13 depicts an example of a device 1300 requesting information relating to the user's mental or physical health. In some examples, these questions can be accessed when the user accesses their user profile. In other examples, these questions can be presented to the user automatically based on the time of day or other types of triggers. For example, a request for a user's level of anxiety can be asked at predetermined times throughout the day. In some cases, requests for information can be received in the evenings where information about the user's health throughout the day can be requested at a single time of the day. In some cases, the user can have the option to select when some or all of the information is requested. In some cases, the questions presented to the user can be written by, selected by, or otherwise determined by the user's prescribing physician or another such medical professional. In this way, the user's doctor can be able to solicit specific information from the user about their experience in order to more fully inform any evaluation or modifications to a product, service, or plan used by the user.

The requests can be presented with multiple options for responding. In this case, the user can press a touch screen button that most appropriately reflects the user's experience. In this example, the user is presented a "very anxious" button 1302, an "anxious" button 1304, a "not very anxious" button 1306, and a "not anxious" button 1308. In other examples, more or fewer buttons can be presented to the user. In some cases, different type of moods, experiences, emotions, or other feelings can be described on the response buttons. In one example, the buttons can be depicted with an image of faces that reflect different types of user experiences. In other examples, word and images are presented together on the button. Further, the response mechanism can include another type of mechanism to communicate the user's answers. For example, the device can present the user with an open text field to describe his or her experience. In another example, the user can have an option to audibly speak his or her responses, or record a video message. In yet another embodiment, the user can be asked to rate his or her experience with a numeral value. In short, the examples described herein may not be limited to any particular type of presentation and/or responding mechanism. In some cases, a doctor, licensed medical professional a member of the medical team, or combinations thereof can determine the particular type of presentation and/or responding mechanism.

Figure 14:
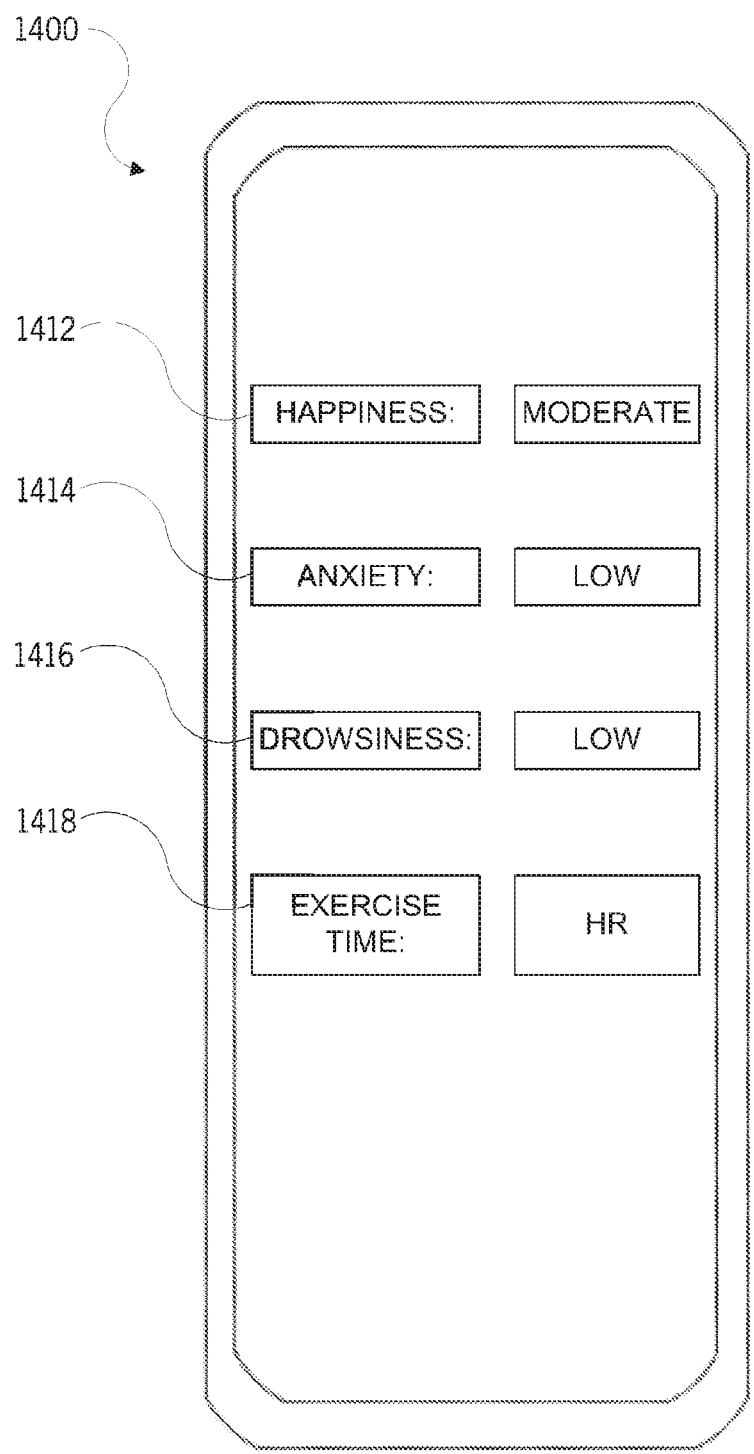
FIG. 14 depicts an example of a device for providing information and evaluating a prescribed device or service in accordance with aspects of the present disclosure.

FIG. 14 depicts an example of a device 1400 presenting an example of a summary of different types of questions requested from the user. In this example, the types of information requested can include a happiness field 1402, a level of anxiety field 1404, a level of drowsiness field 1406, a time spent exercising field 1408, another type of field, or combinations thereof.

In some cases, the device 1400 requests information from the user on a daily basis. In some examples, the same type of information is requested every day. In some examples, the same type of information can be requested one or more times per day. In other examples, different types of questions are presented on different days or at different times on the same day. Asking different questions over a spread of time, such as days, hours, or weeks can allow a doctor, licensed medical professional, member of the medical team, or combinations thereof to get more information requested without overburdening the user with information requests each day and still allowing the device to gather information at a useful sampling rate.

Additionally, the device 1400 can present the responses received from the user. In this example, the response field 1412 indicates that the user had a moderate level of happiness, response field 1414 indicates that the user has a low level of anxiety, response field 1416 indicates that the user had a low level of drowsiness, and response field 1418 indicates that the user spent 1 hour exercising. In some examples, the summary represents the responses that the user provided on a particular day. In some cases, the particular day is the same day that the responses were received. In some embodiments, the user can have an option of selecting a previous day to review the responses. The summary can represent an average or an aggregated amount of responses.

In some embodiments, a summary can be automatically generated from data collected from the user and can be presented to the user for review, confirmation, or other purposes. In some cases the device 1400 can be connected to one or more sensors that automatically collected data from the user and relay the data to the device 1400. For example, in some cases a user's contact lens can include one or more sensors to collect user data, such as physiological data, other data, or combinations thereof. The data collected by the one or more sensors can be transmitted or otherwise provided to the device 1400, for example via a wireless network. Data collected by the one or more sensors can be automatically provided to the device 1400, for example after a predetermined duration or after a predetermined condition is met. The user can then be presented with a summary of the collected data on device 1400 before, during, or after the data can be provided to the user's doctor, licensed medical professional a member of the medical team, or combinations thereof. In some cases, however, the data can be provided to the user's doctor, licensed medical professional, member of the medical team, or combinations thereof without being presented to the user.

Figure 15:
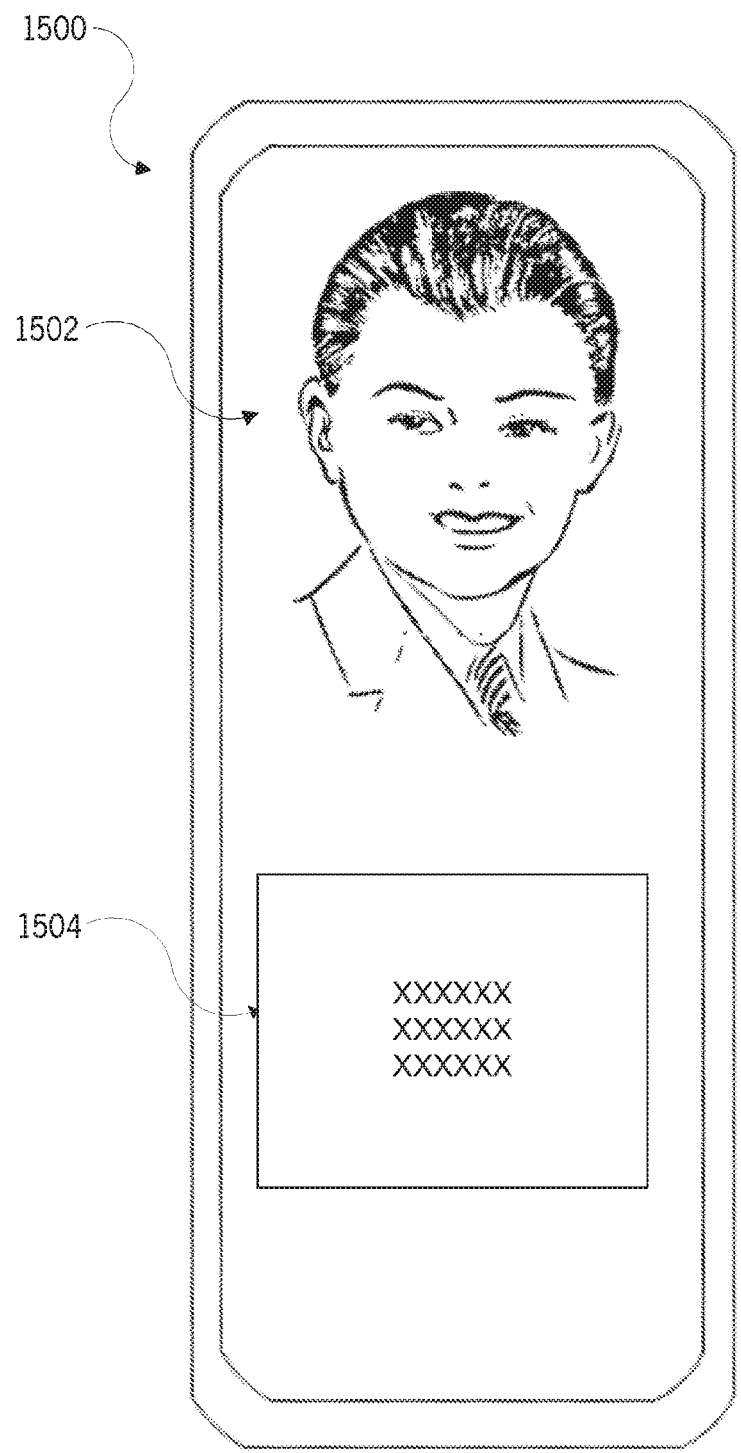
FIG. 15 depicts an example of a device for providing information and evaluating a prescribed device or service in accordance with aspects of the present disclosure.

FIG. 15 depicts an example of a device 1500 presenting information from a doctor, licensed medical professional, member of the medical team, or combinations thereof to the user by the device's display 1502. The device 1500 can present information from the doctor or another person to the user in response to information provided by the user, such as a user's responses to specific questions as described herein. The information 1504 provided to the user can be revised instructions regarding a product or service that the user is prescribed, further information concerning the product or service, instructions or revisions to a treatment plan for the user, or the like. In this particular example, the information 1504 provided by the doctor to the user is a modification to the dosage of a medications the user has been prescribed. In some examples, the information 1504 provided by the doctor can be selected from a preset list of responses, or can be written or otherwise decided by the doctor. In some cases, the information 1504 can include an audio and/or video message. In some examples, the information 1504 can include a video recording of the doctor. However, in some other examples the information 1504 can include, for example, an animated avatar of the doctor providing an audio message to the user. The audio message to the user can be generated from a pre-recorded set of responses, can be generated by a processor evaluating a set of inputs or data points collected by the system, or via another system or method.

Figure 16:
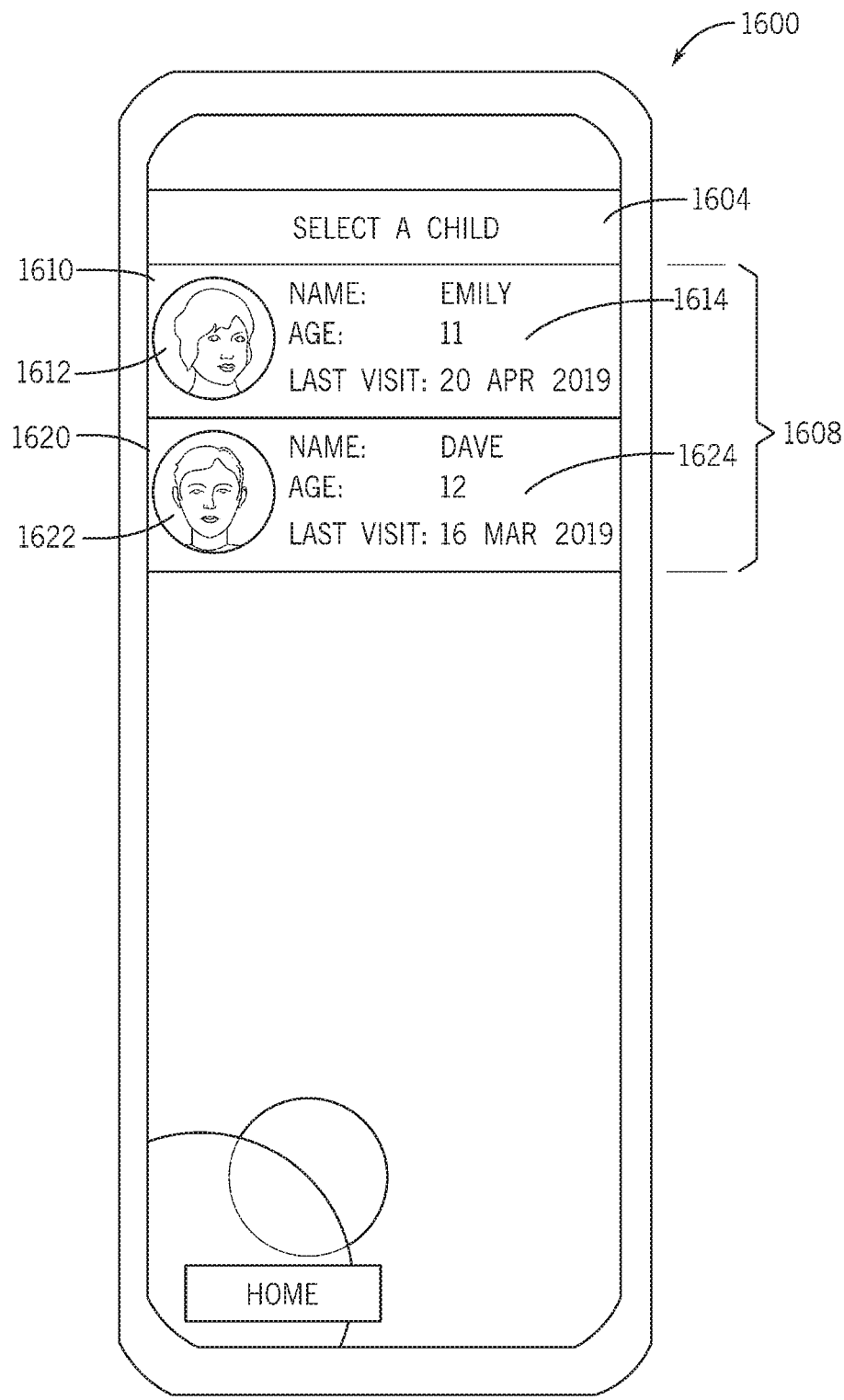
FIG. 16 depicts an example of a device for providing information and evaluating a prescribed device or service in accordance with aspects of the present disclosure.

FIG. 16 depicts an example of a device for providing information and evaluating a prescribed device or service in accordance with aspects of the present disclosure. In the example of FIG. 16, a device 1600 is shown including an example of an user interface for a primary user. The primary user can be a parent, such as the primary user 206 of FIG. 2. The user interface for the primary user can allow the primary user to view and access information associated with multiple secondary users, such the secondary user 208 of FIG. 2. In the non-limiting example of FIG. 2, a banner 1604 is shown including information for the primary user associated with the secondary users. For example, the banner 1604 could prompt the primary user to "Select a Child", with further details of the children of the primary user listed below in a summary region 1608.

The summary region 1608 can provide a summary of information for each of the secondary users associated with the primary user. The primary user can view the summary information as needed, and select a particular one of the secondary users for further information or options associated with evaluation of the prescribed optical device of the secondary user. In the example of FIG. 16, the summary region 1608 includes a first secondary user profile 1610, and a second secondary user profile 1620. The first secondary user profile 1610 can include an image 1612 and summary data 1614. The second secondary user profile 1620 can include an image 1622 and summary data 1624. While many options are possible, the summary data for the first and second secondary user profiles 1610, 1620 can include a name field, an age field, and a last visit field. In other cases, more or less information can be provided in the summary. The primary user can select the first or second secondary user profile 1610, 1620 in order to view further information pertaining the prescribed optical device for the given user.

Figure 17A:
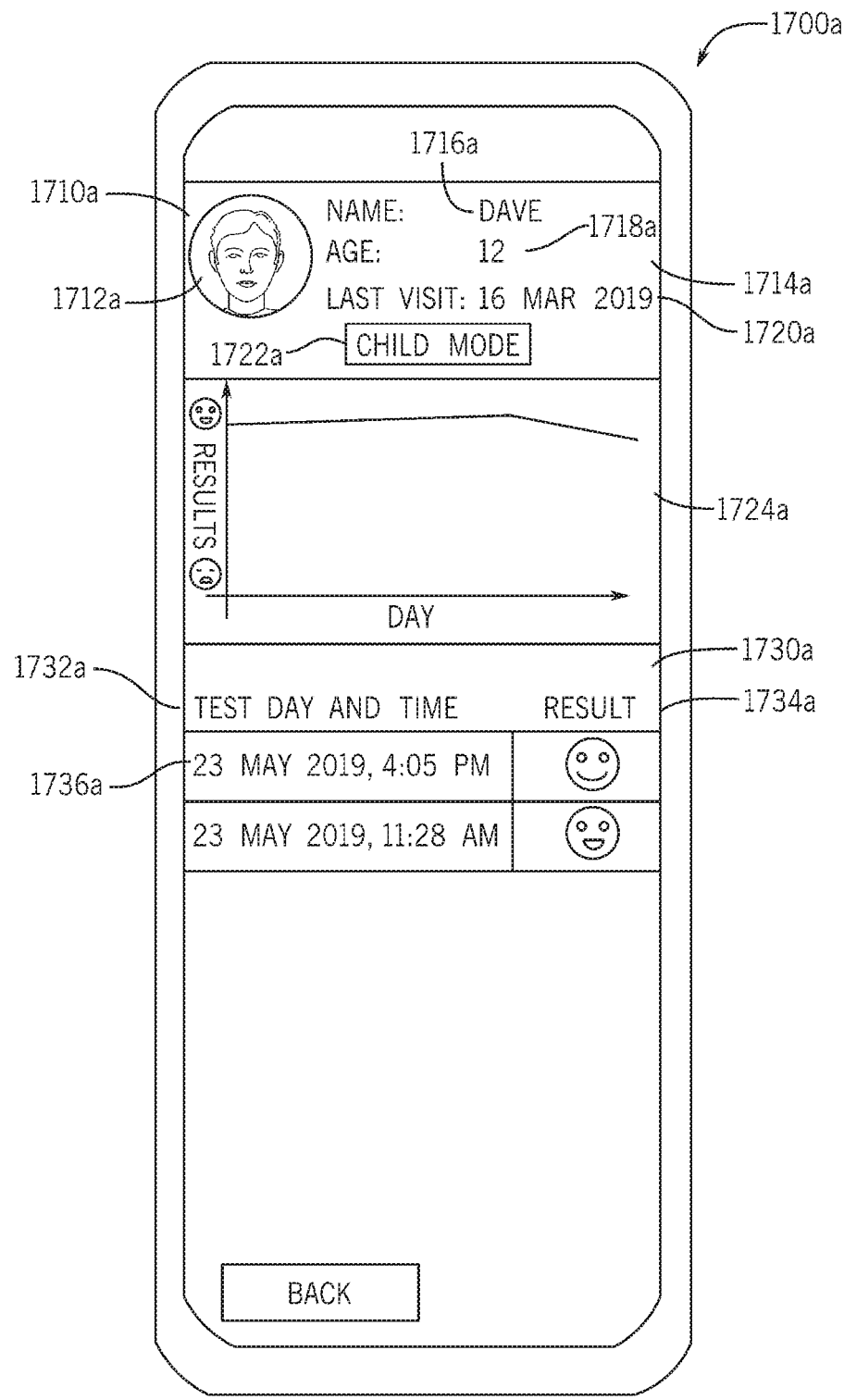
FIG. 17A depicts an example of a device for providing information and evaluating a prescribed device or service in accordance with aspects of the present disclosure.

FIG. 17A depicts an example of a device for providing information and evaluating a prescribed device or service in accordance with aspects of the present disclosure. In the example of FIG. 17A, a device 1700a is shown including an example of a user interface for the primary user, when a first secondary user profile is selected (e.g., the first secondary user profile 1610 of FIG. 16). In the example, of FIG. 17A, The first secondary user profile is illustrated with a secondary user profile 1710a. The secondary user profile 1710a can include an image 1712a and summary data 1714a. The summary data 1710a can includes a name field 1716a, an age field 1718a, and a last visit field 1720a.

The device 1700a also provides the primary user with an option to enter a "child mode" for the user associated with the secondary user profile 1710a. The child mode, such as that shown in the devices of FIGS. 18A-23C, can present a condensed, age-appropriate set of information and experiences to the user. In this regard, the device 1700a can be associated with the child upon receiving input at a secondary user transition button 1722a.

The device 1700a can also present other information to the primary user, tailored to the primary user. For example, the primary user can be a parent who desires to view the progress of the secondary user (child) over a period of time. In this regard, the device 1700a includes a graph 1724a that can show the results of the secondary user over a period of time. The device 1700a can further include a table 1732a which can also provide information associated with the secondary use over a period of time. In one instance, the table 1732a can show a history graphic 1736a and a results graphic 1734a associated with the use and/or evaluation of prescribed optical device for the secondary user.

Figure 17B:
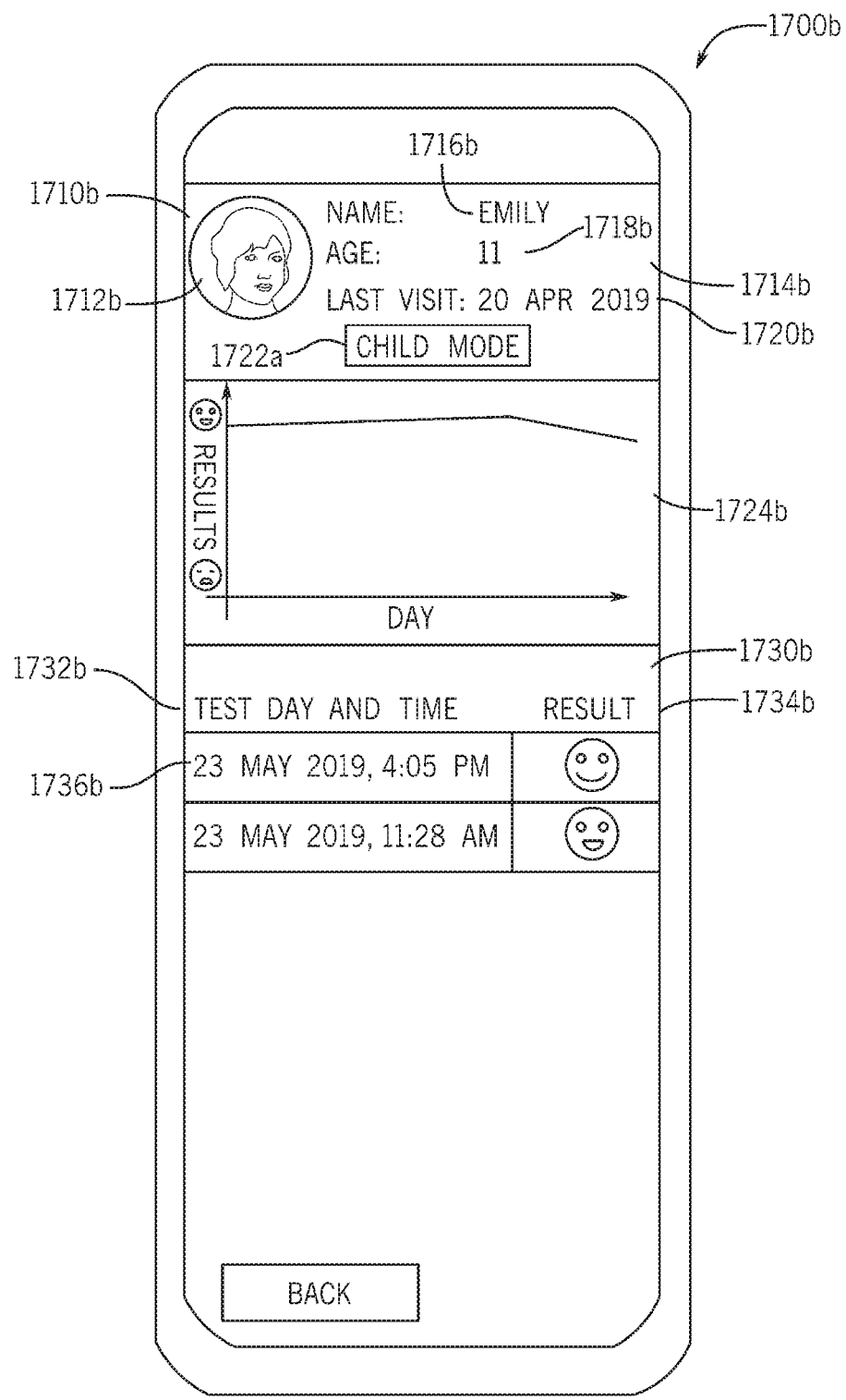
FIG. 17B depicts an example of a device for providing information and evaluating a prescribed device or service in accordance with aspects of the present disclosure.

FIG. 17B depicts an example of a device for providing information and evaluating a prescribed device or service in accordance with aspects of the present disclosure. In the example of FIG. 17B, a device 1700b is shown including an example of a user interface for the primary user, when a second secondary user profile is selected (e.g., the second secondary user profile 1620 of FIG. 16). In the example, of FIG. 17B, The second secondary user profile is illustrated with a secondary user profile 1710b. The secondary user profile 1710b can include an image 1712b and summary data 1714b. The summary data 1710b can includes a name field 1716b, an age field 1718b, and a last visit field 1720b.

The device 1700b also provides the primary user with an option to enter a "child mode" for the user associated with the secondary user profile 1710b. The child mode, such as that shown in the devices of FIGS. 18A-23C, can present a condensed, age-appropriate set of information and experiences to the user. In this regard, the device 1700b can be associated with the child upon receiving input at a secondary user transition button 1722b.

The device 1700b can also present other information to the primary user, tailored to the primary user. For example, the primary user can be a parent who desires to view the progress of the secondary user (child) over a period of time. In this regard, the device 1700b includes a graph 1724b that can show the results of the secondary user over a period of time. The device 1700b can further include a table 1732b which can also provide information associated with the secondary use over a period of time. In one instance, the table 1732b can show a history graphic 1736b and a results graphic 1734b associated with the use and/or evaluation of prescribed optical device for the secondary user.

The systems and techniques described herein can be used to present information at a network device that is tailored or adapted to a user associated with the device (e.g., as associated via a facial recognition or retina scan process, as described in relation to FIG. 2). FIGS. 18A-23C depicts various devices depicting information directed to a secondary user or child. While many variations are possible and contemplated herein, the child mode generally provides information associated with the use and/or evaluation of the prescribed optical device in an age-appropriate format or context. As an example, information associated with the prescribed optical device for the secondary user can be presented with a first quantity of attributes when viewed by the primary user, and a second quantity of attributes when viewed by the secondary (child) user. The second quantity of attributes can be a condensed or age-adjusted version of the first quantity of attributes. As another example, information associated with the prescribed optical device for the secondary user can be presented as a textual depiction of attributes when viewed by the primary user, and a graphical depiction of attributes when viewed by the secondary user. The graphical depiction can be a visual representation of the visual depiction. As another example, information associated with the prescribed optical device for the secondary user can be presented as a history of interactions (e.g., compliance data) with the prescribed optical device when viewed by the primary user, and a representation of rewards based on the history of interactions with the prescribed optical device. In other cases, other variations are possible and contemplated herein.

Figure 18A:
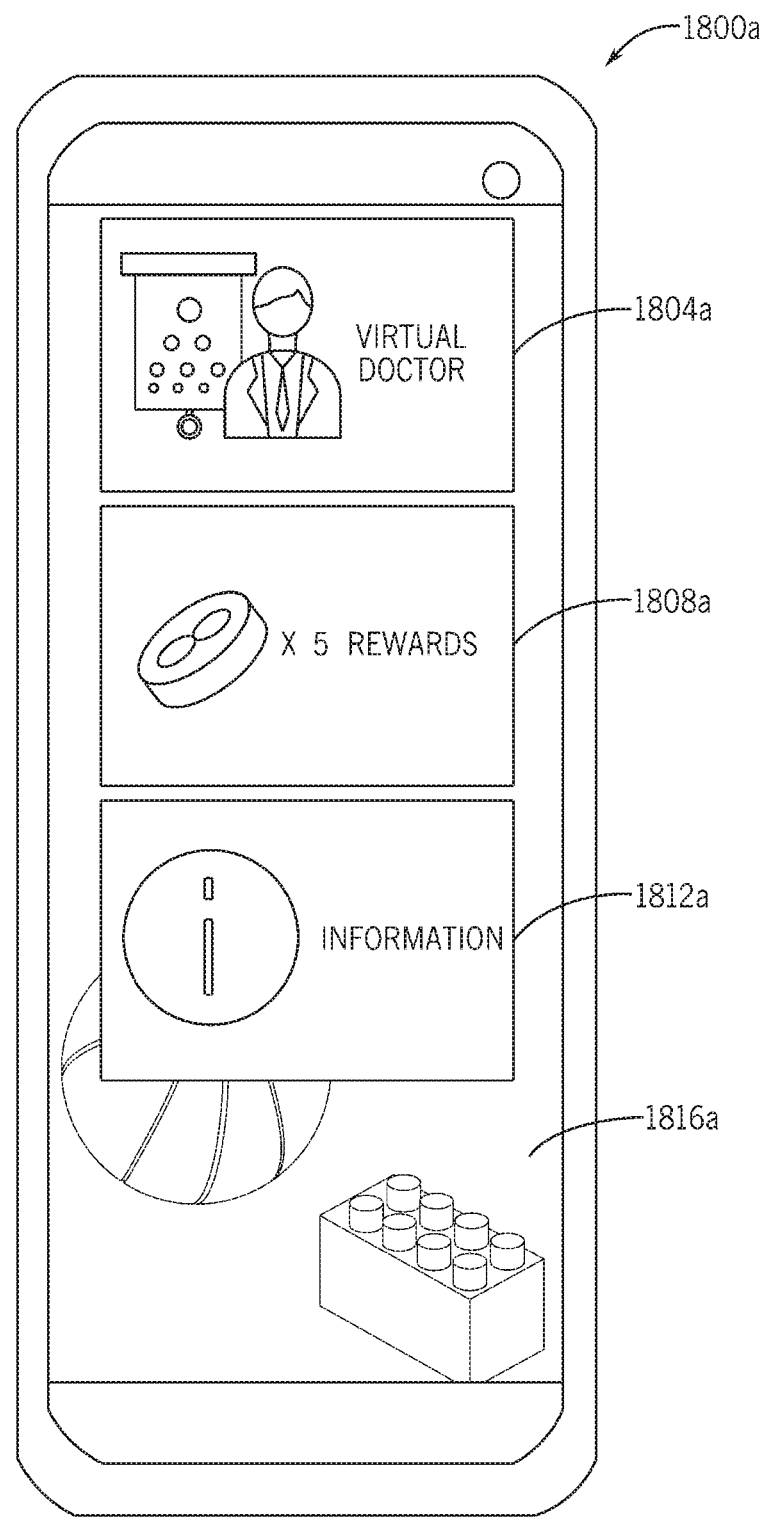
FIG. 18A depicts an example of a device for providing information and evaluating a prescribed device or service in accordance with aspects of the present disclosure.

With reference to FIG. 18A, an example of a device for providing information and evaluating a prescribed device or service in accordance with aspects of the present disclosure is depicted. In the example, of FIG. 18A, a device 1800a is shown. The device 1800a can correspond to a first secondary user profile (e.g., the first secondary user profile 1610 of FIG. 16) in a "child mode". The child mode of FIG. 18A can present a variety of options and interactions to the first secondary user. For example, the device 1800a can include a virtual doctor button 1804a, a rewards button 1808a, and an information button 1812a. The virtual doctor button 1804a, the rewards button 1808a, and the information button 1812a can allow the first secondary user to access user interfaces associated with real-time medical provider advice, rewards for compliance and/or progression with the prescribed optical device, and general information (including feedback tailored to the first secondary user), are described in greater detail herein with respect to the devices of FIGS. 19-21. The device 1800a also includes a theme 1816a. The theme 1816a can be customizable by the first secondary user, and can help indicate the profile with which the network is presently associated.

Figure 18B:
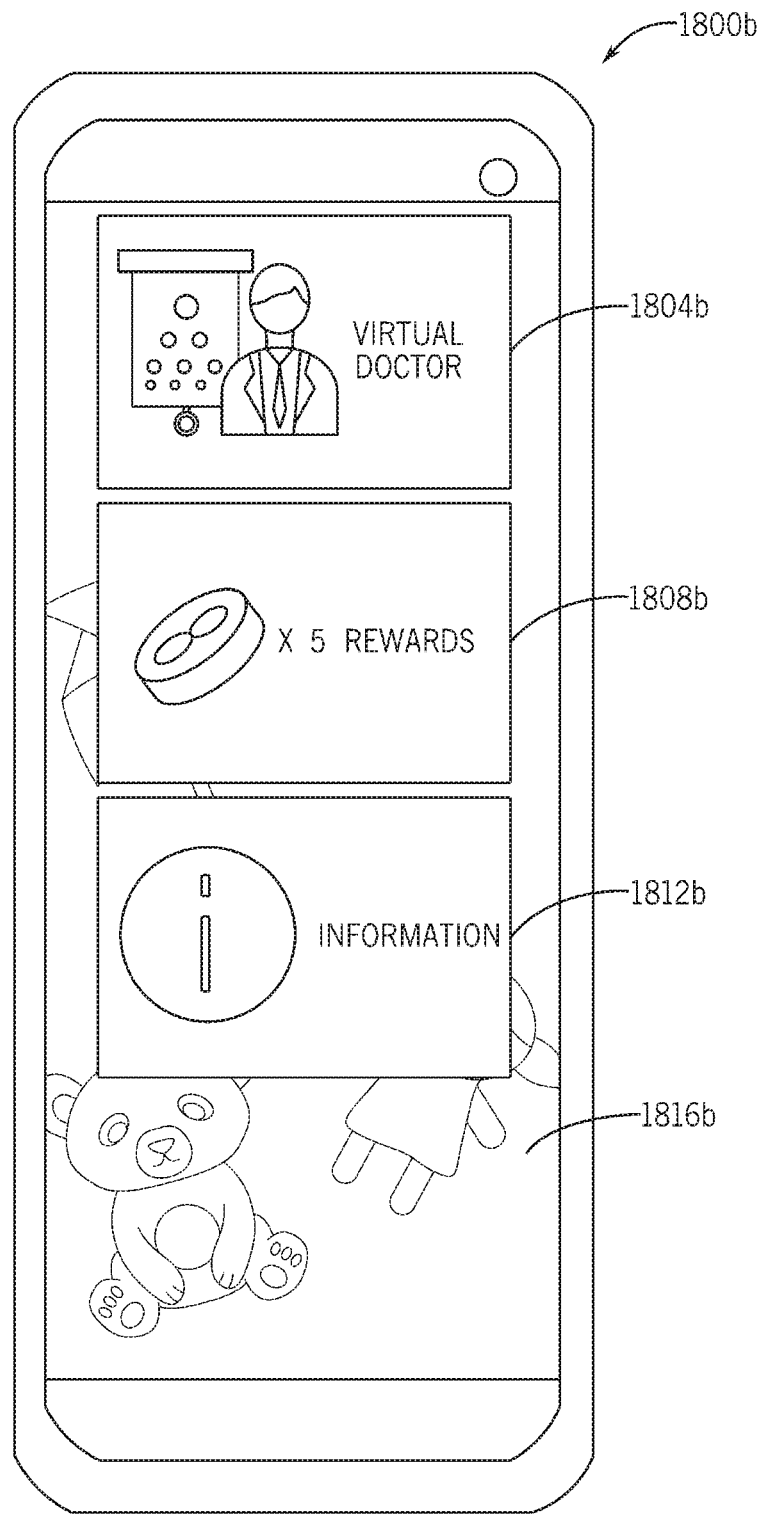
FIG. 18B depicts an example of a device for providing information and evaluating a prescribed device or service in accordance with aspects of the present disclosure.

With reference to FIG. 18B, an example of a device for providing information and evaluating a prescribed device or service in accordance with aspects of the present disclosure is depicted. In the example of FIG. 18B, a device 1800b is shown. The device 1800b can correspond to a first secondary user profile (e.g., the first secondary user profile 1610 of FIG. 16) in a "child mode". The child mode of FIG. 18B can present a variety of options and interactions to the first secondary user. For example, the device 1800b can include a virtual doctor button 1804b, a rewards button 1808b, and an information button 1812b. The virtual doctor button 1804b, the rewards button 1808b, and the information button 1812b can allow the first secondary user to access user interfaces associated with real-time medical provider advice, rewards for compliance and/or progression with the prescribed optical device, and general information (including feedback tailored to the first secondary user), are described in greater detail herein with respect to the devices of FIGS. 19-21. The device 1800b also includes a theme 1816b. The theme 1816b can be customizable by the first secondary user, and can help indicate the profile with which the network is presently associated.

Figure 19:
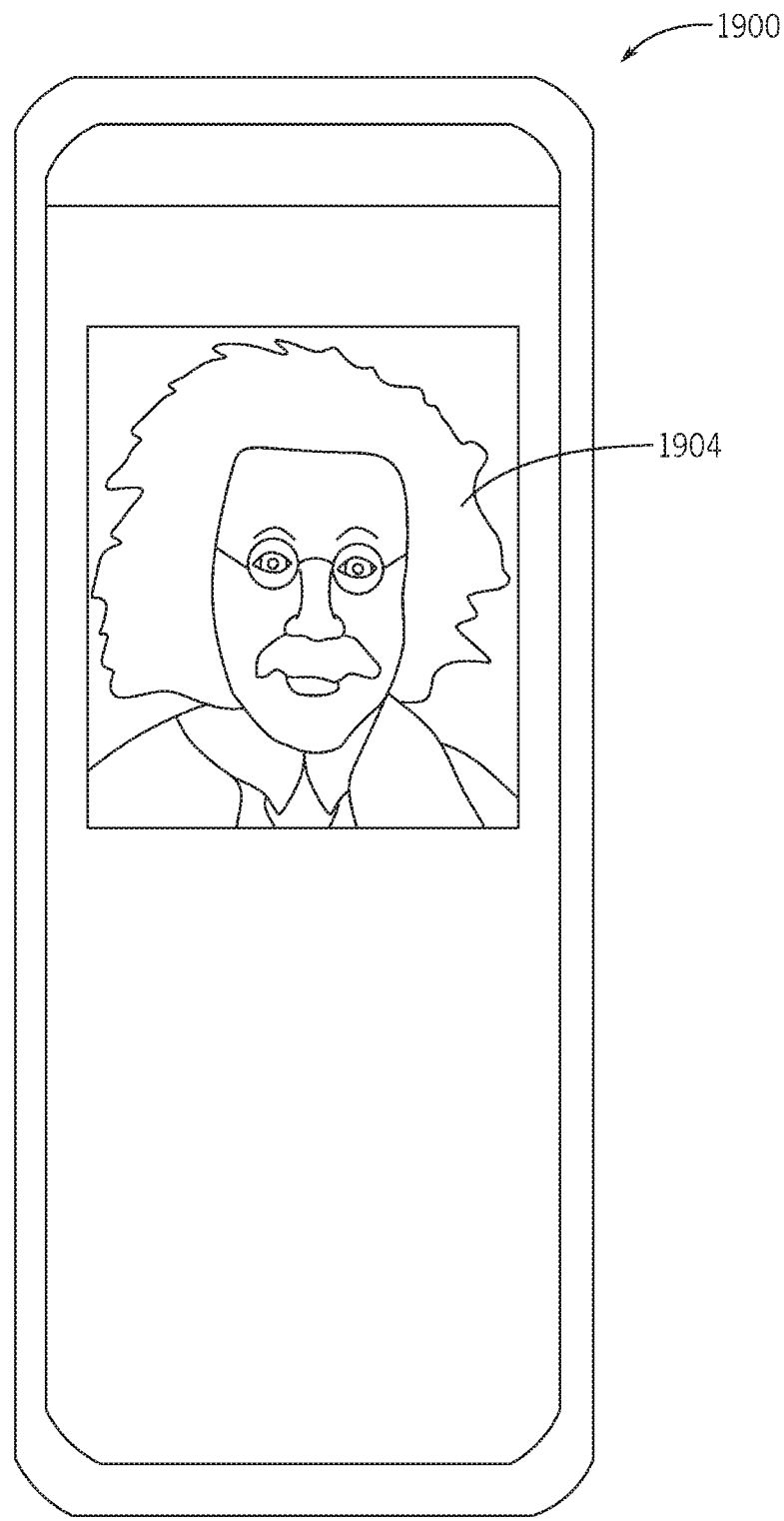
FIG. 19 depicts an example of a device for providing information and evaluating a prescribed device or service in accordance with aspects of the present disclosure.

With reference to FIG. 19, an example of a device for providing information and evaluating a prescribed device or service in accordance with aspects of the present disclosure is depicted. In the example of FIG. 19, a device 1900 is shown including information associated with a digital or virtual doctor. In this regard, the device 1900 is shown as including a virtual doctor icon 1904. The virtual doctor icon 1904 can provide an interface for receiving input from the secondary (child) user, and subsequently providing medical advice. In this regard, the device 1900 can functional substantially analogous to the device 1500 of FIG. 15. Notwithstanding, the device 1900 can be adapted for the secondary user, and thus the virtual doctor icon 1904 can be more graphical, in certain embodiments, as may be appropriate for the child-specific application.

Figure 20:
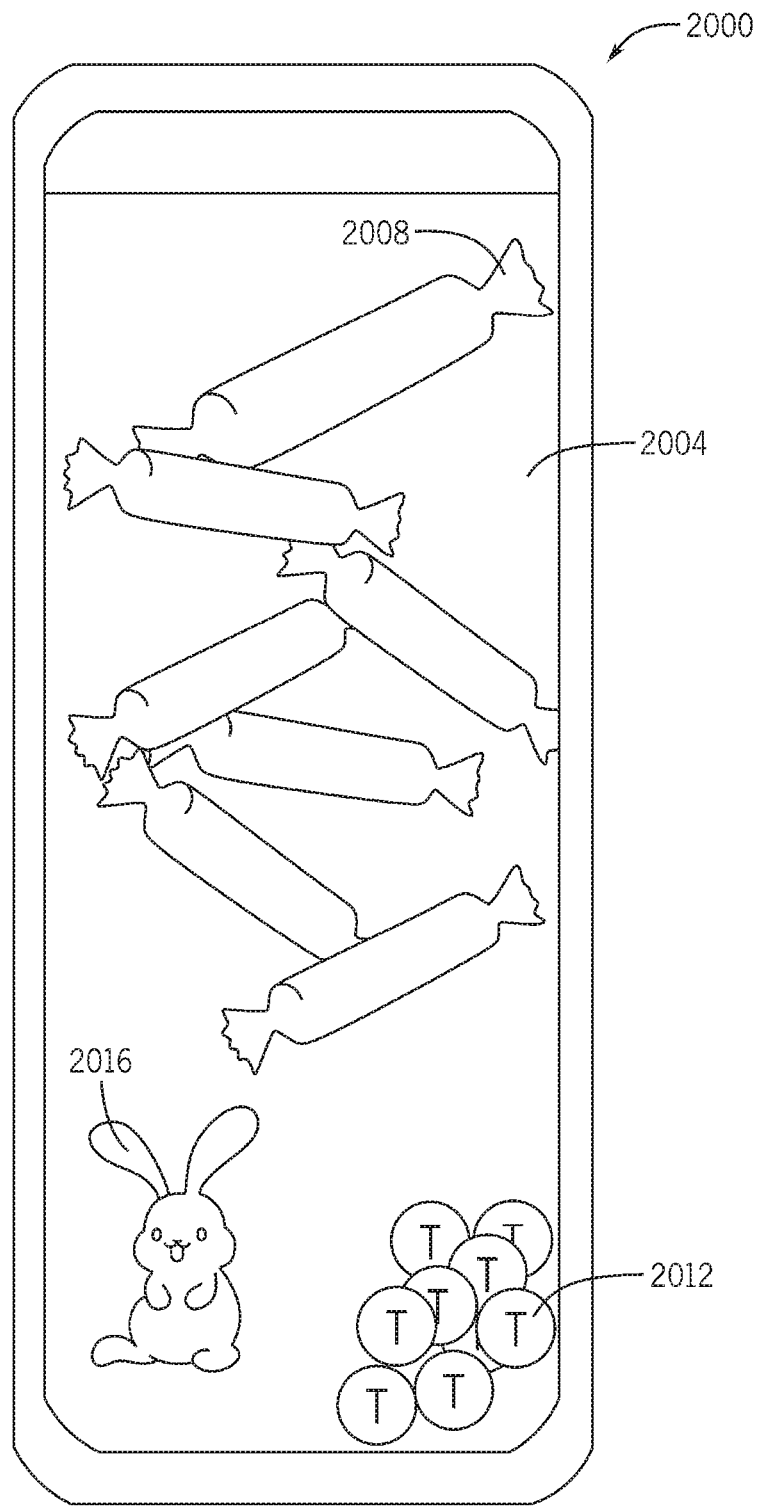
FIG. 20 depicts an example of a device for providing information and evaluating a prescribed device or service in accordance with aspects of the present disclosure.

With reference to FIG. 20, an example of a device for providing information and evaluating a prescribed device or service in accordance with aspects of the present disclosure is depicted. In the example of FIG. 20, a device 2000 is shown including information associated with rewards. For example, the device 2000 can include a rewards interface having a first rewards icon 2008, a second rewards icon 2012, and a third rewards icon 2016. In other cases, other rewards icons can be provided by the device 2000. The rewards interface 2004 can generally provide the secondary (child) user with an incentive to participate in the evaluation of the prescribed optical device. For example, the evaluation of the prescribed optical device can be facilitated in response to the child providing information regarding a comfort level of a contact lens. Upon providing this information, the systems and techniques described herein an cause the device 1900 to display the rewards icons 2008, 2012, 2016. Rewards can also be provided in response to using the prescribed optical device, as prescribed, or based on other characteristics or factors. The reward icons 2008, 2012, 2016 can in certain circumstances be representative of actual prizes that are redeemable, whereas in other cases the rewards are digital, and thus can be used and enjoyed in a digital context. In the same of FIG. 20, the rewards icon 2008 include a depiction of candy, the rewards icon 2012 includes a depiction of tokens, and the rewards icon 2016 includes a depiction of a plush rabbit. It will be appreciated, however, that these are shown for purposes of example, and that in other cases, other rewards can be provided.

Figure 21:
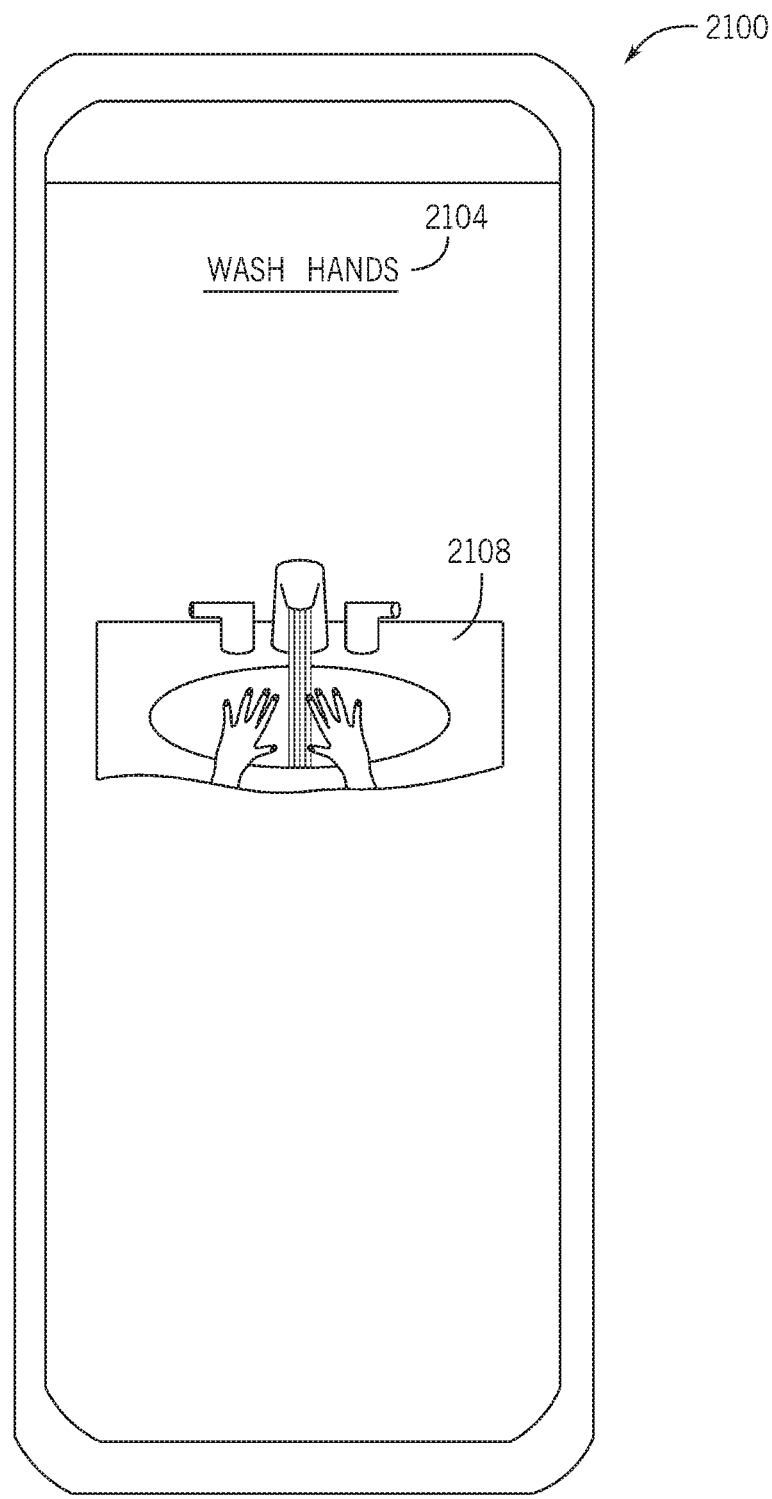
FIG. 21 depicts an example of a device for providing information and evaluating a prescribed device or service in accordance with aspects of the present disclosure.

With reference to FIG. 21, an example of a device for providing information and evaluating a prescribed device or service in accordance with aspects of the present disclosure is depicted. In the example of FIG. 21, a device 2100 is shown including information associated with information messages for the prescribed optical device. The information messages can cover a variety of topics and can be tailored to the particulars of the user profile. For example, where a user reports certain levels of contact lens discomfort, the information message can be adapted to provide information associated with proper techniques for associating a contact lens with an eye. In other cases, the message can be more general, such as that shown in FIG. 21. In particular, an informational message 2104 is shown that instructs the user to "Wash Hands". An icon 2108 can also be provided with the information message 2108, which can also provide information to the user for satisfying the directive of the information message.

Figure 22:
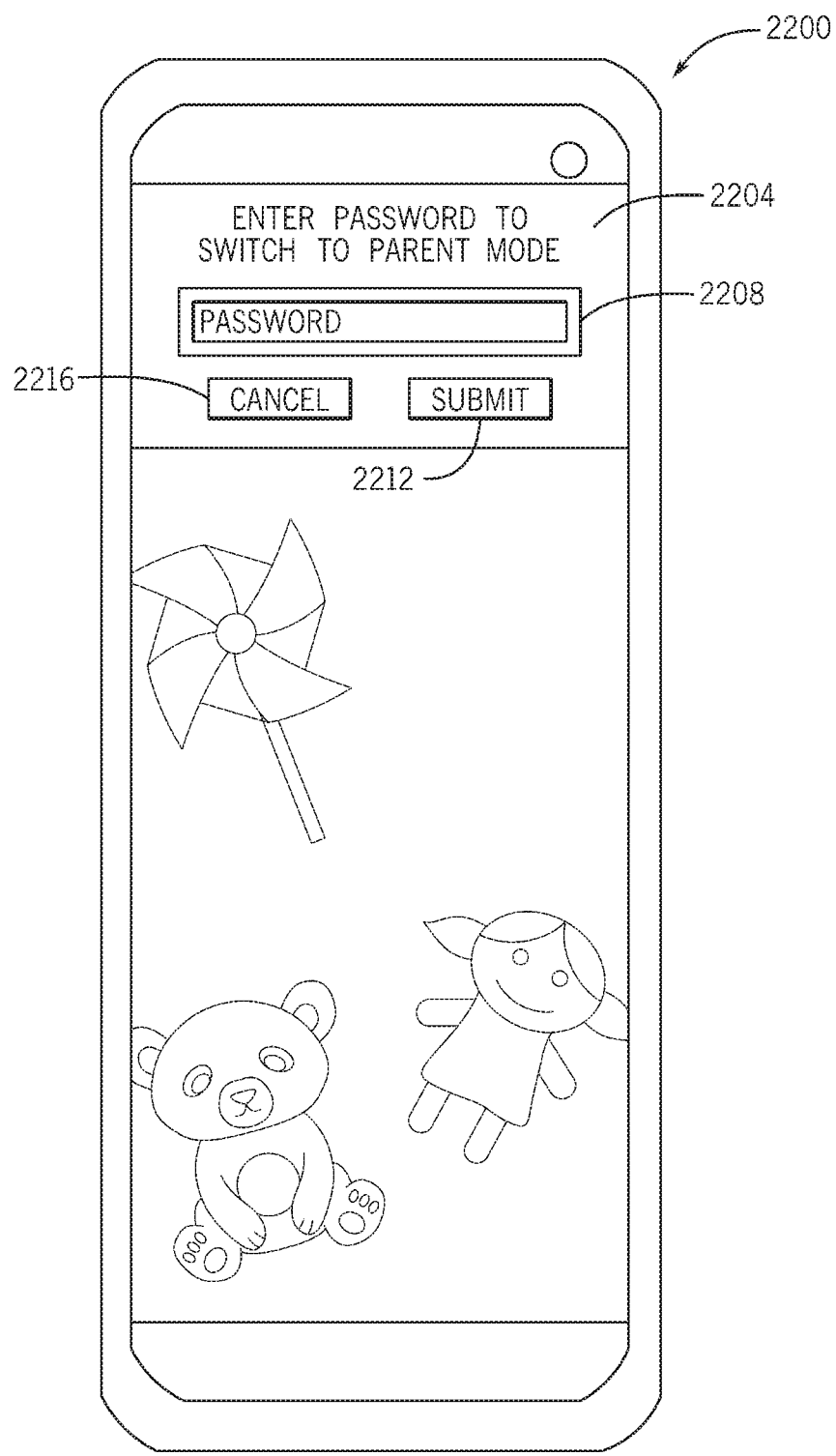
FIG. 22 depicts an example of a device for providing information and evaluating a prescribed device or service in accordance with aspects of the present disclosure.

With reference to FIG. 22, an example of a device for providing information and evaluating a prescribed device or service in accordance with aspects of the present disclosure is disclosed. In the example of FIG. 22, a device 220 is shown including information that allows the device 2000 to transition from a child mode, such as that of FIGS. 19-21, and to the parent mode, such as that of FIGS. 16-17B. The device 2200 is shown as including a prompt 2204. The prompt indicates to the user that a password can entered to switch the device 2200 into the parent mode. The device 2200 is shown as including a password field 2208. The password field 2208 can allow the device to receive on or more input form the user, that can be used to associate the network device the primary (parent) user, as one example. A submit button 2212 is also provided so that input in the password filed 2208 is analyzed. A cancel button 2216 is also provided, allowing the user to return to child mode, or otherwise exit the user interface shown in FIG. 22.

As described herein, the user interface that is presented at the network device can be modified based on one or more characteristics of the user. For example, the network device can display a first user interface to a secondary (child) user. As the child progresses, e.g. in age, the network device can subsequently display a second user interface to a the secondary user. The second user interface can include modified information as compared with the first user interface, including information that is adjusted based on age-appropriate messages and controls.

More generally, the network device can adapt the user interface based on a progression characteristic of the user. The systems and techniques herein can operate to compute a progression characteristic, and when the progression characteristic satisfies a boundary condition, cause the network device to generate the second user interface having the modified information. The progression characteristic can be computed in a variety of manners, and modified based on metrics and parameters of interest, which can optionally be directed or modified by the primary (parent) user. In some embodiments, the progression characteristic can be computed using one or more of an age of the user, a compliance history of the user, a treatment progress history of the user, or a medical history of the user. The age of the user, the compliance history of the user, the treatment progress history of the user, the medical history of the user, and/or other characteristics can be determined, at least in part, using sensors of the network device. In certain embodiments, the sensors can include sensors that are adapted to capture one or more images for one or both of a facial recognition process or a retina scan process. In this regard, the network can detect changes in the user, and update the user interface accordingly, such as updating the user interface progressively as the user ages, and/or completes certain aspects of a treatment, as illustrative examples.

The boundary condition can be associated with a milestone for a combination of one or more of the age of the user, the compliance history of the user, the treatment progress of the user, or the medical history of the user. The milestone can therefore be indicative of a progression-based appropriateness of the modified information for the user. Thus when the computed progression characteristic satisfies the boundary condition, the system and techniques herein can cause the second user interface to be displayed with the modified information, tailored based on the progression-based appropriateness.

Figure 23A:
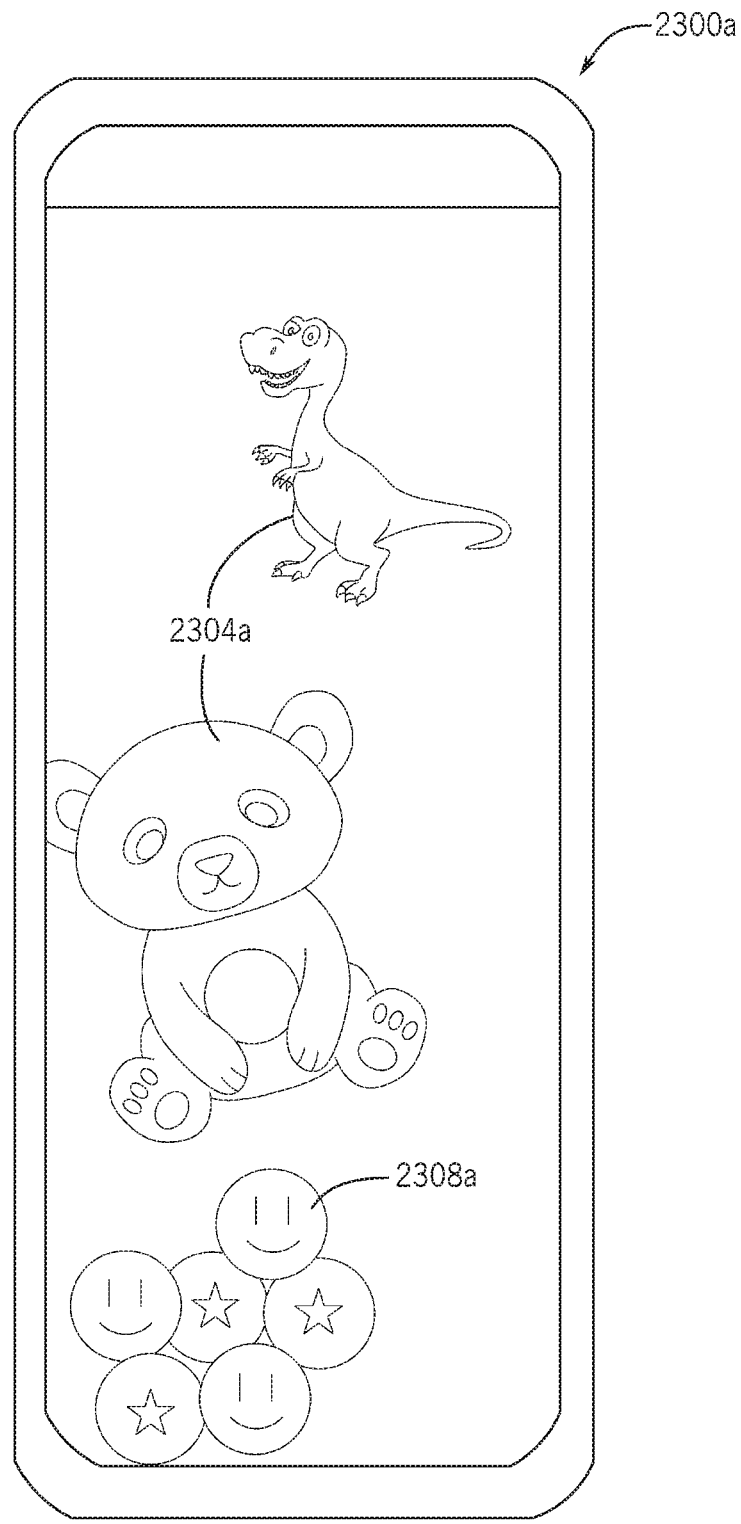
FIG. 23A depicts an example of a device for providing information and evaluating a prescribed device or service in accordance with aspects of the present disclosure.
Figure 23B:
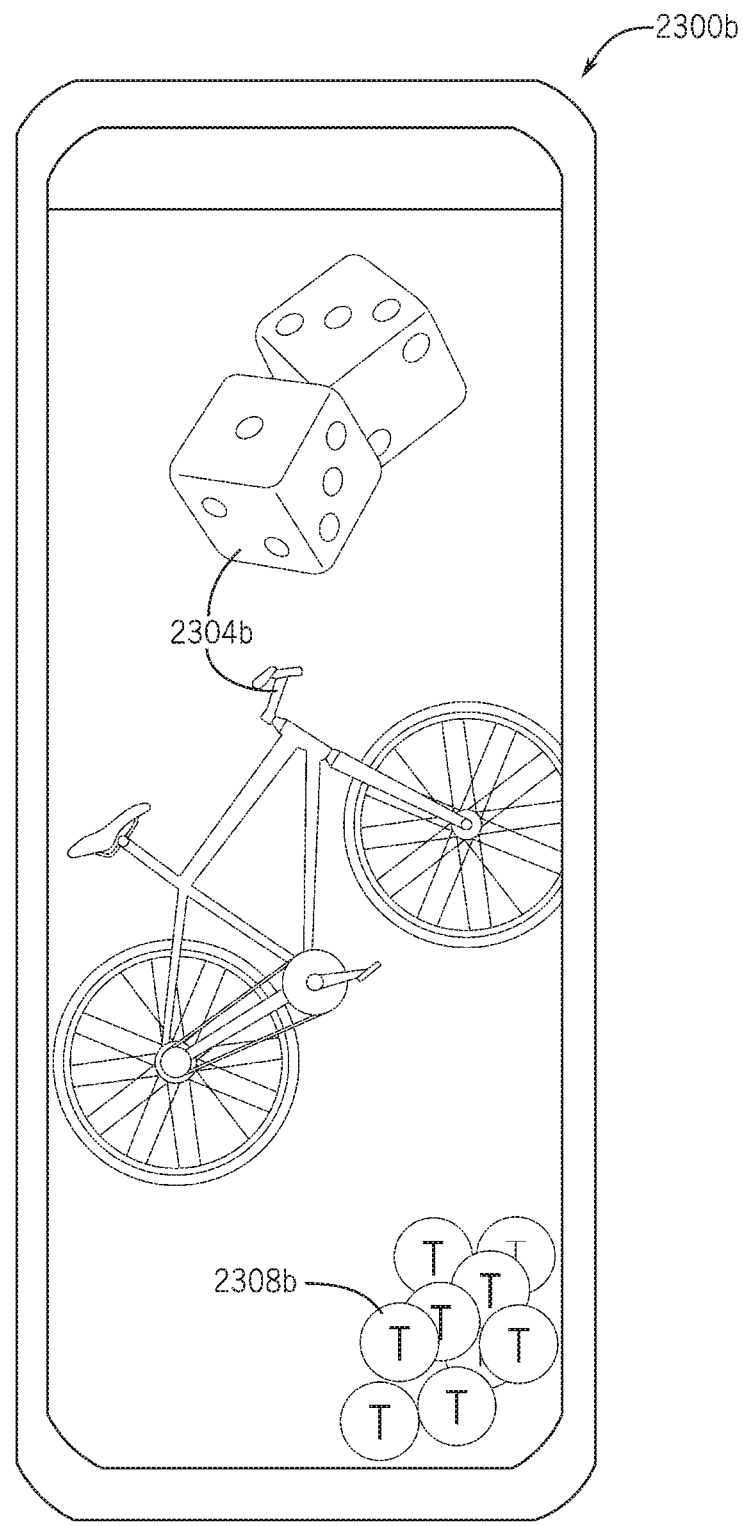
FIG. 23B depicts an example of a device for providing information and evaluating a prescribed device or service in accordance with aspects of the present disclosure.
Figure 23C:
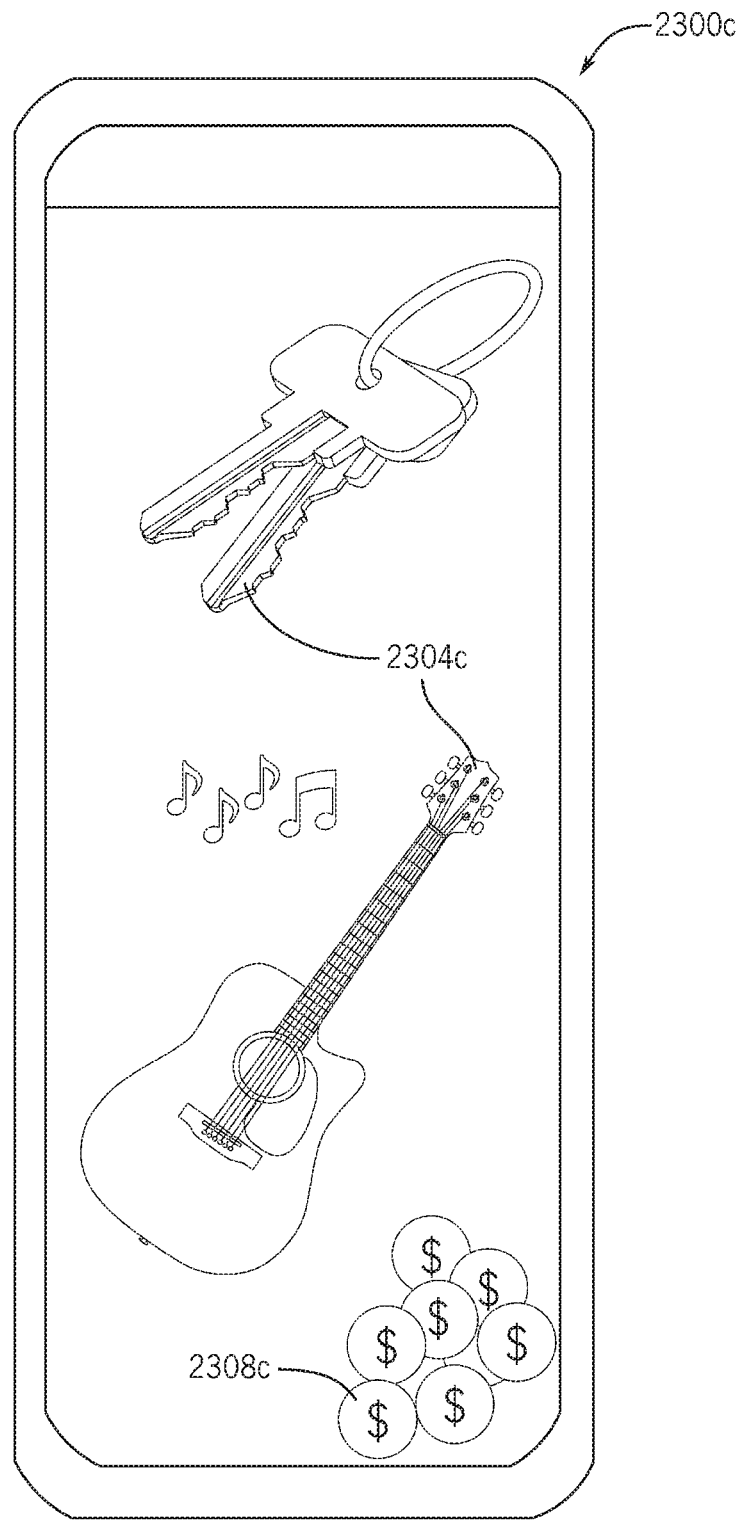
FIG. 23C depicts an example of a device for providing information and evaluating a prescribed device or service in accordance with aspects of the present disclosure.

FIGS. 23A-23C depict example devices for providing information and evaluating a prescribed device or service in accordance with aspects of the present disclosure. In particular, FIGS. 23A-23C show devices that include modifies user interfaces, as adjusted for progression-based appropriateness discussed above. With reference to FIG. 23A, a device 2300a is shown having a first rewards icon 2304a and a second rewards icon 2308a. The rewards icons 2304a, 2308a can be tailored, for example, for presentation to a younger child. With reference to FIG. 23B a device 2300b is shown having a modified first rewards icon 2304b and a modified second rewards icon 2308b. The modified first and second rewards icons 2304b, 2308b can be tailored, for example, for presentation to an older child. With reference to FIG. 23C, a device 2300c is shown having a further modified first rewards icon 2304c and a further modified second rewards icon 2308c. The further modified first and second rewards icons 2304b, 2308c can be tailored, for example, for presentation to a teenager.

The devices described herein, for example with respect to FIGS. 3-23C, serve to enhance communication between the user and a doctor, licensed medical professional, member of the medical team, or combinations thereof outside of scheduled visits between the user and the doctor. While a user can have an in-person visit with a doctor only infrequently, the doctor can nevertheless monitor the user's use of prescribed products or services, or a user's adherence to a treatment plan. The doctor can also make adjustments to the instructions provided to the user or to the user's treatment plan and can effectively and reliably communicate these adjustment or additional instructions via the devices described herein, without the need to schedule an in-person visit or phone call. Further, the personalize and interactive nature of the devices described herein, for example the use of an avatar to relay information to the user, can provide for enhanced user engagement, trust, and complete openness with the device and prescribed product, service, or treatment plan, thereby ensuring compliance of the user. It is expressly contemplated that any of the embodiments and devices described herein can be freely combined with one another to satisfy the particular needs of a user and/or doctor in relation to the evaluation and monitoring of one or more prescribed products, services, and treatment plans.

Figure 24:
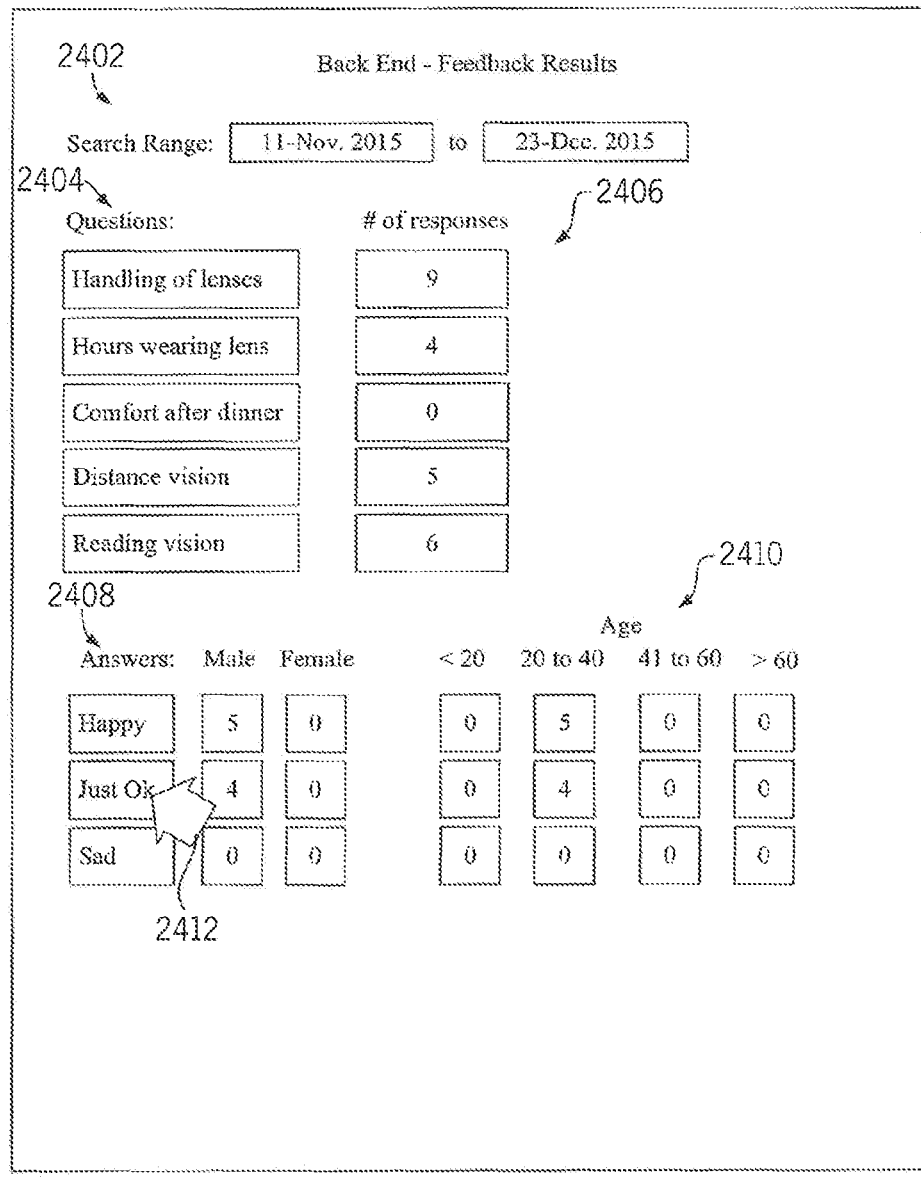
FIG. 24 depicts an example back-end system for evaluating a prescribed optical device in accordance with aspects of the present disclosure.

FIG. 24 presents an example of a back-end interface 2400 presenting feedback from a number of different users. This information can be available to all members of the distribution system or just selected members of the distribution system. In some cases, this data can be collected from the devices used by the user, and sent to at least one member of the distribution system. In some cases, the information is sent to a central database, and the members of the distribution system have access to the information.

In some cases, the information is raw information that has not been processed. In other examples, the information has been at least partially processed by the device used directly by the user, a server from which the device sent the information, a database manager, a remote device, a networked device, another type of device, or combinations thereof. The processed information can be aggregated information, averaged information, interpolated information, extrapolated information, categorized information, other types of information, or combinations thereof.

In this example, the results can be searchable by a date manager 2402. The date manager 2402 can include an option to input a range of dates to narrow the search results. Additionally, the types of questions 2404 that were requested of the user can also be presented in the display. The back-end interface 2400 can also present the number of responses 2406 that received from different users with the questions 2404.

In addition to the number of responses 2406, the user can have the option to drill down to a more detailed review of the responses from each user. In the depicted example, a table 2408 can present the types of responses in rows and user characteristics in columns. In this example, the columns can represent gender characteristics, age characteristics, nationality characteristics, other types of characteristics, or combinations thereof.

The members of the distribution system can review the information provided by the users through the back-end interface 2400. Based on this feedback, the members of the distribution system can choose to make changes to their individual processes or can respond to the information provided by one or more users. For example, a manufacturer can decide to use a different type of geometry in a contact lens, or a different type of material in a contact lens, or make some other changes to how the contact lens is manufactured. In addition to the information being available for members of the distribution system to analyze, algorithms and other processes can automatically scan and analyze the feedback from users. This analysis can include aggregating the information received from each of the users and identifying which of the responses are to be considered unsatisfactory ratings or other negative types of results. Each of the unsatisfactory ratings can be categorized into different types of ratings. For example, negative ratings that relate to dry eyes can be categorized into one group, and responses that deal with poor insertion of the contact lens into a user's eyes can be categorized into another group. When at least one of the categorized groups reaches a threshold, it can trigger a further analysis. Each of the different categories can have a different threshold number before such a response is triggered, or the number of threshold responses can be uniform through the different categories.

In one example when the threshold number is reached, a processor can cause the number of total responses to be compared to the unsatisfactory responses to determine the percentage of responses that are unsatisfactory within that category. In those cases where the unsatisfactory responses are a significant percentage of the total number of responses within that category, a message can be sent to a member of the distribution system to alert them of the high percentage of unsatisfactory ratings. In other cases, a message and another type of response can be generated automatically. For example, a response can include shutting down a portion of a manufacturing process, stopping all shipments of a particular type of product, recommending that a product be recalled, other responses, or combinations thereof.

A further level of analysis can include grouping the number of unsatisfactory responses with user characteristics. For example, the unsatisfactory ratings can be disproportionately higher among people of a certain gender, of a certain age, of a certain nationality, another common characteristic, or combinations thereof. By grouping the user characteristics, the root cause of the unsatisfactory results can be easier to identify.

Another layer of analysis can include looking at the characteristics of the products or services associated with the unsatisfactory ratings. For example a high percentage of contact lenses with a particular type of material can be associated with unsatisfactory ratings. In that type of situation, the system can recommend to the manufacturer to change the type of material. Conversely, if a particular type of contact lens material results in a high percentage of favorable responses from users, the system can recommend to the manufacturer or other member of the distribution system to incorporate that type of material in more future contact lenses. In another example, the geometry or shape of the contact lenses can also be analyzed in relation to the unsatisfactory responses to determine whether the lens' geometry is a contributing cause for some of the unsatisfactory responses.

In other situations, the unsatisfactory responses can be associated with factors that are not related to the manufacturing process. For example, if a lot of unsatisfactory responses are clustered around a particular date from a number of different users in the same geographic area, the system can look up the weather that was associated with that area for that particular day, the types of events that were going on that day, the type of holidays celebrated in that area that day, or look at other factors that can have affected user's contact lens wearing experience.

Figure 25:
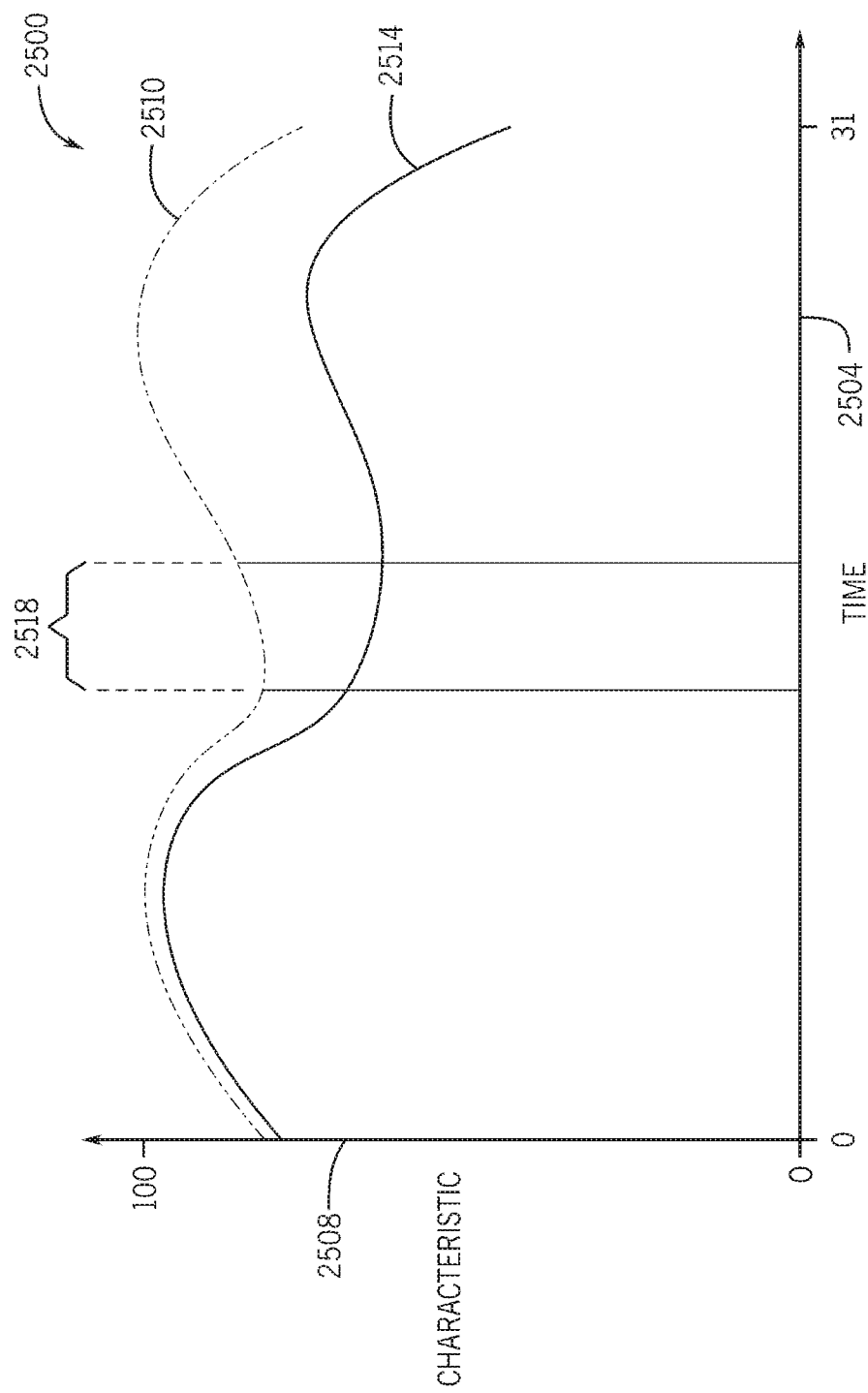
FIG. 25 depicts a chart illustrating a deviation between expected and record performance of a given characteristic over time.

FIG. 25 depicts a chart 2500 illustrating a deviation between expected and record performance of a given characteristic over time. The systems and methods of the present disclosure can be used to receive substantially real-time feedback related to the use of a prescribed optical device. The feedback can related to a variety of factors and characteristics, such as comfort. The systems and techniques of the present disclosure can also be used to analyze deviations from the substantially real-time feedback and an anticipated value of a given characteristic for a specified time period. In this regard, the deviation can be used by members of the distribution system to determine a corrective course of action, such as changing a type or size of contact lens where the user reports unsatisfactory levels of discomfort.

The chart 2500 illustrates the foregoing by depicting actual versus anticipated performance of a characteristic over time. Specifically, the chart 2500 includes a time axis 2504 and a characteristic axis 2508. The time axis 2504 can correspond to a specified time period, such as a month, and the characteristic axis 2508 can correspond to a percent satisfaction of the user with a given attribution of the prescribed optical device, such as comfort. FIG. 25 shows the chart 2500 including a first curve 2510 and a second curve 2514. The first curve 2510 can correspond to an anticipated performance of the characteristic, whereas the second curve 2514 can correspond to an actual or recorded performance of the characteristic (e.g., as recorded or documented via one or more of the network devices described herein). The chart 2500 also shows a period 2518 which may be selected in order to analyze the deviation between the first curve 2510 and the second curve 2514. The deviation within the period 2518 can be correlated with other factors in order to determine if one or more members of the distribution system can or be recommended to take certain corrective actions, including informing the user of different optical devices and types to improve the performance of the characteristic for a subsequent time period.

Figure 26:
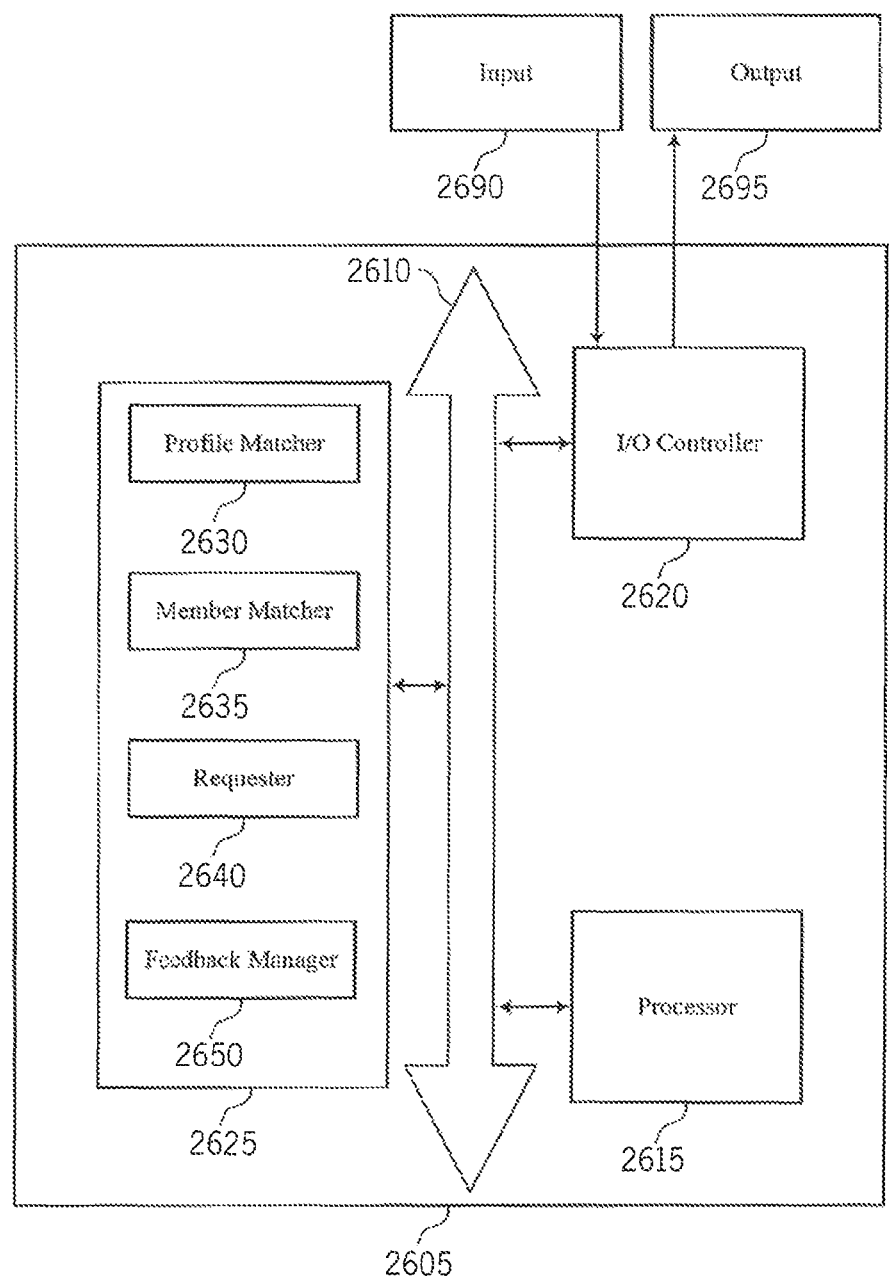
FIG. 26 depicts an example of a block diagram of an evaluation system in accordance with aspects of the present disclosure.

FIG. 26 shows a diagram of a system 2600 including a device 2605 that supports evaluating the user's experience with prescribed products or services in accordance with aspects of the present disclosure. Device 2605 can be an example of the device as described above, e.g., with reference to FIGS. 3-23C. Device 2605 can include components for bi-directional voice and data communications including components for transmitting and receiving communications, including processor 2615, I/O controller 2620, and memory 2625. These components can be in electronic communication via one or more busses (e.g., bus 2610). Memory 2625 can also include profile matcher 2630, member matcher 2635, requester 2640, and feedback manager 2650.

Processor 2615 can include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, processor 2615 can be configured to operate a memory array using a memory controller. In other cases, a memory controller can be integrated into processor 2615. Processor 2615 can be configured to execute computer-readable instructions stored in a memory to perform various functions (e.g., functions or tasks supporting the evaluation of prescribed products or services).

I/O controller 2620 can manage input and output signals for device 2605. I/O controller 2620 can also manage peripherals not integrated into device 2605. In some cases, I/O controller 2620 can represent a physical connection or port to an external peripheral. In some cases, I/O controller 2620 can utilize an operating system such as iOS®, ANDROID®, MS-DOS®, MS-WINDOWS®, OS/2®, UNIX®, LINUX®, or another known operating system. In other cases, I/O controller 2620 can represent or interact with a modem, a keyboard, a mouse, a touchscreen, or a similar device. In some cases, I/O controller 2620 can be implemented as part of a processor. In some cases, a user can interact with device 2605 via I/O controller 2620 or via hardware components controlled by I/O controller 2620. The I/O controller 2620 can be in communication with any appropriate input 2690 and any appropriate output 2695.

Memory 2625 can include random access memory (RAM) and read only memory (ROM). The memory 2625 can store computer-readable, computer-executable software including instructions that, when executed, cause the processor to perform various functions described herein. In some cases, the memory 2625 can contain, among other things, a basic input/output system (BIOS) which can control basic hardware and/or software operation such as the interaction with peripheral components or devices.

The profile matcher 2630 represents programmed instructions that cause the processor 2615 to match a user profile with a prescribed product or service. In some examples, the profile matcher 2630 can identify the prescribed products or services that are purchased by the user with the user's profile. This can be accomplished by scanning a database of purchases to find at least some of the user's information with a purchase of a particular product or service. In some cases, the identification number of the product is associated with the profile so that the manufacturing, shipping, and other details about the product are known to the user profile.

Member matcher 2635 represents programmed instructions that cause the processor 2615 to match the prescribed optical device with a set of members of a distribution system of the prescribed optical device. This information can identify who are is the prescriber (e.g. the doctor) of the prescribed product or service, the supplier, and/or the manufacturer. Knowing at least one member of the distribution system allows the user profile to communicate with the distribution system. This can result in improved communication with the manufacturers and thereby resulting in providing the manufacturers with information for improving their products. This can also result in enabling the user profile to open a real time communication channel with the user's doctor for events like requesting a new appointment, modifying instructions to the user, or responding to negative user responses.

Requester 2640 can request information about the prescribed product or service through a user interface. Requesting information can include requesting information on a daily basis. In some cases, the requested information is related to the user's comfort when using the prescribed product or service.

Feedback manager 2650 can send feedback to one of the members of the distribution system based on the received information. In some cases, the feedback includes the received information in an unprocessed format. In alternative cases, the information is processed before being sent. The processing can occur on the device 2605, or the information can be sent to another device for processing before being sent to a member of the distribution system.

In some cases, the processed information can include a total number/frequency of unsatisfactory ratings, a percent of the total number of responses that are unsatisfactory, another factor, or combinations thereof. In some cases, the processed information includes associating the received information with a material of the prescribed optical device. In some cases, the processed information includes associating the received information with a manufacturing date of the prescribed optical device. In some cases, the feedback includes processed information based on the received information. In some cases, the processed information includes associating the received information with at least one aspect of the weather in the area of the user using the prescribed product or service. In some cases, the processed information includes associating the received information with a batch group identifier of the prescribed optical device. In some cases, the processed information includes associating the received information with at least one aspect of manufacturing the prescribed product or service. In some cases, the processed information includes associating the received information with the prescriber of the prescribed product or service. In some cases, the processed information includes associating the received information with a location of the user using the prescribed optical device.

The classification of an unsatisfactory rating can be predetermined. In those cases where the requested information is coupled with a predefined set of responses, each of the predefined responses can be categorized as a satisfactory response or an unsatisfactory response. In such situations, the selection of several different predefined responses can be classified as an unsatisfactory rating. Thus, selecting any of those predefined responses can each result in incrementing the unsatisfactory results number. In some cases, multiple predefined responses are associated with unsatisfactory results, but different predefined responses are associated with varying unsatisfactory values. For example, a selection of a predefined response of "difficult" can result in incrementing the unsatisfactory rating number at a slower rate than selecting a predefined response of "very difficult."

Figure 27:
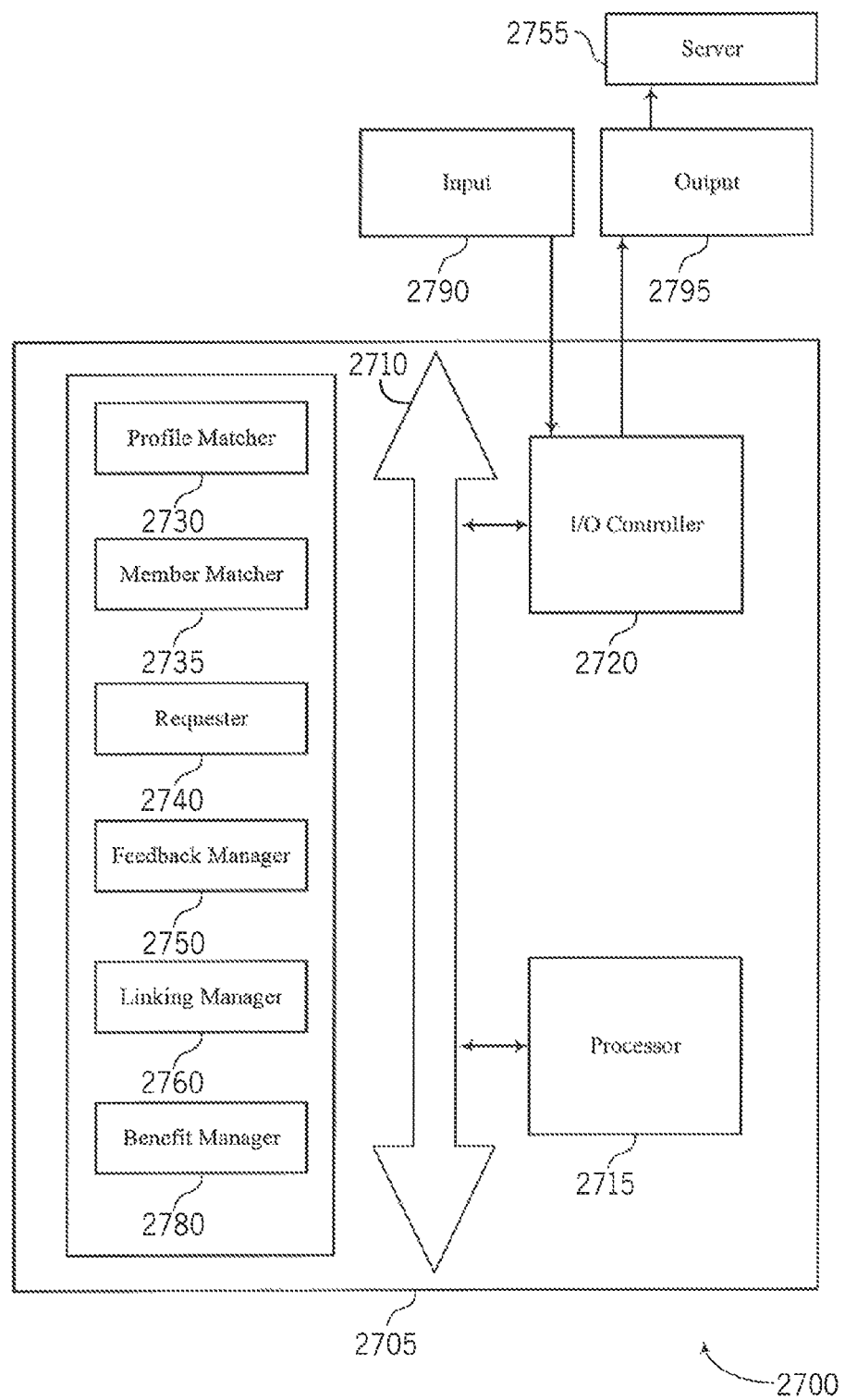
FIG. 27 depicts an example of a block diagram of an evaluation system in accordance with aspects of the present disclosure.

FIG. 27 shows a diagram of a system 2700 including a device 2705 that supports evaluating the user's experience with prescribed products or services in accordance with aspects of the present disclosure. Device 2605 can include components for bi-directional voice and data communications including components for transmitting and receiving communications, including processor 2715, I/O controller 2720, and memory 2725. These components can be in electronic communication via one or more busses (e.g., bus 2710). Memory 2725 can also include profile matcher 2730, member matcher 2735, requester 2740, feedback manager 2750, linking manager 2760, and benefit manager 2780.

Linking manager 2760 can link a user responding to the requested information to a member of the distribution system in response to receiving an unsatisfactory threshold rating in the requested information. In some cases, the linking manager 2760 can link the user to the member in real time. Linking can include opening a text communication channel with the member, presenting an option to schedule an appointment with the member, linking the user to a member of the distribution system in response to receiving an unsatisfactory threshold rating in the requested information, or combinations thereof.

Benefit manager 2780 can award a benefit to the user in response to sending the requested information, creating a profile, providing a level of detailed information about the user's experience, another type of interaction between the user and the user's profile, or combinations thereof. In some cases, the benefit includes a discount on future purchases of prescribed products or services, a membership status, a coupon for a service or product unrelated to prescribed products or services, a preferred status when booking appointments with the doctor, other benefits, or combinations thereof.

In this example, the output 2795 is in communication with a server 2755. But, in other examples, the server 2755 can be direct communication with the I/O controller 2720. The server 2755 can receive the user responses from the users in a processed format, a partially processed format, or in a raw format. The server 2755 can process or further process the information so the information is organized for members of the distribution system to perform the analysis. The server can also process the information to make the information easier to analyze. In some cases, the server performs an analysis on the user's responses. The server can receive responses from multiple users and can organize and/or perform an analysis across a group of users. In some examples, the input 2790 is in communication with the server 2755 and information processed by the server 2755 is relayed back to the user through the user profile and device 2705.

Figure 28:
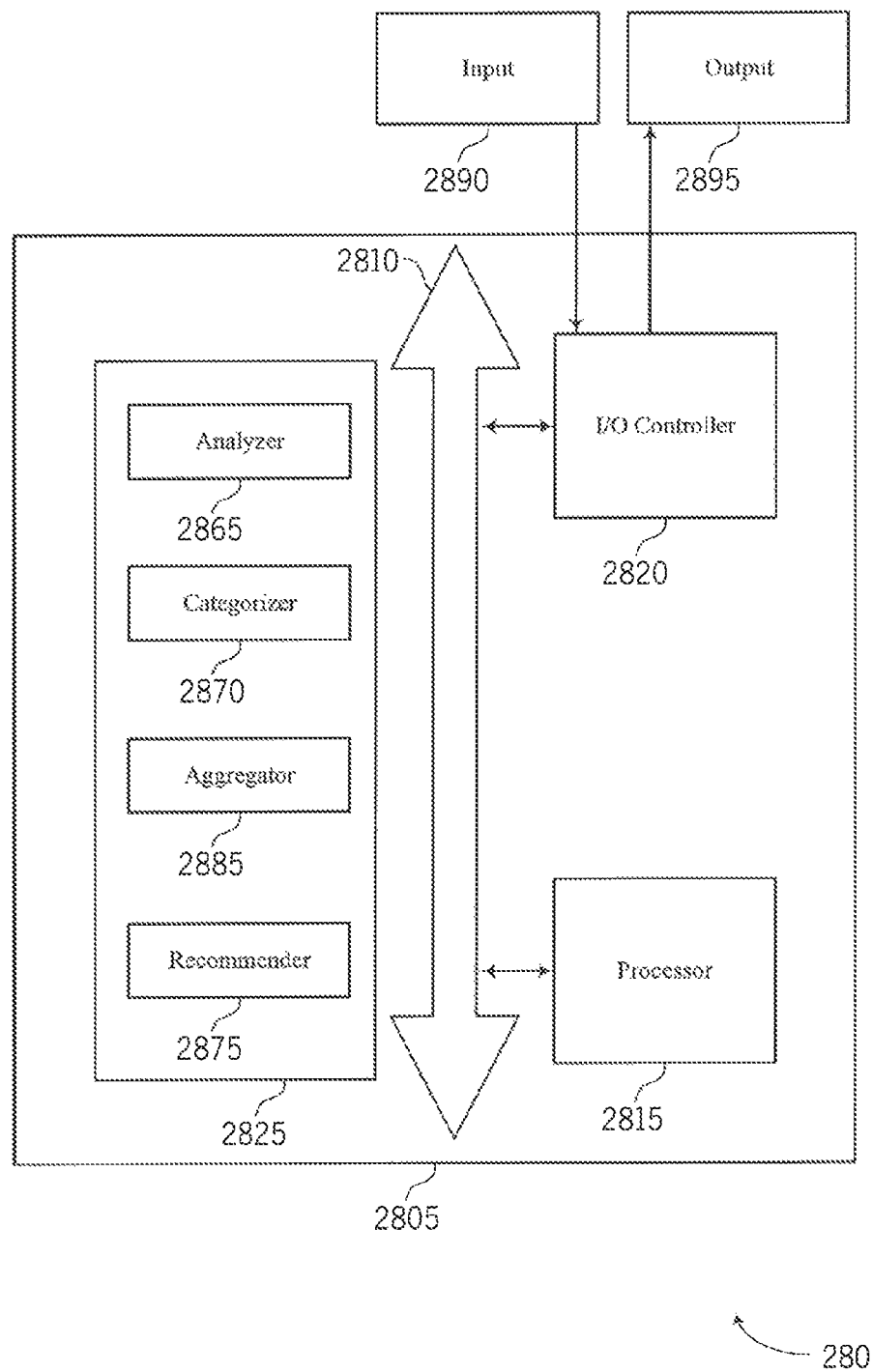
FIG. 28 depicts an example of a method of evaluating a prescribed device in accordance with aspects of the present disclosure.

FIG. 28 shows a diagram of a system 2800 including a device 2805 that supports evaluating the user's experience with prescribed products or services, in accordance with aspects of the present disclosure. Device 2805 can include components for bi-directional voice and data communications including components for transmitting and receiving communications, including processor 2815, I/O controller 2820 in communication with an input 2890 and an output 2895, and memory 2825. These components can be in electronic communication via one or more busses (e.g., bus 2810). Memory 2825 can also include analyzer 2865, categorizer 2870, aggregator 2885, and recommender 2875.

Aggregator 2885 can aggregate the received data. Analyzer 2865 can analyze the information sent from the users by determining when the threshold of unsatisfactory ratings is reached. Categorizer 2870 can categorize types of the unsatisfactory ratings into groups with common characteristics.

Recommender 2875 can recommend a change to a manufacturing process in response to reaching a predetermined threshold of the unsatisfactory ratings, recommend a change of temporarily stopping a portion of the manufacturing process, recommend a change to a material included in a batch of the prescribed products or services, recommend a geometry change to a geometry included in a batch of the prescribed products or services, recommend a change to a shelf life of a batch of the prescribed products or services, recommend another change, or combinations thereof.

To facilitate the reader's understanding of the various functionalities of the embodiments discussed herein, reference is now made to the flow diagrams in FIGS. 29, 30, 31, 32, 33, which illustrates processes 2900, 3000, 3100, 3200, and 3300, respectively. While specific steps (and orders of steps) of the methods presented herein have been illustrated and will be discussed, other methods (including more, fewer, or different steps than those illustrated) consistent with the teachings presented herein are also envisioned and encompassed with the present disclosure.

Figure 29:
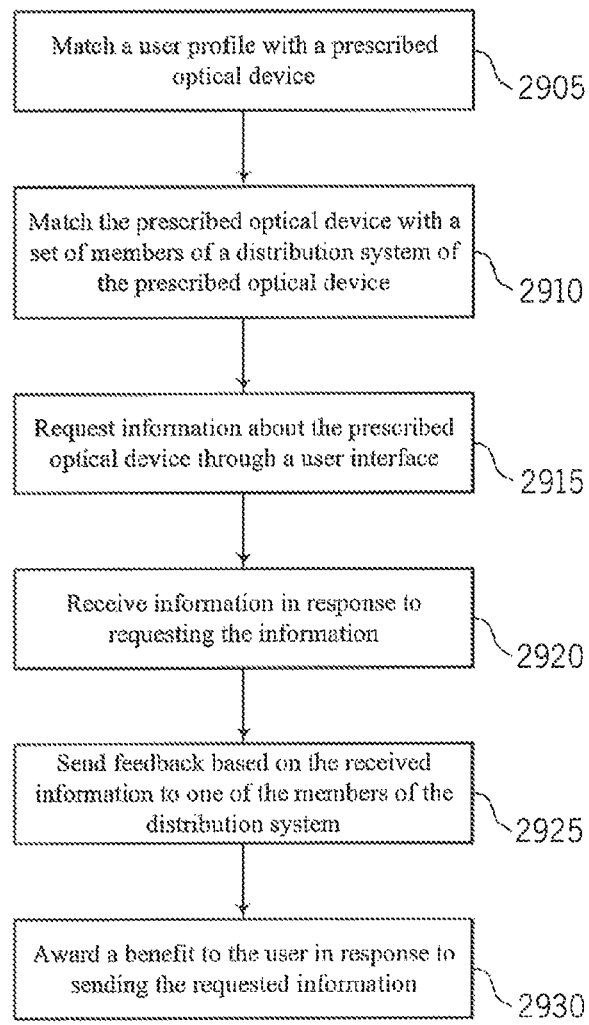
FIG. 29 depicts an example of a method of evaluating a prescribed device in accordance with aspects of the present disclosure.

Turning to FIG. 29, a flowchart illustrating the method 2900 for evaluating prescribed optical devices is shown in accordance with aspects of the present disclosure. In this example, the method 2900 includes matching 2905 a user profile with a prescribed optical device, matching 2910 the prescribed optical device with a set of members of a distribution system of the prescribed optical device, requesting 2915 information about the prescribed optical device through a user interface, 2920 receiving information in response to requesting the information, and sending 2925 feedback based on the received information to one of the members of the distribution system. The operations of method 2900 can be implemented by a device operated by a user or its components as described herein. For example, the operations of method 2900 can be performed by the devices as described with reference to FIGS. 3-23C. In some examples, the device can execute a set of codes to control the functional elements of the device to perform the functions described below. Additionally or alternatively, the device can perform aspects of the functions described below using special-purpose hardware.

At block 2905, a user profile is matched with a prescribed optical device. The operations of block 2905 can be performed according to the methods described with reference to FIGS. 1 through 28. In certain examples, aspects of the operations of block 2905 can be performed by a profile matcher as described with reference to FIGS. 26 and 27.

At block 2910, the prescribed optical device is matched with a plurality of members of a distribution system of the prescribed optical device. The operations of block 2910 can be performed according to the methods described with reference to FIGS. 1 through 28. In certain examples, aspects of the operations of block 2910 can be performed by a member matcher as described with reference to FIGS. 26 and 27.

At block 2915, information about the prescribed optical device is requested through a user interface. The operations of block 2915 can be performed according to the methods described with reference to FIGS. 1 through 28. In certain examples, aspects of the operations of block 2915 can be performed by a requester as described with reference to FIGS. 26 and 27.

At block 2920, information is received. The operations of block 2920 can be performed according to the methods described with reference to FIGS. 1 through 28. In some cases, the information is received in response to answering the requests for information.

At block 2925, feedback based on the received information is sent to one of the members of the distribution system. The operations of block 2925 can be performed according to the methods described with reference to FIGS. 1 through 28. In addition, as illustrated in block 2930, some type of benefit or free merchandise can be provided to the user in exchange for sending the requested information, thereby encouraging participation.

Figure 30:
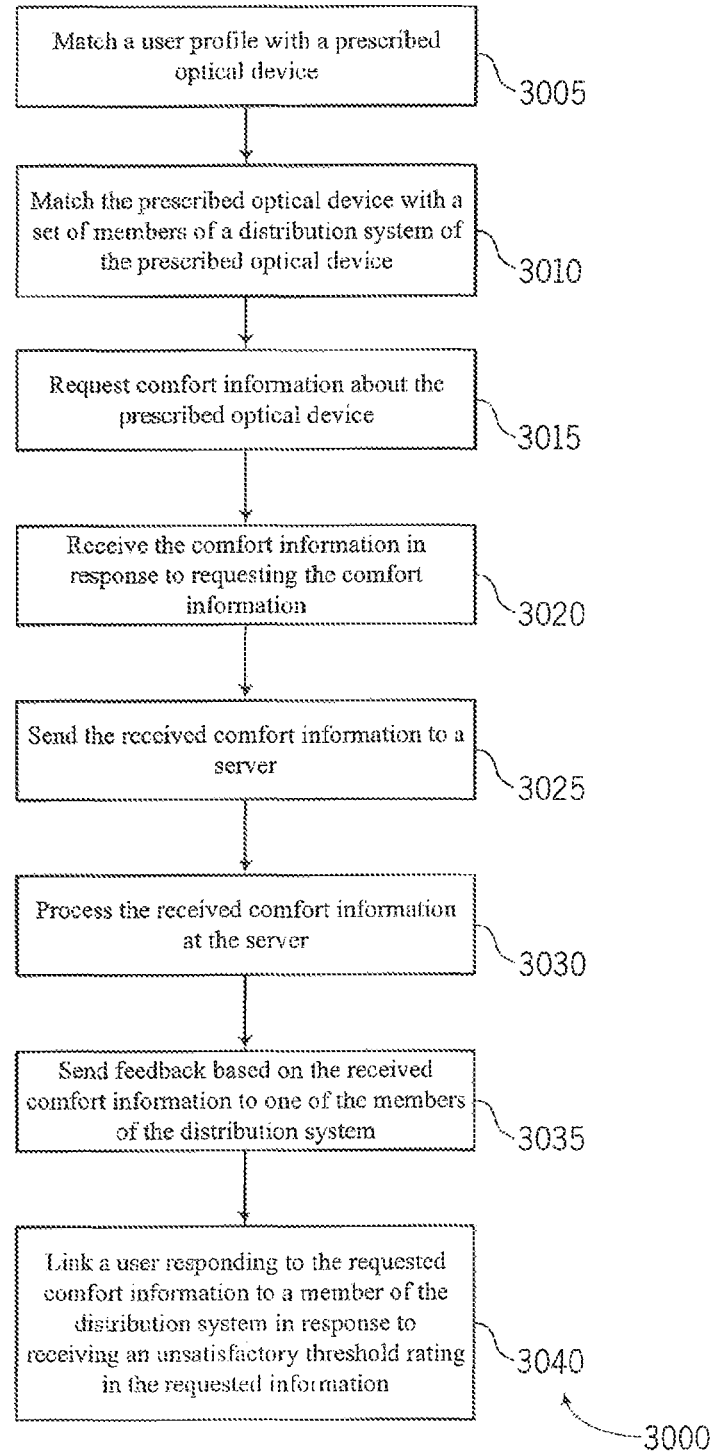
FIG. 30 depicts an example of a method of evaluating a prescribed device in accordance with aspects of the present disclosure.

Turning to FIG. 30, a flowchart illustrating a method 3000 for evaluating prescribed products or services is shown in accordance with aspects of the present disclosure. In this example, the method 3000 includes matching 3005 a user profile with a prescribed products or services, matching 3010 the prescribed products or services with a set of members of a distribution system of the prescribed products or services, requesting 3015 comfort information about the prescribed products or services through a user interface, 3020 receiving comfort information in response to requesting the information, sending 3025 feedback based on the received information to one of the members of the distribution system, processing 3030 the received comfort information at the server, sending 3035 feedback based on the received comfort information to one of the members of the distribution system, and linking 3040 a user responding to the requested comfort information to a member of the distribution system in response to receiving an unsatisfactory threshold rating in the requested information. The operations of method 3000 can be implemented by a device or its components as described herein. For example, the operations of method 3000 can be performed by a device as described with reference to FIGS. 1 through 29. In some examples, the device can execute a set of codes to control the functional elements of the device to perform the functions described below. Additionally or alternatively, the device can perform aspects of the functions described below using special-purpose hardware.

At block 3040, a user can be linked to a member of the distribution system in response to receiving an unsatisfactory threshold rating in the requested information. The operations of block 3040 can be performed according to the methods described with reference to FIGS. 1 through 29. In certain examples, aspects of the operations of block 3040 can be performed by a linking manager as described with reference to FIG. 27.

Figure 31:
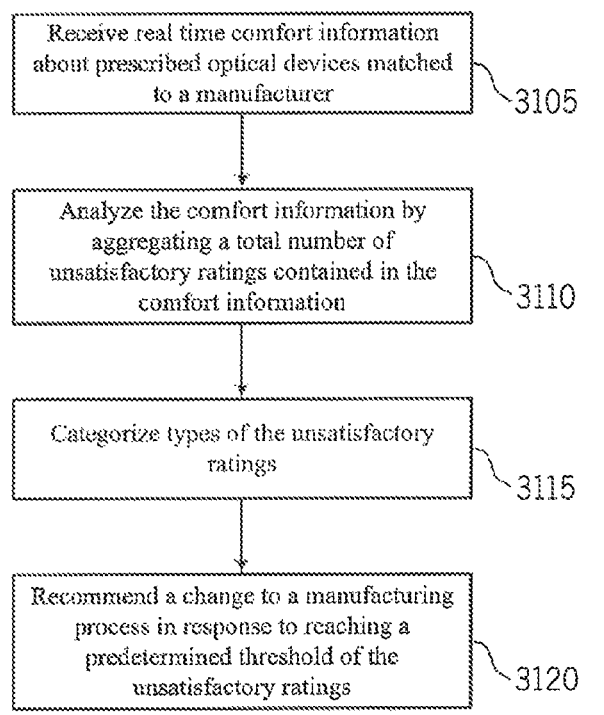
FIG. 31 depicts an example of a method of evaluating a prescribed device in accordance with aspects of the present disclosure.

Turning to FIG. 31, a flowchart illustrating a method 3100 for evaluating prescribed products or services is shown in accordance with aspects of the present disclosure. In this example, the method 3100 includes receiving 3105 real time comfort information about prescribed products or services matched to a manufacturer, analyzing 3110 the comfort information by aggregating a total number of unsatisfactory ratings contained in the comfort information, categorizing 3115 types of the unsatisfactory ratings, and recommending 3120 a change to a manufacturing process in response to reaching a predetermined threshold of the unsatisfactory rating. The operations of method 3100 can be implemented by device or its components as described herein. For example, the operations of method 3100 can be performed by the device as described with reference to FIGS. 1 to 30. In some examples, the device can execute a set of codes to control the functional elements of the device to perform the functions described below. Additionally or alternatively, the device can perform aspects of the functions described below using special-purpose hardware.

At block 3105, real time comfort information is received about prescribed products or services matched by a manufacturer. The operations of block 3105 can be performed according to the methods described with reference to FIGS. 1 through 30. In certain examples, aspects of the operations of block 3105 can be performed by an analyzer as described with reference to FIG. 28.

At block 3110, the comfort information is analyzed by aggregating a total number of unsatisfactory ratings contained in the comfort information. The operations of block 3110 can be performed according to the methods described with reference to FIGS. 1 through 30. In certain examples, aspects of the operations of block 3110 can be performed by an analyzer as described with reference to FIG. 28.

At block 3115, the information is categorized into types of unsatisfactory ratings. The operations of block 3115 can be performed according to the methods described with reference to FIGS. 1 through 30. In certain examples, aspects of the operations of block 3115 can be performed by a categorizer as described with reference to FIG. 28.

At block 3120, recommend is generated to make a change to a manufacturing process in response to reaching a predetermined threshold of the unsatisfactory ratings. The operations of block 3120 can be performed according to the methods described with reference to FIGS. 14 through 17. In certain examples, aspects of the operations of block 3120 can be performed by a recommender as described with reference to FIG. 28.

Figure 32:
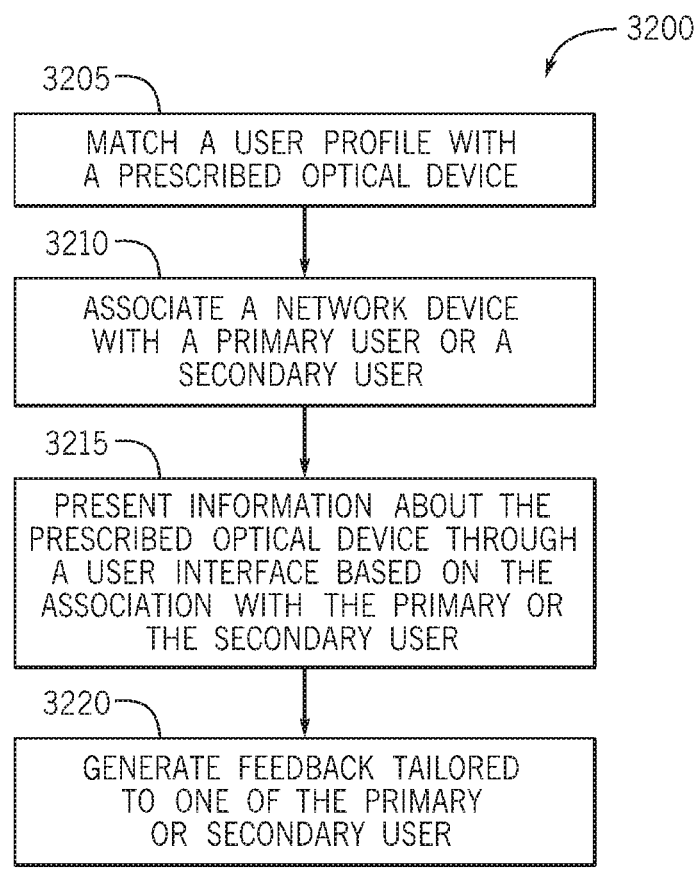
FIG. 32 depicts an example of a method of evaluating a prescribed device in accordance with aspects of the present disclosure.

Turning to FIG. 32, a flowchart illustrating a method 3200 for evaluating prescribed products or services is shown in accordance with aspects of the present disclosure. In this example, the method 3200 includes matching 3205 a user profile with a prescribed optical device, associating 3210 a network device with a primary user or a secondary user, where the user profile corresponding to the secondary user, presenting 3215 information about the prescribed optical device of the primary user through a user interface of the network device based on the association of the network device with the primary or the secondary users, and generating 3220 feedback associated with use of the prescribed optical device through the user interface that is adapted to one of the primary or secondary users. The operations of method 3100 can be implemented by device or its components as described herein. For example, the operations of method 3100 can be performed by the device as described with reference to FIGS. 1 to 31. In some examples, the device can execute a set of codes to control the functional elements of the device to perform the functions described below. Additionally or alternatively, the device can perform aspects of the functions described below using special-purpose hardware.

At block 3205, a user profile is matched with a prescribed optical device. The operations of block 2205 can be performed according to the methods described with reference to FIGS. 1 through 21. In certain examples, aspects of the operations of block 2205 can be performed by a profile matcher as described with reference to FIGS. 26 and 27.

At block 3210, a network device is associated with a primary user or a secondary user. For example, the network device can receive one or more inputs that causes the network device to access a profile of the primary user or the secondary user. The one or more inputs can be a password in certain circumstances that allows the network device to transition between a "parent mode" and a "child mode" according to the embodiments described herein. In other cases, other techniques can be employed for associating the network device with the primary or the secondary user, including using sensors of the network device to detect a user and determine the user as being one of the primary or secondary user.

At block 3215, information about the prescribed optical device is presented through a user interface of the network device. The user interface can be based on the association of the network device with the primary user or the secondary user. For example, where the network device is associated with the primary user and the primary user is a parent, the user interface can present information about the prescribed optical device in "parent mode". As a further example, where the network device is associated with the secondary user and the secondary user is a child, the user interface can present information about the prescribed optical device in "child mode".

As described herein, the child mode can include a condensed and/or more graphical representation of the information that would otherwise be presented.

At block 3220, feedback is generated that is tailored to one of the primary or secondary users. The network device can be adapted to display various messages in order to facilitate the evaluation of the prescribed optical device. The messages can be tailored based on whether the network device is associated with the primary user or the secondary user. For example, where the network device is associated with the primary user and the primary user is a parent, the user interface can provide feedback about the prescribed optical device in "parent mode". As a further example, where the network device is associated with the secondary user and the secondary user is a child, the user interface can provide feedback about the prescribed optical device in "child mode".

Figure 33:
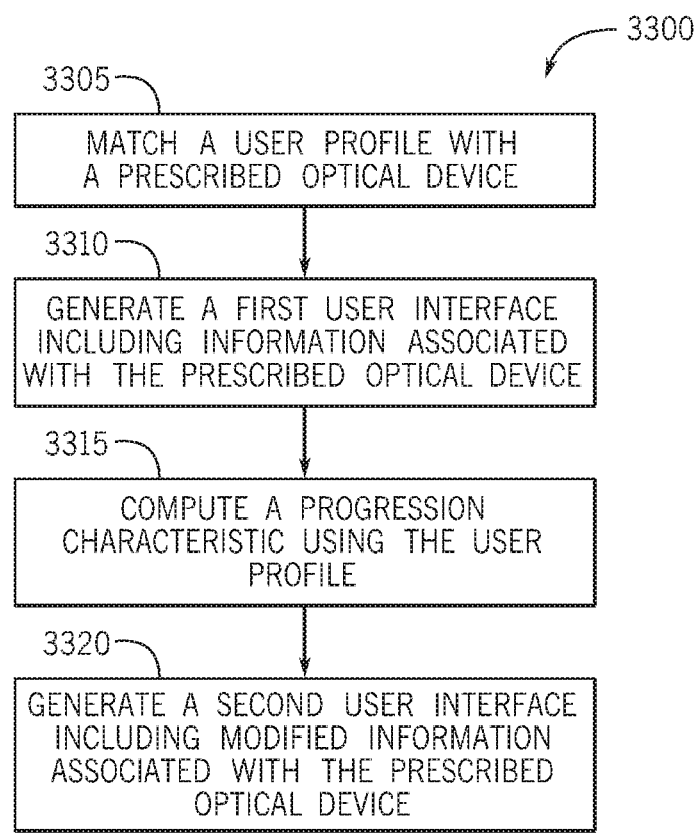
FIG. 33 depicts an example of a method of evaluating a prescribed device in accordance with aspects of the present disclosure.

Turning to FIG. 33, a flowchart illustrating a method 3300 for evaluating prescribed products or services is shown in accordance with aspects of the present disclosure. In this example, the method 3100 includes matching 3305 a user profile with a prescribed optical device, generating 3310 a first user interface at a network device that includes information associated with the prescribed optical device, computing 3215 a progression characteristic of a user profile, and in response to the progression characteristic satisfying a boundary condition, generating 3320 a second user interface at the network device that includes modified information associated with the prescribed optical device. The operations of method 3100 can be implemented by device or its components as described herein. For example, the operations of method 3100 can be performed by the device as described with reference to FIGS. 1 to 32. In some examples, the device can execute a set of codes to control the functional elements of the device to perform the functions described below. Additionally or alternatively, the device can perform aspects of the functions described below using special-purpose hardware.

At block 3305, a user profile is matched with a prescribed optical device. The operations of block 3305 can be performed according to the methods described with reference to FIGS. 1 through 32. In certain examples, aspects of the operations of block 3305 can be performed by a profile matcher as described with reference to FIGS. 26 and 27.

At block 3310, a first user interface is generated at the network device that includes information associated with the prescribed optical device. The first user interface can be adapted to provide progression-appropriate information and content to the user. For example, the user interface of the device 2300*a* is adapted to depict rewards for a younger child.

At block 3315, a progression characteristic is computed using a user profile. As described herein, the user profile can include information associated with, among other items, an age of a user of the prescribed optical device, a compliance history of the user for the prescribed optical device, a treatment progress history of the user for the prescribed optical device, or a medical history of the user of the prescribed optical device. The progression characteristic can be computed using one or more of the age of the user, the compliance history of the user, the treatment progress history of the user, or the medical history of the user. For example, where age is used, the progression characteristic can compute the age of the user.

At block 3320, in response to the progression characteristic satisfying a boundary condition, a second user interface is generated at the network device that includes modified information associated with the prescribed optical device. The boundary condition can be associated with a milestone for a combination of one or more of the age of the user, the compliance history of the user, the treatment progress of the user, or the medical history of the user. In this regard, the milestone can indicative of a progression-based appropriateness of the modified information for the user. The second user interface can therefore be adapted to provide progression-appropriate information and content to the user. For example, the user interface of the devices 2300*b*, 2300*c* are adapted to depict rewards for an older child and teenager, respectively.

Figure 34:
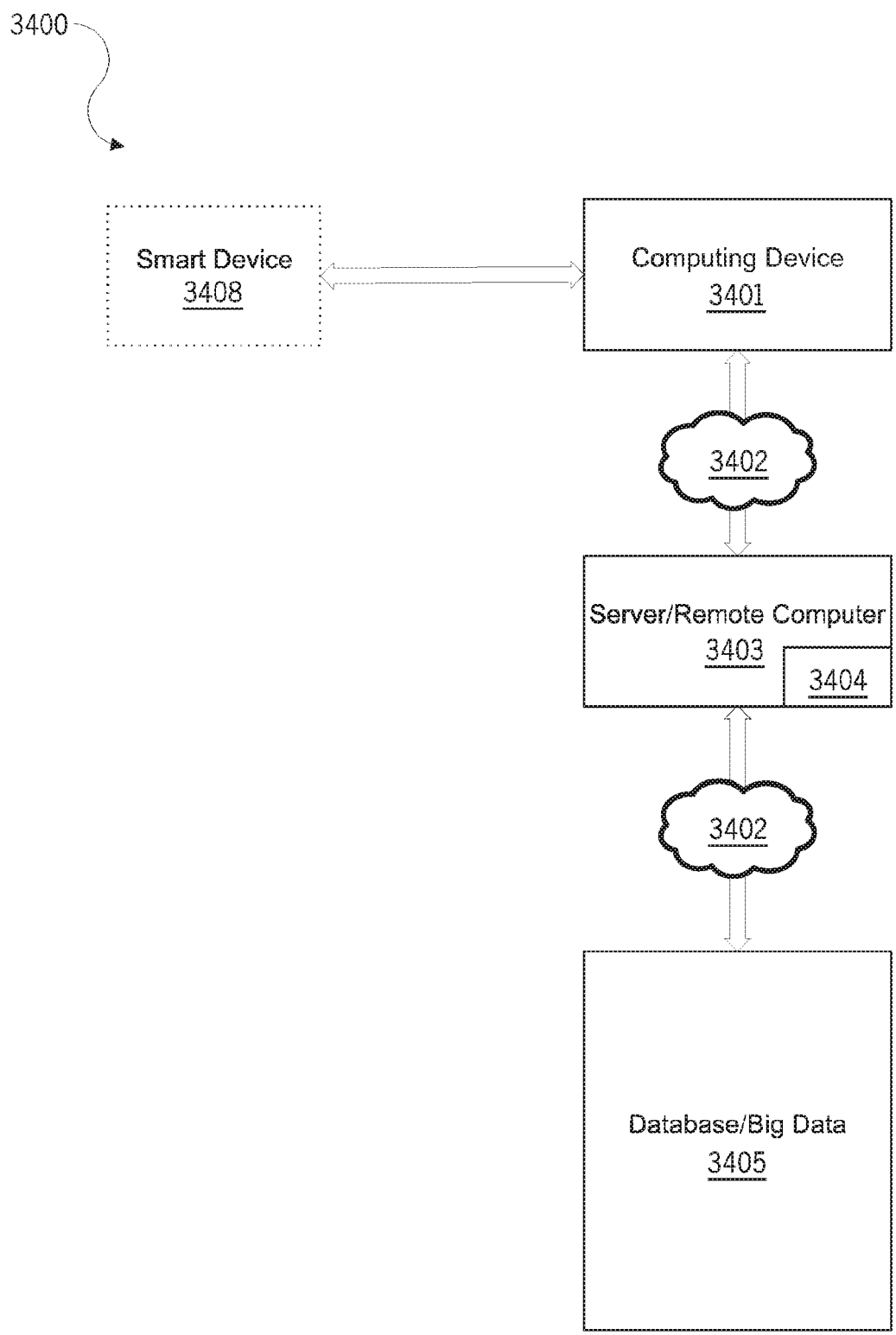
FIG. 34 depicts an example of a system of evaluating prescribed products or services in accordance with the present disclosure.

FIG. 34 illustrates a system 3400 for receiving information about a user, utilizing the received information to determine a treatment, advice, modification, and providing information from a doctor or medical professional to the user. As shown in FIG. 34, the system 3400 includes a computing device 3401 accessible by the user. As mentioned previously, the computing device 3401 can be any type of computing device having a processor and configured to receive a signal and information from a remote source, and to display information, including an avatar of a doctor or other medical professional associated with the user. According to one exemplary embodiment, the computing device 3401 can include a smartphone, a tablet computer, a personal computer, a laptop computer, a gaming system, or any other computing device mentioned above or otherwise configured to receive and process information and display graphical information. As mentioned previously, user information can be transmitted to the system 3400 via the computing device 3401. The user can manually input information to the system using the computing device via an input device such as a keyboard or a touchscreen; information can be automatically collected by the computing device; information can be automatically collected by an associated optional smart device 3408 such as a smart contact lens, smart earphones, or other device configured to evaluate biomarkers or other physiological changes experienced by the user.

Once information is entered into the system 3400, it can be passed to a server or a remote computer 3403 for processing. As illustrated, the data transfer can occur via the cloud 3402 if the server or remote computer 3403 is remote from the computing device 3401. Alternatively, the processing can occur locally on the computing device 3401. A processor 3404 can receive the information and apply any number of rules and/or commands to analyze the data received and select or prepare a response to the user. As shown, a database or other large data collections 3405 can be used to determine the course of action to take with the received user data. Again, the database/big data 3405 database can be remote to the server/remote computer 3403 and can be accessed via the cloud 3402. Once the data, such as detected biomarker indicators, is received and analyzed, a recommended communication can be selected by the server/remote computer 3403 for the user. As noted above, that recommendation can then be delivered to the user on the computing device 3401 by a doctor avatar. The use of the avatar more readily creates trust between the user and the doctor, causes the recommended treatment to be more readily accepted by the user, and reduces the feeling of loneness or isolation by the user.

Additionally, the server/remote computer 3403 can transmit the determined message, along with the gathered information to a doctor for approval and or modification. According to this exemplary embodiment, exposure to the data and recommendation by a licensed doctor prior to transmission of the message to the user's computing device 3401 allows for the writing of valid prescriptions, and allows the licensed doctor to see more patients, lower office overhead, and receive the benefit of artificial intelligence or other heavy computing resources analyzing the biomarkers and other indicators to provide a recommended course of action, if any.

Figure 35:
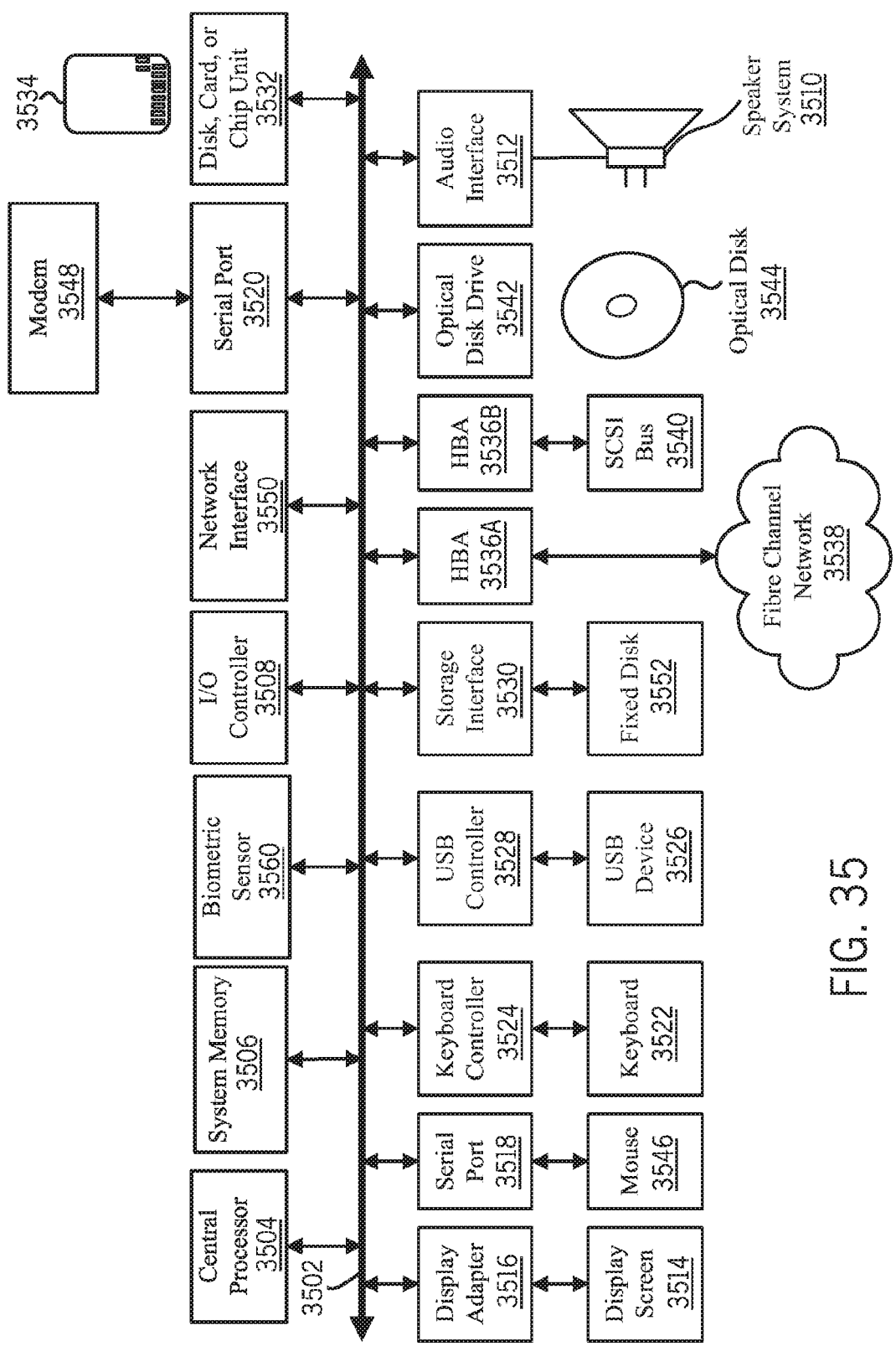
FIG. 35 depicts a block diagram illustrating an example system that can be used in accordance with the present disclosure.

FIG. 35 depicts a block diagram of a computer system 3500 suitable for implementing the present exemplary system and method. The depicted computer system 3500 can be one example of a device described above, such as a smart phone, a wearable, an automobile, a server, a tablet computer, a home computer, and the like. While described in detail with a number of components, the present system can be incorporated into any number of computing systems including all, some, or none of the elements detailed in FIG. 35. Particularly, the present exemplary system can be connected to a system on a chip (SOC) device wherein the functionality of the system is associated with the other components on the chip, rather than through a bus or other system.

As shown in FIG. 35, the computer system 3500 includes a bus 3502 which interconnects major subsystems of computer system 3500, such as a central processor 3504, a system memory 3506 (typically RAM, but which can also include ROM, flash RAM, or the like), an input/output controller 3508, an external audio device, such as a speaker system 3510 via an audio output interface 3512, an external device, such as a disk, card, or chip unit 3532 operative to receive a disk, memory card, or a chip 3534; a display screen 3514 via display adapter 3516; serial ports 3518 and mouse 3520; a keyboard 3522 (interfaced with a keyboard controller 3524); multiple USB devices 3523 (interfaced with a USB controller 3528); a storage interface 3530; a host bus adapter (HBA) interface card 3536A operative to connect with a Fiber Channel network 3538; a host bus adapter (HBA) interface card 3536B operative to connect to a SCSI bus 3540; and an optical disk drive 3542 operative to receive an optical disk 3544. Also included are a mouse 3546 (or other point-and-click device, coupled to bus 3502 via serial port 3518), a modem 3548 (coupled to bus 3502 via serial port 3520), and a network interface 3550 (coupled directly to bus 3502).

Bus 3502 allows data communication between central processor 3504 and system memory 3506, which can include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. Applications resident with computer system 3500 are generally stored on and accessed via a non-transitory computer readable medium, such as a hard disk drive (e.g., fixed disk 3552), an optical drive (e.g., optical drive 3542), or other storage medium. Additionally, applications can be in the form of electronic signals modulated in accordance with the application and data communication technology when accessed via network modem 3548 or interface 3550.

Storage interface 3530, as with the other storage interfaces of computer system 3500, can connect to a standard computer readable medium for storage and/or retrieval of information, such as a fixed disk drive 3552. Fixed disk drive 3552 can be a part of computer system 3500 or can be separate and accessed through other interface systems. Modem 3548 can provide a direct connection to a remote server via a telephone link or to the Internet via an internet service provider (ISP). Network interface 3550 can provide a direct connection to a remote server via a direct network link to the Internet via a POP (point of presence). Network interface 3550 can provide such connection using wireless techniques, including digital cellular telephone connection, Cellular Digital Packet Data (CDPD) connection, digital satellite data connection or the like.

As illustrated in FIG. 35, a biomarker sensor 3560 can be integrated into the computer system 3500. When the biomarker sensor detects a certain biomarker or biomarkers, a signal can be transmitted through the bus to the central processor 3504, which can then access instructions on the system memory 3506, that dictate what subsequent action is taken by the central processor 3504, if any. Many other devices or subsystems (not shown) can be connected in a similar manner (e.g., document scanners, digital cameras and so on). Conversely, all of the devices shown in FIG. 35 need not be present to practice the present systems and methods. The devices and subsystems can be interconnected in different ways from that shown in FIG. 35. The operation of at least some of the computer system 3500 such as that shown in FIG. 35 is readily known in the art and is not discussed in detail in this application. Code to implement the present disclosure can be stored in a non-transitory computer-readable medium such as one or more of system memory 3506; a disk, memory card, or chip 3534; a fixed disk 3552; or optical disk 3544. The operating system provided on computer system 3500 can be MS-DOS®, MS-WINDOWS®, OS/2®, UNIX®, Linux®, or another known operating system.

The description set forth herein, in connection with the appended drawings, describes example configurations and does not represent all the examples that can be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, can be practiced without these specific details. In some instances, well-known structures and devices are shown in block diagram form in order to avoid obscuring the concepts of the described examples.

In the appended figures, similar components or features can have the same reference label. Further, various components of the same type can be distinguished by following the reference label by a dash and a second label that distinguishes among the similar components. If just the first reference label is used in the specification, the description is applicable to any one of the similar components having the same first reference label irrespective of the second reference label.

Information and signals described herein can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative blocks and modules described in connection with the disclosure herein can be implemented or performed with a general-purpose processor, a DSP, an ASIC, an FPGA or other programmable logic device, discrete gate or transistor logic, discrete hardware components, or any combination thereof designed to perform the functions described herein. A general-purpose processor can be a microprocessor, but in the alternative, the processor can be any conventional processor, controller, microcontroller, or state machine. A processor can also be implemented as a combination of computing devices (e.g., a combination of a digital signal processor (DSP) and a microprocessor, multiple microprocessors, one or more microprocessors in conjunction with a DSP core, or any other such configuration).

The functions described herein can be implemented in hardware, software executed by a processor, firmware, or any combination thereof. If implemented in software executed by a processor, the functions can be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions can also be physically located at various positions, including being distributed such that portions of functions are implemented at different physical locations.

Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" can be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium can be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein can be applied to other variations without departing from the scope of the disclosure. Thus, the disclosure is not limited to the examples described herein, but is to be accorded the broadest scope consistent with the principles and novel features disclosed herein.

What is claimed is:

1. A method for evaluating a contact lens, the method comprising:
    matching, using a database of a computer server, a user profile with a contact lens;
    gathering-real-time information, from a user, associated with use of the contact lens by the user;
    associating, at the computer server, a mobile device with a primary user or a secondary user, the user profile corresponding to the secondary user, wherein the user profile adapts the mobile device based on the association of the mobile device with either the primary user or the secondary user, wherein an accessing of the user profile by the primary user provides a different suite of options, data summaries, or programs;

presenting, at a display of a mobile computing device, an icon or a graphic associated with use of the contact lens;

detecting an input, at the mobile device, in response to the presented icon or graphic;

generating feedback, at the display, associated with use of the contact lens that is adapted to one of the primary or secondary users;

matching, at the computer server, the contact lens with one or more members of a distribution system;

computing, at the computer server, a progression characteristic of the user profile using the medical history of the primary or secondary user and at least one of the age, the compliance history, the treatment progress history, or the medical history of the primary or secondary user as determined by the system; and sending the feedback, from the computer server, to the one or more members of the distribution system based on the detected input, wherein the one or more members of the distribution system include one or more of a prescriber of the contact lens, a supplier of the contact lens, or a manufacture of the contact lens.

2. The method of claim 1, wherein the primary user is a parent and the secondary user is a child.

3. The method of claim 1, wherein:

in a first mode, the mobile device is associated with the primary user and the operation of presenting the icon or graphic further includes generating a first user interface having a first quantity of attributes associated with use of the contact lens; and in a second mode, the mobile device is associated with the secondary user and the operation of presenting the icon or graphic further includes generating a second user interface having a second quantity of attributes associated with use the contact lens, the second quantity of attributes being a condensed version of the first quantity of attributes.

4. The method of claim 1, wherein:

in a first mode, the mobile device is associated with the primary user and the operation of presenting the icon or graphic further includes generating a first user interface having a textual depiction of attributes associated with the contact lens; and in a second mode, the mobile device is associated with the secondary user and the operation of presenting the icon or graphic further includes generating a second user interface having a graphical depiction of attributes associated with the contact lens, the graphical depiction being visually representative of the textual depiction.

5. The method of claim 1, wherein:

in a first mode, the mobile device is associated with the primary user and the operation of presenting the icon or graphic further includes generating a first user interface depicting a representation of a history of interactions of the secondary user with the contact lens; and in a second mode, the mobile device is associated with the secondary user and the operation of presenting the icon or graphic further includes generating a second user interface depicting a representation of rewards based on the history of interaction of the secondary user with the contact lens.

6. The method of claim 1, wherein the operation of associating comprises:

capturing one or more images of the primary user or the secondary user for one or both of a facial recognition process or a retina scan process, using one or more sensors of the mobile device; and determining the one or more images corresponds to one of the primary user or the secondary user.

7. The method of claim 6, wherein:

the mobile device is associated with the secondary user; and the operation of presenting the icon or graphic further includes providing a prompt for transitioning the mobile device to the primary user.

8. The method of claim 1, wherein the method further includes requesting information about the contact lens through the user interface of the mobile device.

9. The method of claim 8, wherein the method further includes:

receiving information in response to requesting the information; and attributing the received information to one of the primary or secondary users.

10. The method of claim 9, wherein the operation of generating feedback further includes updating the user interface based on the received information and the attribution of the received information to one of the primary or secondary users.

11. The method of claim 1, wherein use of the contact lens comprises one or more of a comfort level of the contact lens, a user compliance with a treatment plan of the contact lens, or an efficacy of the contact lens.

12. A method for evaluating a contact lens, the method comprising:

matching, using a database of a computer server, a user profile with a contact lens;

generating, at a display of a mobile device, a first user interface that includes an icon or graphic associated with use of the contact lens;

computing, at the computer server, a progression characteristic of the user profile;

associating the mobile device with a primary user or a secondary user, the user profile corresponding to the secondary user;

generating the first user interface at the display based on the association of the mobile device with the primary user or the secondary user, wherein the association of the mobile device with the primary user provides a first set of options, data summaries, or programs, wherein the association of the mobile device with the secondary user provides a second set of options, data summaries, or programs that is a condensed version of the first set, wherein the primary user is a parent and the secondary user is a child;

in response to the progression characteristic satisfying a boundary condition, generating, at the display of the mobile device, a second user interface that includes a modified icon or graphic associated with use of the contact lens;

computing the progression characteristic using the medical history of the user and at least one of the age of the user, the compliance history of the user, the treatment progress history of the user, or the medical history of the user as determined by the system;

matching, at the computer server, the contact lens with one or more members of a distribution system; and sending feedback, from the computer server, to the one or more members of the distribution system based on the progression characteristic, wherein the one or more members of the distribution system include one or more of a prescriber of the contact lens, a supplier of the contact lens, or a manufacture of the contact lens.

13. The method of claim 12, wherein:
the user profile includes information corresponding to one or more of an age of a user of the contact lens, a compliance history of the user for the contact lens, a treatment progress history of the user for the contact lens, or a medical history of the user of the contact lens.

14. The method of claim 12, wherein one or more of the age of the user, the compliance history of the user, the treatment progress history of the user, or the medical history of the user is determined, at least in part, using sensors of the mobile device that are configured to capture one or more images for one or both of a facial recognition process or a retina scan process.

15. The method of claim 12, wherein the boundary condition is associated with a milestone for a combination of one or more of the age of the user, the compliance history of the user, the treatment progress of the user, or the medical history of the user.

16. The method of claim 12, wherein the method further includes requesting information about the contact lens through the first user interface or the second user interface of the mobile device.

17. The method of claim 12, wherein the method further includes:
receiving information in response to requesting the information; and
attributing the received information to one of the first user interface or the second user interface.

18. The method of claim 12, further comprising generating feedback associated with use of the contact lens through the mobile device that is adapted to one of the first user interface of the second user interface.

19. The method of claim 12, wherein:
the first user interface includes a depiction of a first quantity of attributes associated with use the contact lens; and
the second user interface includes a depiction of a second quantity of attributes associated with use of the contact lens, the second quantity of attributes being a condensed version of the first quantity of attributes.

20. A system for evaluating a contact lens, the system comprising:
a processor;
a database;
a display of a mobile device, the display configured to define a user interface; and
a non-transitory computer-readable media encoded with instructions which, when executed by the processor, causes the processor to:
match, using the database, a user profile with a contact lens;
compute a progression characteristic of the user profile, wherein the user profile includes information corresponding to a medical history of the user of the contact lens, a compliance history of the user for the contact lens, and one or more of an age of a user of the contact lens, or a treatment progress history of the user for the contact lens as determined by the system; and
compute the progression characteristic using at least one of the age of the user, the compliance history of the user, the treatment progress history of the user as determined by the system, or the medical history of the user;
match the contact lens with one or more members of a distribution system, wherein the one or more members of the distribution system include one or more of a prescriber of the contact lens, a supplier of the contact lens, or a manufacture of the contact lens;
generate a first user interface at the display including an icon or graphic associated with use of the contact lens;
associate the mobile device with a primary user or a secondary user, the user profile corresponding to the secondary user;
generate the first user interface at the display based on the association of the mobile device with the primary user or the secondary user, the first user providing a different suite of options, data summaries, or programs based on the association of the mobile device with the primary user or the secondary user;
receive feedback associated with the primary user or the secondary user of the mobile device; and
using the received feedback, generate a second user interface including a modified icon or graphic associated with use of the contact lens, and
send the received feedback to the one or more members of the distribution system.

21. The system of claim 20, wherein the non-transitory computer-readable media stores further instruction which, when executed by the processor, causes the processor to:
associate the mobile device with a primary user or a secondary user, the user profile corresponding to the secondary user; and
generate the first user interface at the display based on the association of the mobile device with the primary user or the secondary user.

22. The system of claim 21, wherein:
in a first mode, the mobile device is associated with the primary user, the first graphical interface includes a first quantity of attributes associated with use the contact lens; and
in a second mode, the mobile device is associated with the secondary user, the first graphical interface includes a second quantity of attributes associated with use of the contact lens, the second quantity of attributes being a condensed version of the first quantity of attributes.

23. The system of claim 22, wherein the first quantity of attributes are visually represented via the first user interface with text, and the second quantity of attributes are visually represented via the second user interface with icons.

24. The system of claim 21, wherein the operation of associating comprises using the received feedback to transition the mobile device between a child mode associated with the secondary user and a parent mode associated with the primary user.

25. The system of claim 20, wherein
in response to the progression characteristic satisfying a boundary condition, generate the second user interface including the modified icon or graphic.

26. The system of claim 20, wherein the non-transitory computer-readable media stores further instructions which, when executed by the processor, cause the processor to:
receive a signal from the one or more members of the distribution system, based on the sent feedback; and
update one or both of the first or second interfaces based on the received signal.

* * * * *